United States Patent [19]
Brill et al.

[11] Patent Number: 5,299,121
[45] Date of Patent: Mar. 29, 1994

[54] NON-PRESCRIPTION DRUG MEDICATION SCREENING SYSTEM

[75] Inventors: Albert R. Brill, Sylmar; Denis Sosnoski, Garden Grove, both of Calif.

[73] Assignee: Medscreen, Inc., Sylmar, Calif.

[21] Appl. No.: 893,652

[22] Filed: Jun. 4, 1992

[51] Int. Cl.$^5$ ............................................. G06F 15/42
[52] U.S. Cl. ........................... 364/413.01; 364/413.02; 395/924
[58] Field of Search ...................... 364/413.01, 413.02, 364/400, 401; 395/924

[56] References Cited

U.S. PATENT DOCUMENTS

| | | |
|---|---|---|
| 3,934,226 | 1/1976 | Stone et al. . |
| 4,130,881 | 12/1978 | Haessler et al. . |
| 4,290,114 | 9/1981 | Sinay . |
| 4,464,122 | 8/1984 | Fuller et al. . |
| 4,489,387 | 12/1984 | Lamb et al. . |
| 4,695,954 | 9/1987 | Rose et al. . |
| 4,785,969 | 11/1988 | McLaughlin . |
| 4,839,822 | 6/1989 | Dormond et al. ............ 364/413.02 |
| 4,847,764 | 7/1989 | Halvorson . |
| 4,872,122 | 10/1989 | Altschuler et al. ............ 364/413.02 |
| 4,991,091 | 2/1991 | Allen . |
| 5,025,374 | 6/1991 | Roizen et al. . |
| 5,036,462 | 7/1991 | Kaufman et al. . |
| 5,199,439 | 4/1993 | Zimmerman et al. ......... 364/413.02 |

FOREIGN PATENT DOCUMENTS 59-231676 12/1984 Japan .

*Primary Examiner*—Robert A. Weinhardt
*Attorney, Agent, or Firm*—Blakely, Sokoloff, Taylor & Zafman

[57] ABSTRACT

A system for use in pharmacies which uses customer inputs to assist the customer with the selection of an appropriate non-prescription medication to relieve symptoms of an illness, injury or the like. The system uses an expert system to perform the selection. The system utilizes a personal computer with a keyboard, monitor and disk drive as input/output devices with appropriate programming for prompting a user to input information which is used by a knowledgebase to determine non-prescription medications which may be purchased by the customer to relieve symptoms of injuries and illnesses covered by the knowledgebase. The system operates by prompting a user at typically a customer in a pharmacy to input basic customer information. After the basic customer information has been input the customer is prompted to select one main symptom category from a list displayed and the choice made results in the appropriate knowledgebase being loaded for the next step. The logic of the loaded knowledgebase itself determines which questions are asked of the customer by the display of appropriate questions on the monitor. The output of each knowledgebase on completion of the questions and answers is a list of component medications recommended for use with the symptoms described. The list of component medications generated by the execution of the knowledgebase is used to search a database to find the appropriate product to be recommended.

4 Claims, 11 Drawing Sheets

NON-PRESCRIPTION DRUG MEDICATION SCREENING SYSTEM

SUMMARY OF THE INVENTION

The invention is a system for use in pharmacies which uses customer inputs to assist the customer with the selection of an appropriate non-prescription medication to relieve symptoms of an illness, injury or the like. The system uses an expert system to perform the selection and thereby free-up the time of the pharmacists to the extent that customers are able to obtain information and suggestions for non-prescription medications which they would otherwise obtain from the pharmacists. In this manner, by reducing the amount of time needed by the pharmacists to answer customer questions relating to non-prescription medications, the pharmacists are able to devote more time to the filling of prescriptions and other required tasks.

The system utilizes a personal computer with a keyboard, monitor and disk drive as input/output devices with appropriate programming for prompting a user to input information which is used by a knowledgebase to determine non-prescription medications which may be purchased by the customer to relieve symptoms of injuries and illnesses covered by the knowledgebase. The system incorporates six main sections as follows:
1. Input Customer Information
2. Select Main Symptom
3. Execute Symptom Knowledgebase
4. Select Product Recommendation
5. Generate Session Report
6. Close Session The system operates by prompting a user, typically a customer in a pharmacy, to input basic customer information such as the customer name, gender, and date of birth. After the basic customer information has been input, the customer is prompted to select one main symptom category from a list displayed. Each category corresponds to a separate knowledgebase, and the choice made results in the appropriate knowledgebase being loaded for the next step.

Once the knowledgebase for the selected main symptom has been loaded, it begins its execution. The logic of the knowledgebase itself determines which questions are asked of the customer by the display of appropriate questions on the monitor. The customer answers each question, as appropriate.

The output of each knowledgebase on completion of the questions and answers is a list of component medications recommended for use with the symptoms described. The list of component medications generated by the execution of the knowledgebase is used to search a database to find the appropriate product to be recommended. After selecting the first product to be recommended, the component medications present in this product are removed from the list of recommended component medications. If any component medications remain in the resulting list, another product is selected in the same way. This continues until each component medication recommended by the knowledgebase is present in one and only one recommended product.

Once the recommended product or products have been determined, a session report for the customer is generated, which may be printed immediately or queued for later printing. The actual product recommendations follow the session summary. For each recommended product, a session report is printed with the product name and a summary of usage information for the product. This information may include warnings and usage restrictions as well as actual directions for use.

DETAILED DESCRIPTION OF THE INVENTION

The invention is a system for use in pharmacies which uses customer inputs to assist the customer with the selection of an appropriate non-prescription medication. The system uses an expert system to perform the selection and thereby free-up the time of the pharmacists to the extent that customers are able to obtain information and suggestions for non-prescription medications which they would otherwise obtain from the pharmacists. In this manner, by reducing the amount of time needed by the pharmacists to answer customer questions relating to non-prescription medications, the pharmacists are able to devote more time to the filling of prescriptions and perform other tasks.

Figure 1:
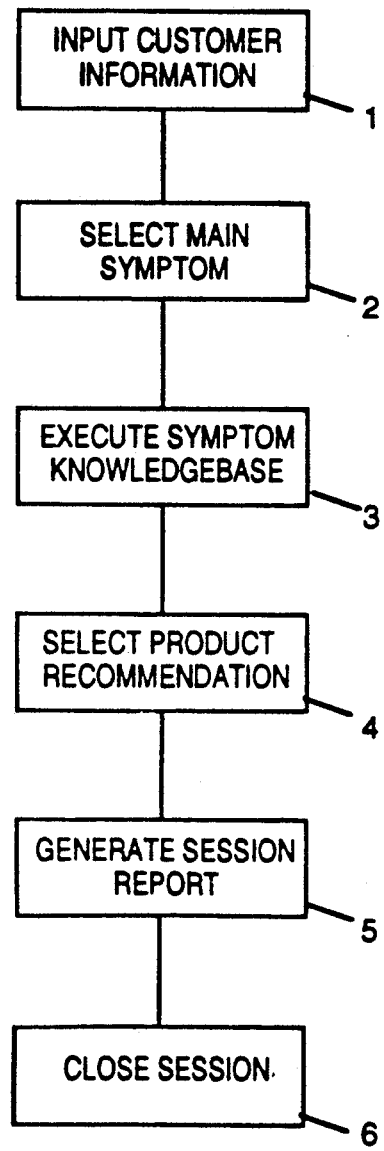
FIG. 1 is an overview of the invented system in flow chart form.
Figure 2A:
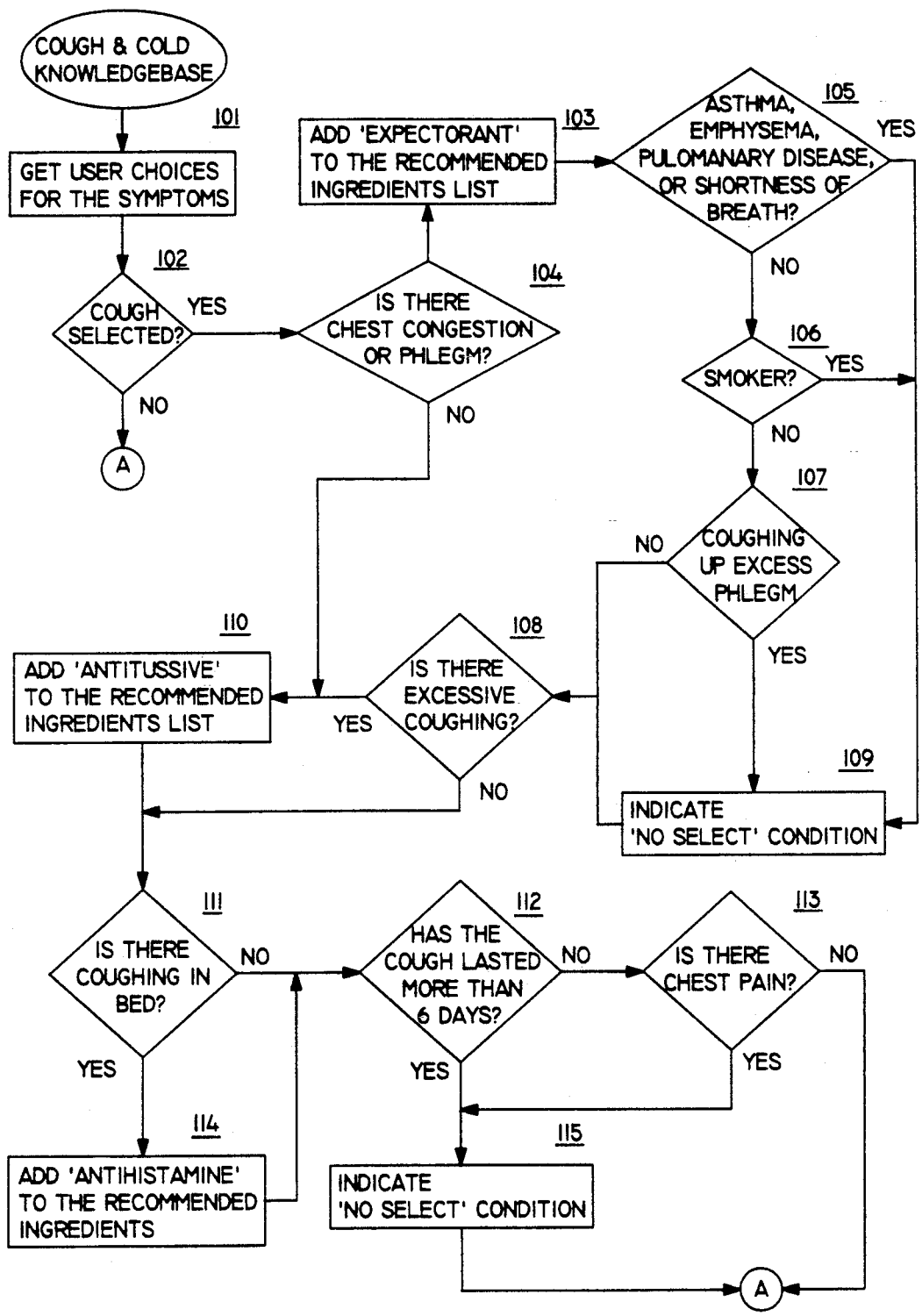
FIG. 2a-2e is flow chart showing the execution of a knowledgebase for cough and cold symptoms.
Figure 2B:
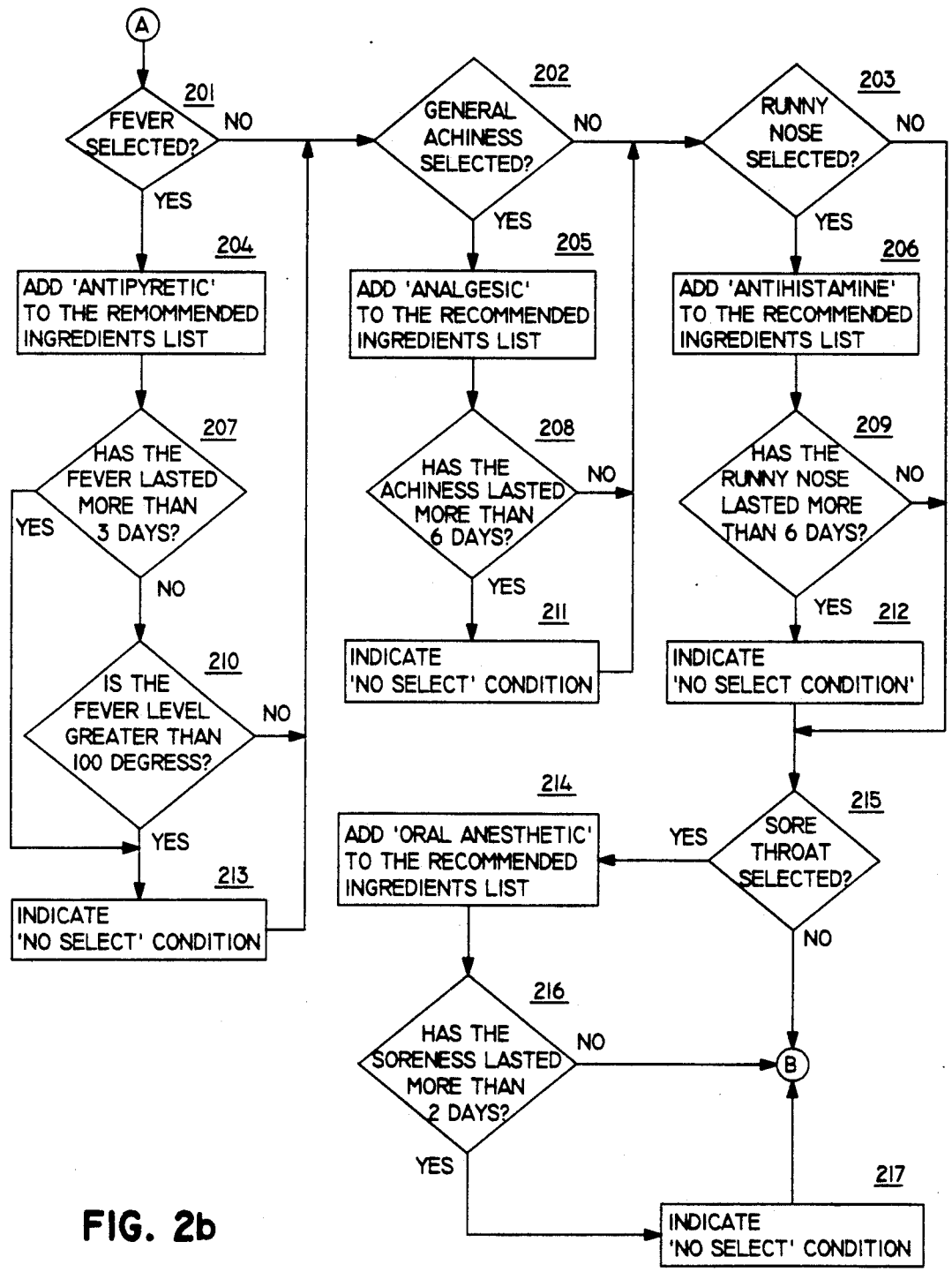
Figure 2C:
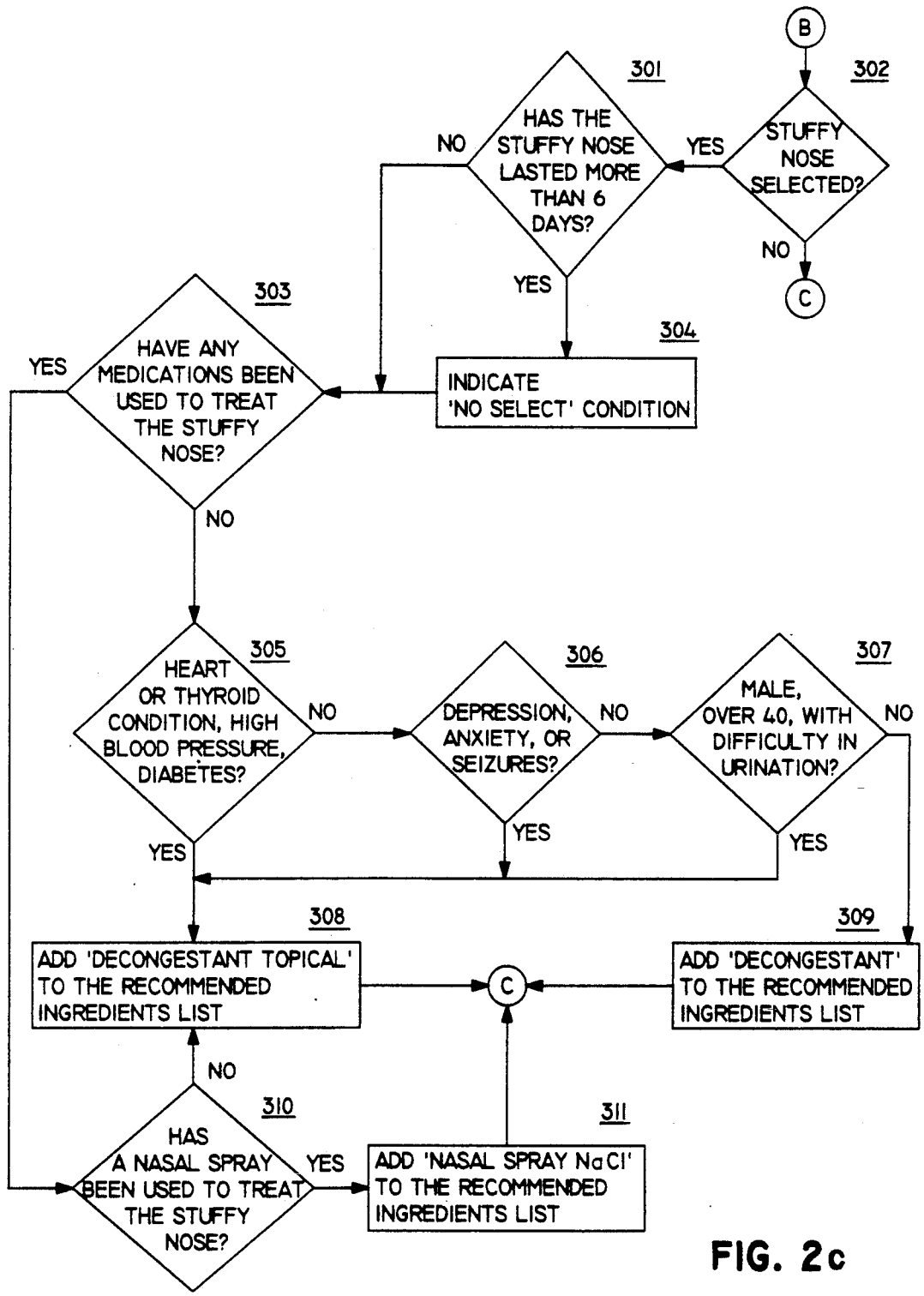
Figure 2D:
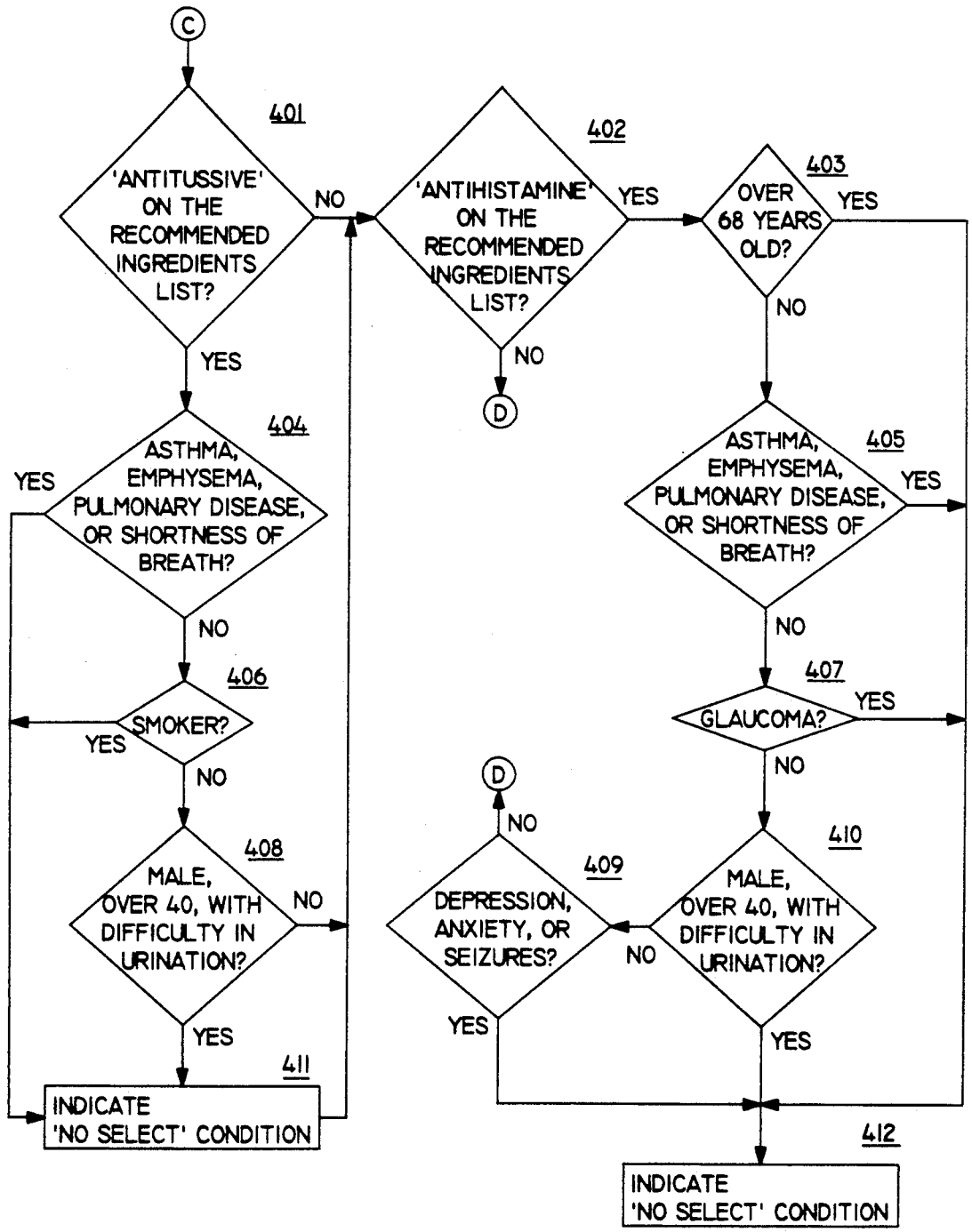
Figure 2E:
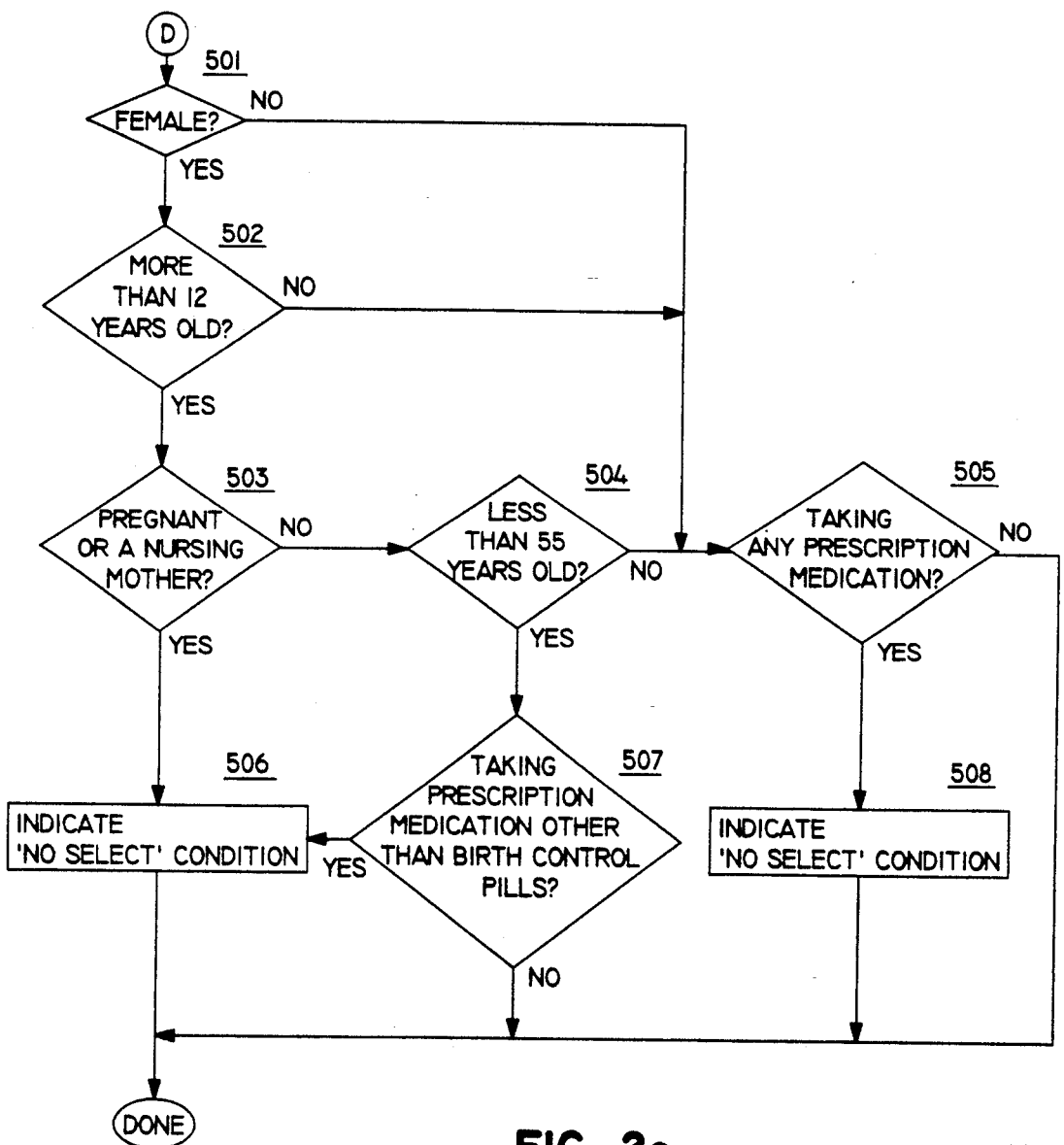

The system comprises a personal computer with a keyboard, monitor and disk drive as input/output devices with appropriate programming for prompting a user to input information which is used by a knowledgebase to determine non-prescription medications which may be purchased by the customer to relieve symptoms of injuries or illnesses covered by the knowledgebase. A suitable personal computer which may be used is an IBM 386 or compatible with a VGA color monitor and at least a 40 MByte disk drive. As shown in FIG. 1, the system incorporates six main sections or routines as follows:
1. Input Customer Information
2. Select Main Symptom
3. Execute Symptom Knowledgebase
4. Select Product Recommendation
5. Generate Session Report
6. Close Session

1. Input Customer Information

This routine prompts a user for basic customer information such as customer name, gender, and date of birth. Other items of information may also be prompted for, such as a recent blood pressure reading. If the necessary auxiliary equipment is present on the system being used, the customer may be able to have measurements such as blood pressure taken and input directly to the system. The results are then displayed for the customer as well as used internally.

Each customer selects a "password" code the first time they use a particular system. When the customer returns to the same system at another time, the customer can then identify himself or herself as an existing customer and avoid reentering the basic customer information. As a security precaution, the password code is not displayed after it is initially input. This is to help prevent anyone from misidentifying themselves as an existing customer, which would cause the wrong information to be supplied to the other knowledgebase. Suitable software for implementing the Input Customer Information routine should be apparent to a person skilled in the art. One such suitable routine in C is attached hereto as part of Appendix 1.

2. Select Main Symptom

This routine requests the customer to select one main symptom category from a list displayed. Each category corresponds to a separate knowledgebase, and the choice made results in the appropriate knowledgebase being loaded for the next routine. In the presently preferred embodiment, the list contains the following symptom categories:
a) Cough and Cold
b) Pain
c) Stomach Problems
d) Allergies This list of symptom categories displayed to the customer is easily changed, so that new areas of selection can be added to existing systems. This allows the range of problems for which the system can supply recommendations to increase over time. Suitable software for implementing the Select Main Symptom routine should be apparent to a person skilled in the art. One such suitable routine in C is attached hereto as part of Appendix 1.

3. Execute Symptom Knowledgebase

In this routine, the knowledgebase corresponding to the main symptom category selected is loaded and executed. The logic of the knowledgebase itself determines which questions are asked of the customer during this step of the consultation. This allows new knowledgebases to be added to the system without requiring changes to the programming.

Certain inputs which may be requested by the knowledgebase, such as the customer age, are provided automatically by the system based on the information provided from responses to questions generated by the Input Customer Information routine. These questions from the knowledgebase are not seen by the user.

The output of each knowledgebase on completion is a list of component medications recommended for use with the symptoms described. The knowledgebases must also determine whether potential problems may exist with the customer using the recommended medications. In the case of such a problem, the knowledgebase continues execution to select the most appropriate medication available for the symptom within the range of medications supported. The potential customer problems, if any, are then brought to the attention of the pharmacist when the session report is generated, as described below.

The currently available knowledgebases are Cough and Cold, Pain, Stomach Problems, and Allergies. A written definition of these knowledgebases in a logic programming language form is set forth in Appendices 2-5 respectively.

A flow diagram for the execution of the Cough and Cold knowledgebase is shown in FIGS. 2a-2e. The user choices for the particular symptoms being experienced are obtained at 101. These symptoms may be one or more of Cough tested at 102, Fever at 201, General Achiness at 202, Runny Nose at 203, Sore Throat at 215, or Stuffy Nose at 302.

If the Cough symptom has been selected at 102, various tests are made to determine the need for various possible component medications. If chest congestion or phlegm is present at 104, 'expectorant' is included as a component medication at 103. If chest congestion or phlegm is absent at 104, or present along with excessive coughing at 108, 'antitussive' is included as a component medication at 110. If coughing in bed is being experienced at 111, 'antihistamine' is included as a component medication at 114.

If the Fever symptom has been selected at 201, 'antipyretic' is always included as a component medication at 204. If the General Achiness symptom has been selected at 202, 'analgesic' is always included as a component medication at 205. If the Runny Nose symptom has been selected at 203, 'antihistamine' is always included as a component medication at 206. If the Sore Throat symptom has been selected at 215, 'oral anesthetic' is always included as a component medication at 214.

If the Stuffy Nose symptom has been selected at 302, various tests are made to select the appropriate type of component medication. If a medication has been used to treat the stuffy nose at 303, and furthermore a nasal spray has been used to treat the stuffy nose at 310, 'Nasal Spray NaCl' is selected as a component medication at 311. If a medication has been used to treat the stuffy nose at 303, but not a nasal spray at 310, 'decongestant topical' is selected as a component medication at 308. This same choice of 'decongestant topical' at 308 is also made if no medication has been used to treat the stuffy nose at 303, but any of the following conditions is present: Heart or thyroid condition, high blood pressure, or diabetes at 305; depression, anxiety, or seizures at 306; or a male over 40 years old with difficulty in urination at 307. If no medications have been used to treat the stuffy nose at 303, and none of the above listed conditions at 305, 306, or 307 are present, 'decongestant' is selected as a component medication at 309.

In this manner a list of recommended ingredients is built depending upon the symptoms and health and condition of the customer. Each type of medication, and in some cases individual types of symptoms, has conditions which indicate potential problems with the use of the medication. If such a potential problem is found with a recommended component medication, 'no select' is added to the list of component medications as an indication that the pharmacist must personally review the recommendation and discuss the potential problems with the customer.

For the 'expectorant' component medication, any of the following conditions will result in 'no select' being included as a component medication at 109: Asthma, emphysema, pulmonary disease, or shortness of breath at 105; smoker at 106; or coughing up excess phlegm at 107.

For the Cough symptom in general, 'no select' is included at 115 if either the cough has lasted more than 6 days at 112, or chest pain is present at 113. For the Fever symptom, 'no select' is included at 213 if either the fever has lasted more than 3 days at 207 or the fever level is greater than 100 degrees at 210. For the General Achiness symptom, 'no select' is included at 211 if the achiness has lasted more than 6 days at 208. For the Runny Nose symptom, 'no select' is included at 212 if the runny nose has lasted more than 6 days at 209. For the Sore Throat symptom, 'no select' is included at 217 if the soreness has lasted more than 2 days at 216. For the Stuffy Nose symptom, 'no select' is included at 304 if the stuffy nose has lasted more than 6 days at 301.

For the 'antitussive' component medication, any of the following conditions will result in 'no select' being included as a component medication at 411: Asthma, emphysema, pulmonary disease, or shortness of breath at 404; smoker at 406; or a male over 40 years old with difficulty in urination at 408. For the 'antihistamine' component medication, any of the following conditions will result in 'no select' being included at 412: over 8 years old at 403; asthma, emphysema, pulmonary disease, or shortness of breath at 405; glaucoma at 407; a male over 40 years old with difficulty in urination at 410; or depression, anxiety, or seizures at 409.

Certain other conditions always result in 'no select' being included as a component medication regardless of the particular symptoms selected or component medications recommended. A 'no select' is included at 506 if the recommendation is for a female at 501 more than 12 years old at 502 who is either: pregnant or a nursing mother at 503; or less than 55 years old at 504 and taking a prescription medication other than birth control pills at 507. A 'no select' is included at 508 if the recommendation is for anyone taking a prescription medication at 505 who is not female at 501, or not more than 12 years old at 502, or more than 55 years old at 504.

The execution of the other knowledgebases is similar in that the customer's symptoms and general health are evaluated and a list of ingredients is added to a recommended ingredients list depending upon the customer's symptoms and health with a no-select condition indicated in the event that over the counter medications are not suitable based upon the customer's symptoms, general health or condition.

4. Select Product Recommendation

This routine takes the list of component medications generated by the execution of the knowledgebase and searches a database to find the appropriate product to be recommended. The products are classified by component medications, with the products to recommend within each classification selectable by pharmacy or management personnel without change to the system. Separate recommendations are recorded for different age groups as well.

The database files also control whether multiple-ingredient products can be recommended. If multiple-ingredient products are allowed, which is a function of the philosophy of the pharmacy or pharmacist, the system attempts to find a classification which matches as many of the recommended component medications as possible without including any component medications which are not included in the recommended list.

Therapeutic Class Numbers are used within the database files to identify the component medications present in a product. Each particular combination of component medications used, including the individual component medication as a single-ingredient product, is assigned a unique Therapeutic Class Number. Products present in the database files are classified by their associated Therapeutic Class Numbers, so that all products having some particular combination of component medications can be easily found by using the appropriate Therapeutic Class Number.

Each Therapeutic Class Number may have an associated qualifier code, which is used to indicate a subtype of a component medication. This allows the program to distinguish between medications which are functionally equivalent but differ in their usage criteria When multiple-product choices are available within a classification, the customer is asked to pick between the choices based on the different characteristics of the products. For example, if one possible product recommendation contains sugar and another does not, the customer will be asked if they prefer a medication containing sugar.

After selecting the first product to be recommended, the component medications present in this product are removed from the list of recommended component medications. If any component medications remain in the resulting list, another product is selected in the same way. This continues until each component medication recommended by the knowledgebase is present in one and only one recommended product.

A flowchart which may be used to implement the Select Product Recommendation routine is shown in FIGS. 3a-3d. First, if the recommended component medications list referred to herein as the recommended ingredients list generated by the execution of the knowledgebase includes 'antipyretic', it is replaced by 'analgesic' at 601, since the two types of ingredients are interchangeable for the range of products supported. If any duplications are present on the recommended ingredients list they are also eliminated at this point. A list of Therapeutic Class Numbers is then initialized by indicating that each has not yet been tried for product selection at 604.

A main program loop is then entered, which at the top level begins at 606. This loop is executed repeatedly until the recommended ingredients list is empty at 606. The first step in this loop is to select a Therapeutic Class Number to be used. This is done by a function call at 608, with details shown in FIGS. 3b and 3c and described below.

If the function call fails to find a usable Therapeutic Class Number at 609, an error indication is set to show that a recommended ingredient was not found at 612 and the first recommended ingredient is eliminated from the list at 615 before returning to the beginning of the main program loop. If the function call succeeds at 609, an indication is set that the Therapeutic Class Number selected has been tried at 602. A list of possible product selections with that Therapeutic Class Number is then generated. This is done by a second function call at 603, with details shown in of FIG. 3c and described below.

If the function call fails to find any usable products with the selected Therapeutic Class Number at 605, execution returns to the beginning of the main program loop. Otherwise, a secondary selection loop is entered that continues until only one product is left in the drug selection list at 607. If more than one product is present in the list, the first characteristic by which products in the list differ is found at 610 and the customer is asked to choose based on that characteristic at 611. For example, if the medication is available in both tablet and liquid form, the customer is asked which form is preferred. All products which do not match the customer preference are then eliminated from the list at 614 before returning to the start of the secondary selection loop.

Once the drug selection list has been reduced to a single choice at 607, the product remaining on the list is added to the recommended drug list at 613 and all component ingredients present in the product are eliminated from the recommended ingredients list at 616. Execution then returns to the start of the main program loop.

Figure 3A:
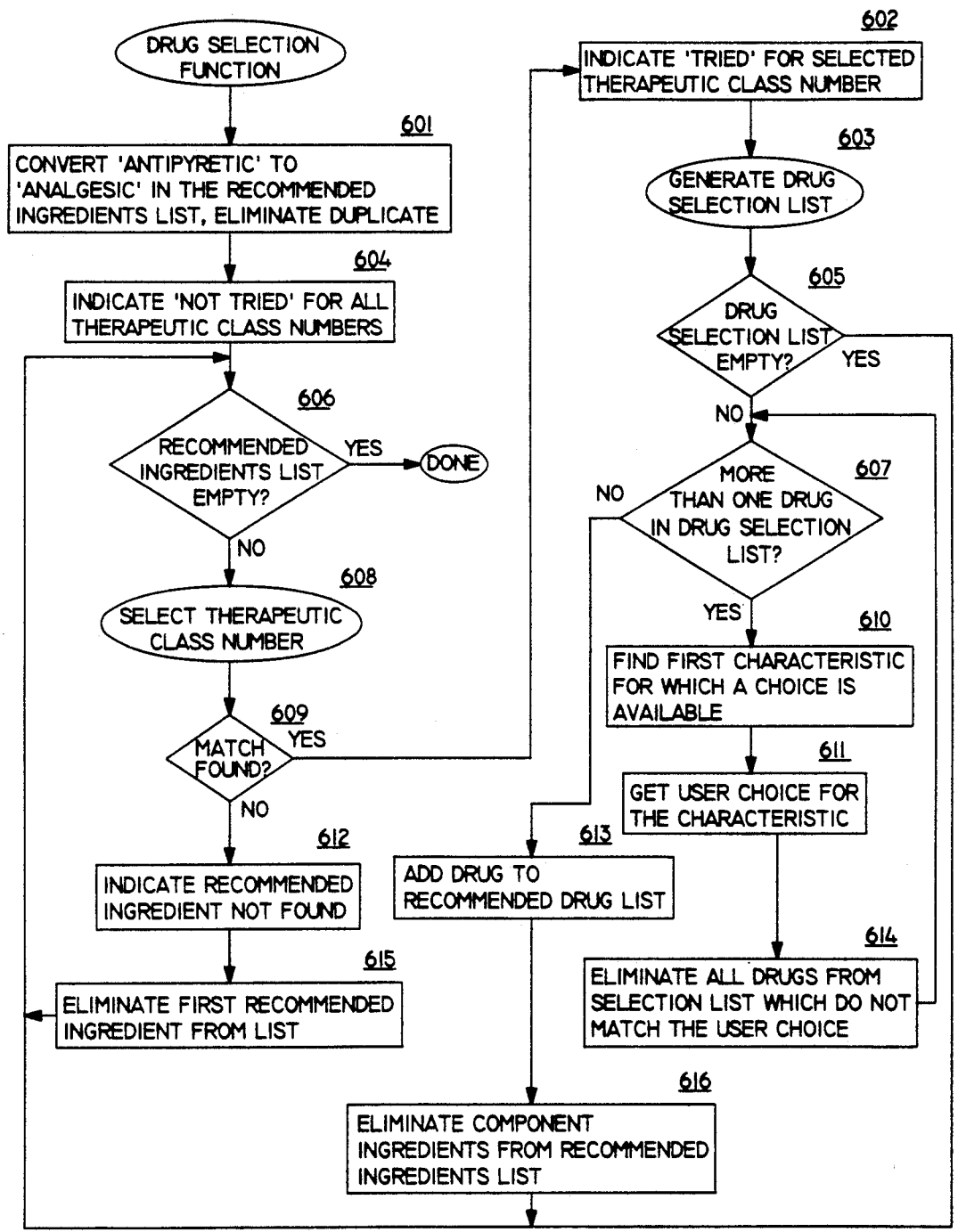
FIG. 3a-3d a flow chart of a program module which performs drug selection based on the output resulting from the execution of the knowledgebase.
Figure 3B:
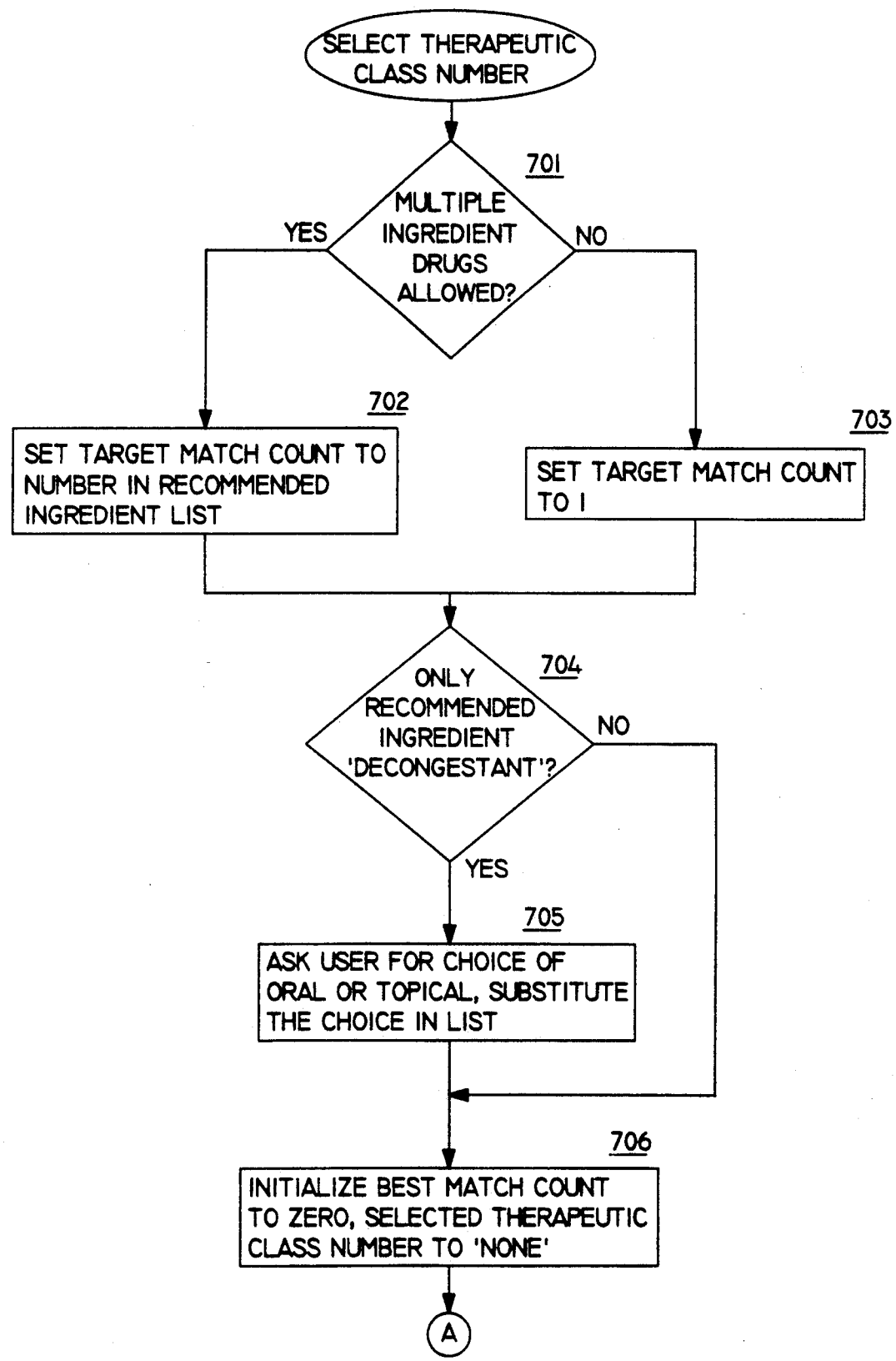
Figure 3C:
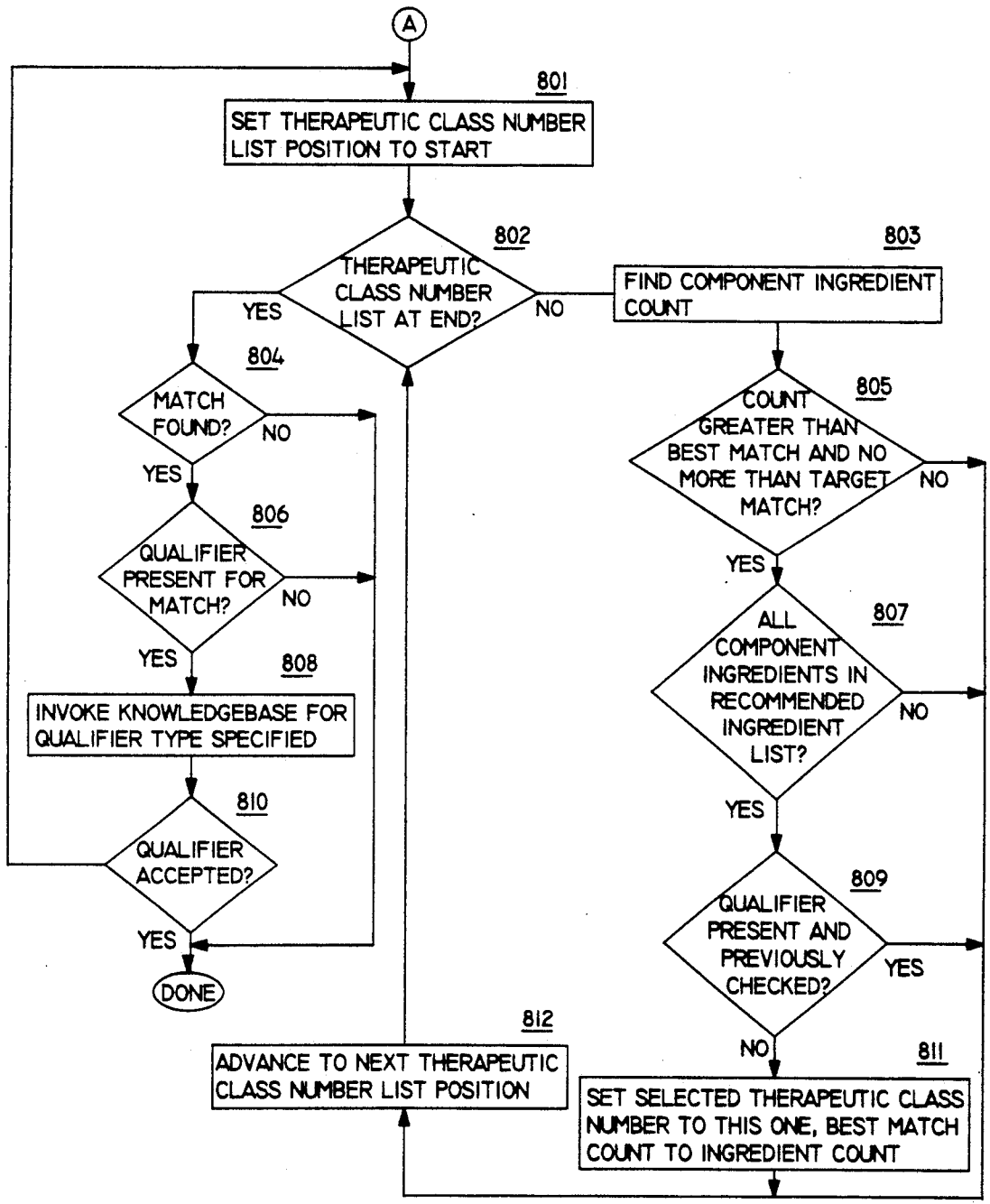

The Select Therapeutic Class Number function flow is shown in FIGS. 3b and 3c. This function first checks whether multiple ingredient drugs recommendations are allowed at 701, as determined by the pharmacist when setting up the system. If so, a target match count value is set to the total number of component medications in the recommended ingredients list at 702. This will cause the Therapeutic Class Number selection to include as many of these ingredients as possible. If multiple ingredient drug recommendations are not allowed at 701, the target match count value is set to 1 at 703 so that only the first component medication on the recommended ingredients list will be considered when selecting a Therapeutic Class Number.

Next a check is made for the case where the only recommended ingredient being considered is 'decongestant' at 704. If this case applies, the user is asked to choose between an oral and a topical decongestant, and the choice made is substituted for 'decongestant' in the recommended ingredients list at 705.

After this, the best match count found is set to 0 and the selected Therapeutic Class Number is set to 'none' at 706.

A loop is then entered to find the Therapeutic Class Number to be used. The first step in this loop sets the current position in the Therapeutic Class Number list to the start of the list 801. Within this main loop, an inner loop is then entered which continues until the end of the Therapeutic Class Number list is reached at 802.

The first step in this inner loop is to find the number of component ingredients for the current Therapeutic Class Number 803. If this count is greater than the best match count found previously, and less than or equal to the target match count 805, and each component ingredient for the current Therapeutic Class Number is one of the recommended ingredients being considered 807, and either there is no qualifier present for the current Therapeutic Class Number or the qualifier has not been checked previously 809, the selected Therapeutic Class Number is set to the current one in the list and the best match count found is set to the number of component ingredients 811. Whether these conditions succeed or fail, the current position in the Therapeutic Class Number list is advanced to the next in the list 812, and execution continues at the beginning of the inner loop.

When the end of the Therapeutic Class Number list is reached 802, the selected Therapeutic Class Number is checked before being returned to the caller. If a Therapeutic Class Number was selected at 804, and a qualifier code is present for the Therapeutic Class Number 806, the appropriate knowledgebase is invoked to check whether the qualifier code may be used 808. If no Therapeutic Class Number was selected 804, or no qualifier code is present for that Therapeutic Class Number 806, the result is returned directly.

A knowledgebase invoked to check the usability of a qualifier code may request any necessary information from the user in order to determine whether the qualifier is allowed. The only knowledgebase currently defined for checking qualifier codes is the MOD99 knowledgebase which is defined in Appendix 6. This knowledgebase checks the usability of various types of analgesics.

If the result of the knowledgebase invocation is to reject the qualifier specified for the selected Therapeutic class number 810, the main loop is restarted 801 to select another Therapeutic Class Number. If the qualifier is accepted 810, it is returned to the caller.

Figure 3D:
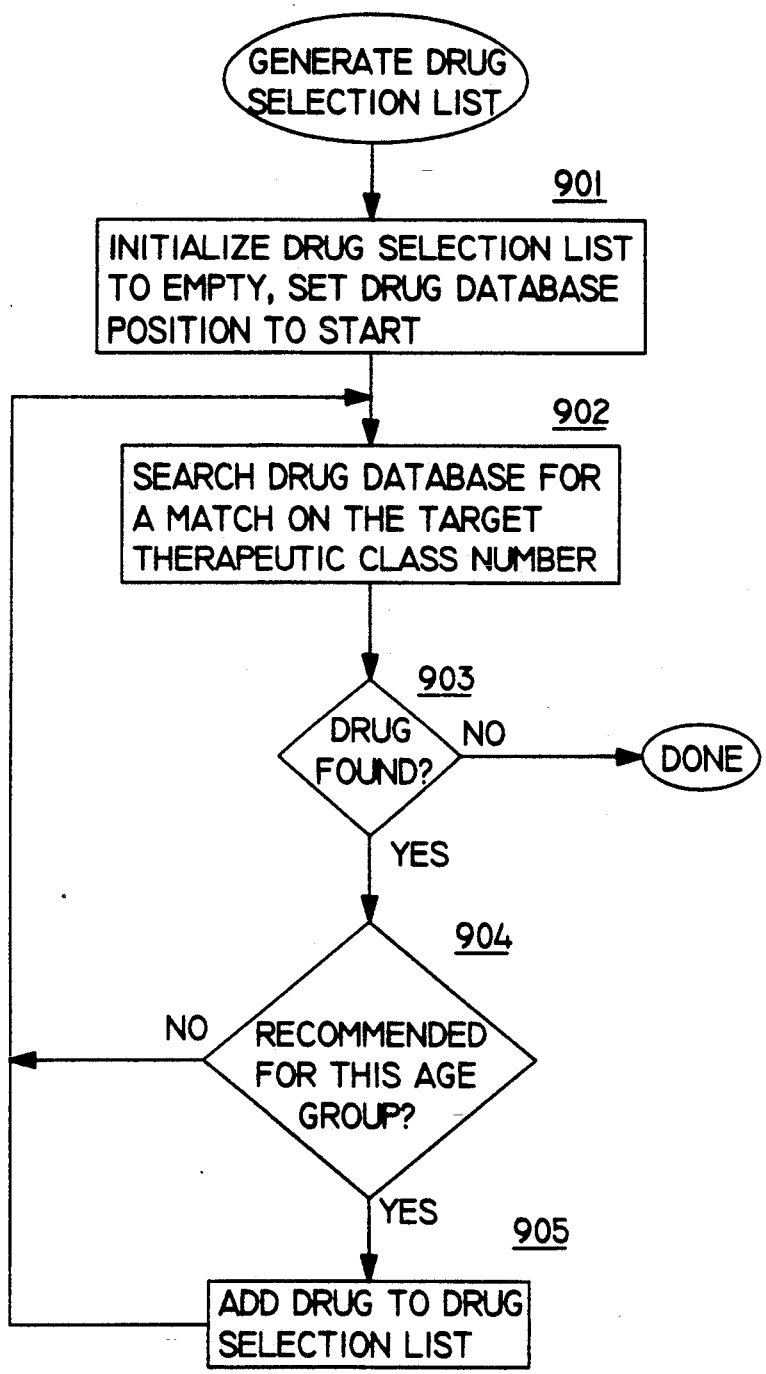

The Generate Drug Selection List function flow is shown in FIG. 3d. This function first initializes the drug selection list to empty and sets the current position in the drug database to the start at 901. It then begins a loop to generate the drug selection list. The first step in the loop is to search the drug database for the next drug with the selected Therapeutic Class Number at 902. If a drug is found at 903, it is then checked to determine if the pharmacist has selected this product for recommendation to the age range that includes this customer at 904. If the drug has been selected for recommendation, it is then added to the drug selection list at 905. Whether selected or not, execution then returns to the start of the loop. When no more drugs with the selected Therapeutic Class Number are found at 903, the generated drug selection list is returned to the caller.

Suitable software for implementing the Select Product Recommendation routine should be apparent to a person skilled in the art. One such suitable routine in C is attached hereto as Appendix 7.

5. Generate Session Report

The next routine generates a session report for the customer, which may be printed immediately or queued for later printing. This report includes a summary of the customer information provided to the system, along with a detailed list of the questions which have been asked by the system and the responses the customer made. If the knowledgebase found any potential problems with the customer using the recommended medications during the execution of the symptom knowledgebase, the report is prefaced with a header page to alert the pharmacist that a problem may exist. The relevant portions of the session summary are then printed differently to draw them to the pharmacist's attention.

The actual product recommendations follow the session summary. For each recommended product, the system prints the product name and a summary of usage information for the product. This information may include warnings and usage restrictions as well as actual directions for use. Other information, such as location in the store and price, may also be included. Coupons for purchasing the product at a discount may also be printed with the recommendation information.

Suitable software for implementing the Generate Session Report routine should be apparent to a person skilled in the art. One such suitable routine in C is attached hereto as Appendix 8.

6. Close Session

This routine asks the customer if they have another symptom for which they wish to consult the system. If the answer is "yes", the program returns to the Select Main Symptom step to select the new main symptom category. If the answer is "no" the customer is thanked for using the system and referred to the pharmacist to obtain the printed report.

Suitable software for implementing the Close Session routine should be apparent to a person skilled in the art. One such suitable routine in C is attached hereto as part of Appendix 1.

Various "#include" files used to generate the programs are provided in Appendix 9 as DATA.H, DEFS.H, SCREEN.H, VARS.H, and VERSION.H.

Figure 4:
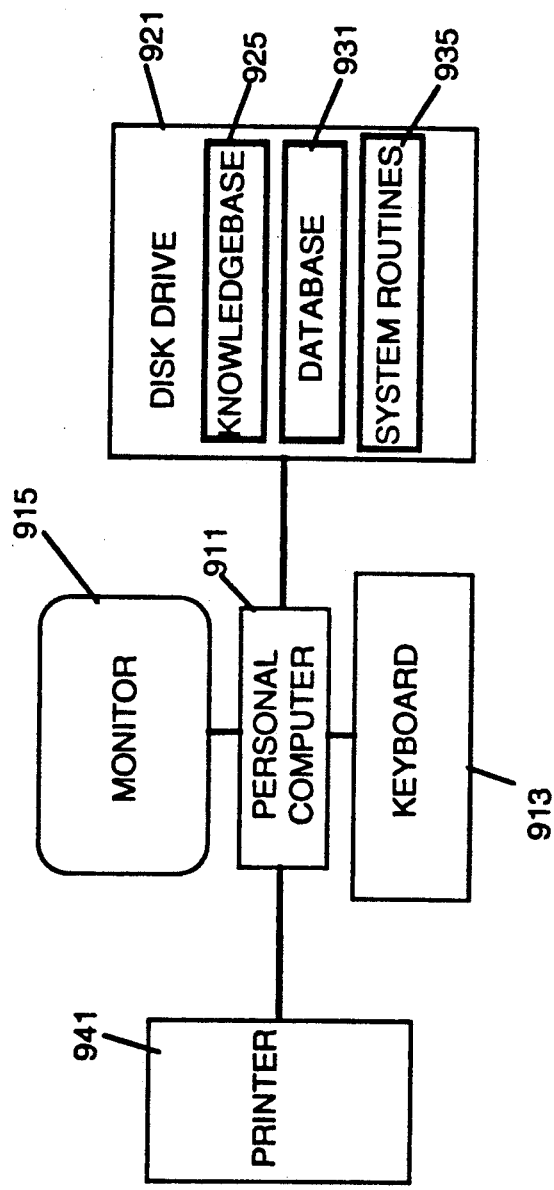
FIG. 4 is a block diagram showing the various hardware elements of the invented system.

FIG. 4 is a block diagram showing suitable hardware which may be utilized to implement the invented system. The system includes a personal computer 911 having a keyboard 913 for use data input, a monitor 915 to display the prompts and provide feedback to the user for data which is input, disk drive 921 on which are stored the various knowledge bases such as the cough and cold knowledgebase illustrated in FIG. 2a. database 931 utilized by the Select Product Recommendation routine and system routines 935 which are the various program modules labeled 1-6 in FIG. 1 as described above. Also shown in FIG. 4 is printer 941 onto which the session report generated by the Generate Session Report module may be printed. The various hardware elements 911, 913, 915, 921 and 941 are readily available components, the specifics of which are not important to an understanding of the invention. The knowledgebase 925, database 931 and system routines 935 contain information as described herein which is loaded into the memory of personal computer 911 for execution and to provide data used by the routines executed by personal computer 911.

APPENDIX 1

```
#include <graph.h>
#include <stdio.h>
#include <stdlib.h>
#include <string.h>
#include <time.h>
#include <sys\types.h>
#include <sys\timeb.h>
#include "d4base.h"

include <dos.h> include "data.h"
include "screen.h"
#include "defs.h"
#include "vars.h"

/*
    Print file information.
*/ static char ReportName [11] = "PRINTO.OUT";

static PrintPacket ReportInformation =
{
    0,
    ReportName
};

static char *ReportPacket = (char *) &ReportInformation + 1;

/*
    Screen data references.
*/ extern TextRec EnterNewText;            /* new user name input screen text */
extern TextRec NewPassText;             /* new user password input screen text */
extern GroupRec NewPassInputs;              /* group for password input */
extern TextRec EnterOldText;            /* old user input screen text */
extern GroupRec OldNameInputs;              /* group for name inputs */
extern TextRec NewBirthText;            /* new user birthdate input text */
extern InputRec YearNewInput;               /* birth year input item */
extern GroupRec NewInfoGroup;           /* new user confirmation screen */
extern TextRec ShowNameText;                /* name text string in screen */
extern TextRec ShowSexText;                 /* sex text string in screen */
extern TextRec DateBornText;                /* birthdate text string in screen */
extern TextRec BloodPressureText;       /* blood pressure input screen text */
extern GroupRec BloodPressureInputs;        /* group for blood pressure inputs */
extern TextRec HaveUsedText;            /* "Have you used..." screen text */
extern GroupRec LoadingKBScreen;        /* loading knowledgebase screen */
extern GroupRec WaitPrintingScreen;     /* waiting for printer screen */
extern GroupRec ThanksUsingScreen;      /* thanks for using screen */
extern GroupRec CantUseScreen;          /* can't use system screen */ if ! PROF_VERSION || INFO_VERSION extern GroupRec IntroInfoScreen;        /* introductory information screen */
extern GroupRec IntroErrorGroup;            /* introduction error display */ endif if ! PROF_VERSION extern TextRec MedAssistsText;          /* "MedScreen assists..." text */
extern TextRec PleaseReplyText;         /* "Please reply..." text */ endif extern GroupRec UserResponseGroup;      /* group of possible responses */
```

```c
/****************************************************************
  confirm_user Sets up and runs the user data confirmation screen, returning a TRUE if
    the user accepts the data, FALSE otherwise.
****************************************************************/ static bool confirm_user (void)
{
    char        date [8];

/* generate full user name string */
    strcpy (UserFullName, UserFirstName);
    strcat (UserFullName, " ");
    strcat (UserFullName, UserLastName);
    ShowNameText.Text = UserFullName;

/* set string value for sex */
    ShowSexText.Text = UserGender == 1 ? "Female" : "Male";

/* generate full user birthdate string */
    strcpy (date, UserMonthText);
    strcat (date, "/");
    strcat (date, UserYearText);
    DateBornText.Text = date;

/* force width calculations for centering strings */
    ShowNameText.Item.Bounds.Left = ShowNameText.Item.Bounds.Right = 0;
    ShowSexText.Item.Bounds.Left = ShowSexText.Item.Bounds.Right = 0;
    DateBornText.Item.Bounds.Left = DateBornText.Item.Bounds.Right = 0;

/* return the result of running the screen */
    return (bool)
      (run_template (300, (ItemPtr) &NewInfoGroup) == RESPONSE_YES);
}

/****************************************************************
  user_record

Retrieves the information for an existing user in the "USER" file.
****************************************************************/ static short user_record (char *last, char *first, char *pass)
{
    char        str [33];

/* generate the key value to be found */
    copy_fill (str, UserLastName, 15);
    copy_fill (str + 15, UserFirstName, 10);
    copy_fill (str + 25, UserPassword, 8);

/* try to find the corresponding record */
    d4select (UserDatabase);
    i4select (UserNameIndex);
    return (short) d4seek_str (str);
}

/****************************************************************
  get_user

Looks up the information for an old user in the "USER" file.
****************************************************************/ static bool get_user (void)
{
    short       code;

/* retrieve the user information */
    code = user_record (UserLastName, UserFirstName, UserPassword);
    if (! code)
    {
        char        *txt;

/* set the gender code */
        UserGender = f4char (User_Gender) == 'F' ? 1 : 2;

/* retrieve birthdate information */
        txt = f4str (User_BirthDate);
        copy_trunc (UserYearText, txt, 4);
        copy_trunc (UserMonthText, txt + 4, 2);

/* set the user identifier number */
        CurrentUserID = atol (f4str (User_UserID));

/* take return for information found */
        return TRUE;
    }
```

```c
        /* record not found in file */
        return FALSE;
}

/****************************************************************
   user_access Updates the last access date and blood pressure (if it has been input)
        in user information, converting to the internal date format.
****************************************************************/ static bool user_access (char *date)
{
    short      code;

/* reformat the date value supplied */
    strcpy (UserAccess, date [6] == '9' ? "19" : "20");
    memcpy (UserAccess + 2, date + 6, 2);
    memcpy (UserAccess + 4, date, 2);
    memcpy (UserAccess + 6, date + 3, 2);
    UserAccess [8] = 0;

/* retrieve the user information */
    code = user_record (UserLastName, UserFirstName, UserPassword);
    if (! code)
    {
        /* replace the last access date field */
        f4r_str (User_LastAccess, UserAccess);

/* check for blood pressure input */
        if (UserTopPressure [0] && UserBottomPressure [0])
        {

/* replace blood pressure information */
            f4r_str (User_BloodP1, UserTopPressure);
            f4r_str (User_BloodP2, UserBottomPressure);
            f4r_str (User_BPDate, UserAccess);
        }

/* write out the modified record */
        d4write (d4recno ());

/* take successful completion return */
        return TRUE;
    }

/* record not found in file */
    return FALSE;
}

/****************************************************************
   new_user

Inputs the information for a new user.
****************************************************************/ static bool new_user (void)
{
    short      code;

/* initialize strings for a new user */
    strcpy (UserYearText, "19");
    UserMonthText [0] = 0;

/* ask the user to input the birth information */
    code = run_template (300, (ItemPtr) &NewBirthText);
    if (code >= 0)
    {

/* make sure two month digits present */
        if (UserMonthText [1] == 0)
        {
            UserMonthText [2] = 0;
            UserMonthText [1] = UserMonthText [0];
            UserMonthText [0] = '0';
        }

/* take successful completion return */
        return TRUE;
    }

/* take failure return */
    return FALSE;
}
```

```c
/****************************************************************
   add_user Adds the information for a new user to the "USER" file.
****************************************************************/ static bool add_user (void)
{
    char        buf [11];
    int         code;

/* set the user ID value in record */
    d4select (UserDatabase);
    CurrentUserID = ++LastUserID;
    sprintf (buf, "%010ld", CurrentUserID);
    f4r_str (User_UserID, buf);

/* set the name and sex fields */
    f4r_str (User_Lname, UserLastName);
    f4r_str (User_Fname, UserFirstName);
    f4r_str (User_Gender, UserGender == 1 ? "F" : "M");

/* generate birthdate field value */
    strcpy (buf, UserYearText);
    strcat (buf, UserMonthText);
    strcat (buf, "01");
    f4r_str (User_BirthDate, buf);

/* set the password defined by user */
    f4r_str (User_Password, UserPassword);

/* add the new user record */
    code = d4append ();
    return (bool) (code == 0);
}

/****************************************************************
   set_serial

Sets the serial number to be used for a user consultation.  This is
     generated from the date and time the user picks the type of problem
     involved.
****************************************************************/ static void set_serial (char *serial)
{
    char        buf [9];

/* format year into leading positions */
    _strdate (buf);
    if (buf [6] >= '8')
    {
        serial [0] = '1';
        serial [1] = '9';
    }
    else
    {
        serial [0] = '2';
        serial [1] = '0';
    }
    serial [2] = buf [6];
    serial [3] = buf [7];

/* format month and day following */
    serial [4] = buf [0];
    serial [5] = buf [1];
    serial [6] = buf [3];
    serial [7] = buf [4];

/* mark division between date and time */
    serial [8] = '.';

/* format time into trailing positions */
    _strtime (buf);
    serial [9]  = buf [0];
    serial [10] = buf [1];
    serial [11] = buf [3];
    serial [12] = buf [4];
    serial [13] = buf [6];
    serial [14] = buf [7];
} if ! PROF_VERSION || INFO_VERSION

/****************************************************************
   information_screen
```

```
    Displays an information screen for the user, waiting the specified
    number of seconds for the user to read the screen and press a key to
    continue.
****************************************************************/ bool information_screen (short time, ItemPtr item)
{
    RectRec    rect;
    int        code;

/* initialize the screen display */
    IntroInfoScreen.Child = item;
    link_item ((ItemPtr) &IntroInfoScreen);
    draw_item ((ItemPtr) &IntroInfoScreen);

/* check user response */
    while (! wait_key (time * 10))
    {

/* display error message warning of termination */
        IntroInfoScreen.Child = (ItemPtr) &IntroErrorGroup;
        link_item ((ItemPtr) &IntroInfoScreen);
        draw_item ((ItemPtr) &IntroErrorGroup);

/* wait for user input or timeout */
        if (wait_key (150))
            code = 0;
        else
            code = -1;

/* restore the original display */
        item_rectangle ((ItemPtr) &IntroErrorGroup, &rect);
        IntroInfoScreen.Child = item;
        push_clip (&rect);
        draw_item ((ItemPtr) &IntroInfoScreen);
        pop_clip ();

/* exit if user did not respond */
        if (code < 0)
            return FALSE;
    }

/* take successful completion return */
    return TRUE;
} endif

/****************************************************************
  query_user

Handles the actual user consultation loop, asking the user a series of
    questions and loading in the appropriate knowledgebase, then invoking
    inference on the knowledgebase.
****************************************************************/
short query_user (void)
{
    char        text [11];
    char        *choices [4];
    union REGS  regs;
    struct SREGS    segs;
    int         index;
    int         high;
    int         low;
    int         num;
    short       code;
    bool        adding;

#if ! PROF_VERSION

/* run the information screens */
    if (! information_screen (15, (ItemPtr) &MedAssistsText) ||
        ! information_screen (15, (ItemPtr) &PleaseReplyText))
        return -1;

#endif

/* wait for the printer to be available */
    if (! wait_printer ())
        return -1;

/* set up the template screen */
    init_template ();

/* loop until questions completed or aborted */
    while (TRUE)
    {
```

```
                /* find out if this is a new user */
                code = run_template (300, (ItemPtr) &HaveUsedText);
                adding = FALSE;
                if (code >= 0)
                {

/* initialize the name and password information */
                    UserFirstName [0] = 0;
                    UserLastName [0] = 0;
                    UserPassword [0] = 0;

/* check response to new user question */
                    if (code == RESPONSE_YES)
                    {

/* input information from a repeat user */
                        code = run_template (300, (ItemPtr) &EnterOldText);
                        if (code >= 0)
                        {

/* retrieve the user information */
                            if (! get_user ())
                            {

/* report information not found */
                                run_error (TRUE, 300, (ItemPtr) &OldNameInputs,
#if PROF_VERSION
                                    "No match is present for the name and password "
                                    "you typed in.  Please reenter the patient name "
                                    "and password, or type \"-\" to cancel and begin "
                                    "again as a new patient.");
#else
                                    "No match is present for the name and password "
                                    "you typed in.  Please reenter your name and "
                                    "password, or type \"-\" to cancel and begin "
                                    "again as a new user.");
endif /* retry password entry */
                                UserFirstName [0] = 0;
                                UserLastName [0] = 0;
                                UserPassword [0] = 0;
                                code = run_template (300, (ItemPtr) &EnterOldText);
                                if (code >= 0 && ! get_user ())
                                {

/* fail this time on not found */
                                    run_error (TRUE, 300, (ItemPtr) &OldNameInputs,
#if PROF_VERSION
                                        "No match is present for the name and password "
                                        "you typed in.  Please begin again as a new "
                                        "patient.");
#else
                                        "No match is present for the name and password "
                                        "you typed in.  Please begin again as a new "
                                        "user.");
#endif
                                    continue;
                                }
                            }

/* check for special handling required */
                            if (CurrentUserID == 1001)
                            {

/* terminate program execution */
                                ExitFlag = TRUE;
                                return -1;
                            }
if ! DEMO_VERSION
                            else if (CurrentUserID == 1002)
                            {

/* list all reports still around */
                                index = PrintNum;
                                num = 0;
                                do {
                                    if (PrintName [index] [0])
                                    {
                                        PrintName [index] [2] = (char) ('1' + num);
                                        choices [num++] = PrintName [index];
                                    }
                                    index = (index + 1) & 3;
                                } while (index != PrintNum);

/* find the report number to be reprinted */
                                if (num > 0)
                                {
```

```
                    code = pick_list (
                        "Select the report to be reprinted from the "
                        "list of names below.", 24, num, choices);
                    if (code >= 0)
                    {
                        /* set the report file name */
                        ReportName [5] = (char) ('0' + code);

/* requeue the report file for printing */
                        regs.h.ah = 1;
                        regs.h.al = 1;
                        segs.ds = FP_SEG (ReportPacket);
                        regs.x.dx = FP_OFF (ReportPacket);
                        int86x (0x2F, ®s, ®s, &segs);
                    }
                }
                else
                {
                    /* fail on report not available */
                    run_error (TRUE, 300, (ItemPtr) &OldNameInputs,
                        "No report is available for reprinting.");
                }

/* exit the user input loop */
                break;
            } endif

}
    }
    else
    {
        /* input new user name and gender information */
        adding = TRUE;
        UserGender = run_template (300, (ItemPtr) &EnterNewText);
        if (UserGender > 0)
        {
            /* input new user password and birthdata */
            while (code >= 0)
            {
                /* find choice of user password */
                code = run_template (300, (ItemPtr) &NewPassText);
                if (code >= 0)
                {
                    /* check for duplicate name and password */
                    if (get_user ())
                    {
                        /* display the error message */
                        run_error (TRUE, 300,
                            (ItemPtr) &NewPassInputs,
                            "The password you typed in cannot be used."
                            "\nPlease enter a different password.");
                        UserPassword [0] = 0;
                    }
                    else
                    {
                        /* get the user birth information */
                        if (new_user ())
                            break;
                        code = -1;
                    }
                }
            }
        }
        else
            code = -1;
    }

/* check completion status of basic user information */
    if (code >= 0)
    {
        /* let the user confirm what we know */
        if (confirm_user ())
        {
            /* retrieve the current date */
            _strdate (text);
```

```c
            /* find years of age */
            UserAge = atoi (text + 6) - atoi (UserYearText + 2);
            if (UserAge < 0)
                UserAge += 100;

/* adjust for month not yet reached */
            text [2] = 0;
            if (atoi (text) < atoi (UserMonthText))
                --UserAge;

/* check for too young */
            if (UserAge < 3)
            {

/* report unable to use the system */
                link_item ((ItemPtr) &CantUseScreen);
                draw_item ((ItemPtr) &CantUseScreen);

/* wait a while with screen displayed */
                wait_key (60);
                break;
            }

/* add new user to database */
            if (adding)
                add_user ();

/* add user name to logo area */
            _setviewport (0, 0, SCREEN_WIDTH, SCREEN_HEIGHT);
            _clearscreen (_GCLEARSCREEN);
            display_logos (0, LOGO_HEIGHT, "MedScreen", UserFullName);
            _setviewport
                (0, LOGO_HEIGHT, SCREEN_WIDTH, SCREEN_HEIGHT);

/* check for blood pressure known */
            init_template ();
            UserTopPressure [0] = 0;
            UserBottomPressure [0] = 0;
            UserHighPressure = FALSE;
#if PROF_VERSION
            code = ask_noyes (11, "Do you have a recent blood "
                "pressure reading for the patient?");
#else
            code = ask_noyes (11, "Do you know your recent blood "
                "pressure levels?");
endif /* get the blood pressure reading */
            if (code > 0)
                while (TRUE)
                {

/* request user input for blood pressure */
                    code = run_template (300, (ItemPtr)
                        &BloodPressureText);
                    if (code >= 0)
                    {

/* check the values input */
                        high = atoi (UserTopPressure);
                        low = atoi (UserBottomPressure);
                        if (high <= low)
                        {

/* report error in values */
                            run_error (TRUE, 300,
                                (ItemPtr) &BloodPressureInputs,
                                "Your first pressure measurement must "
                                "be higher than your second "
                                "measurement.\nPlease try again.");
                            UserTopPressure [0] = 0;
                            UserBottomPressure [0] = 0;

}
                        else
                        {

/* test for high blood pressure condition */
                            if (high >= 150 || low >= 90)
                                UserHighPressure = TRUE;
                            break;

}
                    }
                    else
                    {

/* discard any input values */
                        UserTopPressure [0] = 0;
```

```
                    UserBottomPressure [0] = 0;
                    code = 0;
                    break;
                }
            }

/* retrieve the current date */
            _strdate (text);

/* set last access data for user */
            user_access (text);

/* discard the old report file */
            if (DumpPrinter)
            {
                ReportName [5] = (char) ('0' + PrintNum);
                freopen (ReportName, "w", stdprn);
            }

/* initialize for sesson loop */
            HavePrinted = FALSE;
            while (code >= 0)
            {
if DEMO_VERSION while ((code = pick_list
                    ("What type of symptom do you have?", 9, KBCount,
                    KBSelects)) >= 0 && KBMapping [code] != 0)
                    run_error (TRUE, 300,
                        (ItemPtr) &UserResponseGroup,
                        "The symptom you have selected is not enabled "
                        "in the demonstration program.  Please choose "
                        "\"Cough & Cold\".");

else if PROF_VERSION code = pick_list
                    ("What type of symptom does the patient have?",
                    9, KBCount, KBSelects);

else code = pick_list ("What type of symptom do you have?",
                    9, KBCount, KBSelects);

#endif
endif if (code >= 0)
                {

/* form the serial number to be used */
                    set_serial (SessionSerial);

/* tell the user we're loading questionaire */
                    link_item ((ItemPtr) &LoadingKBScreen);
                    draw_item ((ItemPtr) &LoadingKBScreen);

/* initialize for the session */
                    ModuleNumber = KBMapping [code];
                    QueryCount = 0;
                    for (index = 0; index < DRUG_CHOICES; index++)
                        QualifiersPicked [index] = -1;

/* do the actual inference processing */
                    invoke_inference (ModuleNumber);

/* check for another problem */
#if PROF_VERSION
                    code = ask_noyes (11, "Does the patient have "
                        "another symptom you wish to consult "
                        "\037\003MedScreen\037\005 about?") - 1;
#else
                    code = ask_noyes (11, "Do you have another "
                        "symptom you wish to consult "
                        "\037\003MedScreen\037\005 about?") - 1;
#endif
                }
            }

/* handle customer report printing */
            if (HavePrinted && ! ScreenFlag)
            {

/* check for actual printer output */
                if (! DEMO_VERSION && DumpPrinter)
                {
```

```
            /* close the generated report file */
            fclose (stdprn);

/* set the report file name */
            ReportName [5] = (char) ('0' + PrintNum);
            strcpy (PrintName [PrintNum],
                "\037\0010\037\005\036");
            strcpy (PrintName [PrintNum] + 6, UserFullName);
            PrintNum = (char) ((PrintNum + 1) & 3);

/* queue the report for printing */
            regs.h.ah = 1;
            regs.h.al = 1;
            segs.ds = FP_SEG (ReportPacket);
            regs.x.dx = FP_OFF (ReportPacket);
            int86x (0x2F, ®s, ®s, &segs);
         }

/* thank the customer for using us */
         Link_item ((ItemPtr) &ThanksUsingScreen);
         draw_item ((ItemPtr) &ThanksUsingScreen);

/* wait a while with screen displayed */
         wait_key (60);
      }
   }
   else
   {
      /* loop again to correct invalid information */
      continue;
   }
  }
 }

/* exit the loop in normal operation */
 break;
}

/* return the final completion code */
return code;
}
```

APPENDIX 2

* R U L E S * of E:\MEDSCR\KB\MOD10A.KB ***

RULE #1 priority 95 - main symptom- possible
IF -----------------------------
    (1)    the main symptom is objectname(<symptom>) [threshold 0.20]
THEN -----------------------------
    (1)    level 1 drug class is <symptom | drug class> [certainty 1.00]

RULE #10 priority 90 - level 1 antipyretic to rec
IF -----------------------------
    (1)    the level 1 drug class is antipyretic [threshold 0.20]
THEN -----------------------------
    (1)    recommended drug class is antipyretic [certainty 1.00]

RULE #11 priority 90 - level 1 antihist to rec
IF -----------------------------
    (1)    the level 1 drug class is antihistamine [threshold 0.20]
THEN -----------------------------
    (1)    recommended drug class is antihistamine [certainty 1.00]

RULE #12 priority 90 - level 1 expect to rec
IF -----------------------------
    (1)    the level 1 drug class is expectorant [threshold 0.20]
THEN -----------------------------
    (1)    recommended drug class is expectorant [certainty 1.00]

RULE #13 priority 90 - level 1 antituss to rec
IF -----------------------------
    (1)    the level 1 drug class is antitussive [threshold 0.20]
THEN -----------------------------
    (1)    recommended drug class is antitussive [certainty 1.00]

RULE #14 priority 90 - level 1 analgesic to rec
IF -----------------------------
    (1)    the level 1 drug class is analgesic [threshold 0.20]
THEN -----------------------------
    (1)    recommended drug class is analgesic [certainty 1.00]

RULE #15 priority 90 - level 1 oral anesthetic to rec
IF -----------------------------
    (1)    the level 1 drug class is "oral anesthetic" [threshold 0.20]
THEN -----------------------------
    (1)    recommended drug class is "oral anesthetic" [certainty 1.00]

```
RULE #100 priority 88 - antihistamine to no select (special check on symptom)
    IF -------------------------------
        (1)    the level 1 drug class is antihistamine [threshold 0.20]
        (2) and the main symptom is "Runny nose" [threshold 0.20]
        (3) and the Runny nose duration > 6 [threshold 0.20]
        (4) or  the level 1 drug class is antihistamine [threshold 0.20]
        (5) and the customer age > 68 [threshold 0.20]
        (6) or  the level 1 drug class is antihistamine [threshold 0.20]
        (7) and the customer AC1 is yes [threshold 0.20]
        (8) or  the level 1 drug class is antihistamine [threshold 0.20]
        (9) and the customer glaucoma is yes [threshold 0.20]
        (10) or  the level 1 drug class is antihistamine [threshold 0.20]
        (11) and the customer AC5 is yes [threshold 0.20]
        (12) or  the level 1 drug class is antihistamine [threshold 0.20]
        (13) and the customer CC2 is yes [threshold 0.20]
    THEN ---------------------------
        (1)    recommended drug class is "no select" [certainty 1.00]

RULE #101 priority 89 - antitussive to no select
    IF -------------------------------
        (1)    the level 1 drug class is antitussive [threshold 0.20]
        (2) and the customer AC1 is yes [threshold 0.20]
        (3) or  the level 1 drug class is antitussive [threshold 0.20]
        (4) and the customer AC2 is yes [threshold 0.20]
        (5) or  the level 1 drug class is antitussive [threshold 0.20]
        (6) and the customer AC5 is yes [threshold 0.20]
    THEN ---------------------------
        (1)    recommended drug class is "no select" [certainty 1.00]

RULE #102 priority 87 - decongestant to no select
    IF -------------------------------
        (1)    the level 1 drug class is decongestant [threshold 0.20]
        (2) and the Stuffy nose duration > 6 [threshold 0.20]
    THEN ---------------------------
        (1)    recommended drug class is "no select" [certainty 1.00]

RULE #103 priority 89 - expectorant to no select
    IF -------------------------------
        (1)    the level 1 drug class is expectorant [threshold 0.20]
        (2) and the customer AC1 is yes [threshold 0.20]
        (3) or  the level 1 drug class is expectorant [threshold 0.20]
        (4) and the customer AC2 is yes [threshold 0.20]
        (5) or  the level 1 drug class is expectorant [threshold 0.20]
        (6) and the customer coughing up excess phlegm is yes [threshold 0.20]
    THEN ---------------------------
        (1)    recommended drug class is "no select" [certainty 1.00]

RULE #104 priority 86 - antipyretic to no select
    IF -------------------------------
        (1)    the level 1 drug class is antipyretic [threshold 0.20]
        (2) and the Fever duration > 3 [threshold 0.20]
        (3) or  the level 1 drug class is antipyretic [threshold 0.20]
        (4) and the Fever level > 100 [threshold 0.20]
    THEN ---------------------------
        (1)    recommended drug class is "no select" [certainty 1.00]

RULE #105 priority 85 - analgesic to no select
    IF -------------------------------
        (1)    the level 1 drug class is analgesic [threshold 0.20]
        (2) and the General Achiness duration > 6 [threshold 0.20]
    THEN ---------------------------
        (1)    recommended drug class is "no select" [certainty 1.00]

RULE #106 priority 84 - oral anesthetic to no select
    IF -------------------------------
        (1)    the level 1 drug class is "oral anesthetic" [threshold 0.20]
        (2) and the Sore throat duration >= 3 [threshold 0.20]
    THEN ---------------------------
        (1)    recommended drug class is "no select" [certainty 1.00]

RULE #107 priority 89 - coughmed to no select
    IF -------------------------------
        (1)    the level 1 drug class is coughmed [threshold 0.20]
        (2) and the Cough duration > 6 [threshold 0.20]
        (3) or  the level 1 drug class is coughmed [threshold 0.20]
        (4) and the customer chest pain is yes [threshold 0.20]
    THEN ---------------------------
        (1)    recommended drug class is "no select" [certainty 1.00]

RULE #200 priority 87 - level 1 decon w no spray to recommend
    IF -------------------------------
        (1)    the level 1 drug class is decongestant [threshold 0.20]
        (2) and the customer other medication use is yes [threshold 0.20]
        (3) and the customer nasal spray use is no [threshold 0.20]
    THEN ---------------------------
        (1)    recommended drug class is "decongestant topical" [certainty 1.00]

RULE #201 priority 87 - level 1 decon w spray to recommend
```

```
IF --------------------------
     (1)     the level 1 drug class is decongestant [threshold 0.20]
     (2) and the customer other medication use is yes [threshold 0.20]
     (3) and the customer nasal spray use is yes [threshold 0.20]
THEN ------------------------
     (1)     recommended drug class is "Nasal Spray NaCl" [certainty 1.00]

RULE #220 priority 87 - level 1 decon no other drug to recommend
IF ---------------------------
     (1)     the level 1 drug class is decongestant [threshold 0.20]
     (2) and the customer CC1 is no [threshold 0.20]
     (3) and the customer CC2 is no [threshold 0.20]
     (4) and the customer AC5 is no [threshold 0.20]
     (5) and the customer other medication use is no [threshold 0.20]
THEN ------------------------
     (1)     recommended drug class is decongestant [certainty 1.00]

RULE #221 priority 87 - CC1/CC2/AC5 yes level 1 decon w no other to rec spray
IF ---------------------------
     (1)     the level 1 drug class is decongestant [threshold 0.20]
     (2) and the customer CC1 is yes [threshold 0.20]
     (3) and the customer other medication use is no [threshold 0.20]
     (4) or  the level 1 drug class is decongestant [threshold 0.20]
     (5) and the customer CC2 is yes [threshold 0.20]
     (6) and the customer other medication use is no [threshold 0.20]
     (7) or  the level 1 drug class is decongestant [threshold 0.20]
     (8) and the customer AC5 is yes [threshold 0.20]
     (9) and the customer other medication use is no [threshold 0.20]
THEN ------------------------
     (1)     recommended drug class is "decongestant topical" [certainty 1.00]

RULE #300 priority 89 - Level 1 coughmed to expectorant
IF ---------------------------
     (1)     the level 1 drug class is coughmed [threshold 0.20]
     (2) and the customer chest congestion or coughing up phlegm is yes [threshol
d 0.20]
THEN ------------------------
     (1)     level 1 drug class is expectorant [certainty 1.00]

RULE #301 priority 89 - Level 1 coughmed to antitussive
IF ---------------------------
     (1)     the level 1 drug class is coughmed [threshold 0.20]
     (2) and the customer chest congestion or coughing up phlegm is no [threshold
 0.20]
     (3) or  the level 1 drug class is coughmed [threshold 0.20]
     (4) and the customer chest congestion or coughing up phlegm is yes [threshol
d 0.20]
     (5) and the customer excessive coughing is yes [threshold 0.20]
THEN ------------------------
     (1)     level 1 drug class is antitussive [certainty 1.00]

RULE #302 priority 89 - Level 1 coughmed adding antihistamine
IF ---------------------------
     (1)     the level 1 drug class is coughmed [threshold 0.20]
     (2) and the customer coughing in bed is yes [threshold 0.20]
THEN ------------------------
     (1)     level 1 drug class is antihistamine [certainty 1.00]

RULE #800 priority 90 - AC1
IF ---------------------------
     (1)     the customer Asthma, Emphysema, Chronic Pulmonary Disease, or Short
ness of Breath is yes [threshold 0.20]
THEN ------------------------
     (1)     customer AC1 is yes [certainty 1.00]
ELSE ------------------------
     (1)     customer AC1 is no [certainty 1.00]

RULE #802 priority 90 - AC2
IF ---------------------------
     (1)     the customer Smoking is yes [threshold 0.20]
THEN ------------------------
     (1)     customer AC2 is yes [certainty 1.00]
ELSE ------------------------
     (1)     customer AC2 is no [certainty 1.00]

RULE #820 priority 90 - CC1
IF ---------------------------
     (1)     the customer Heart condition, Thyroid Condition, Blood Pressure, or
Diabetes is yes [threshold 0.20]
THEN ------------------------
     (1)     customer CC1 is yes [certainty 1.00]
ELSE ------------------------
     (1)     customer CC1 is no [certainty 1.00]

RULE #822 priority 90 - CC2
IF ---------------------------
     (1)     the customer Depression, Anxiety, or Seizures is yes [threshold 0.2
0]
THEN ------------------------
```

```
      (1)     customer CC2 is yes [certainty 1.00]
   ELSE --------------------------
      (1)     customer CC2 is no [certainty 1.00]

RULE #860 priority 90 - Fem1
   IF --------------------------
      (1)      the customer gender is female [threshold 0.20]
      (2) and the customer age > 12 [threshold 0.20]
      (3) and the customer pregnancy and nursing mother is yes [threshold 0.20]
   THEN --------------------------
      (1)     customer Fem1 is yes [certainty 1.00]
   ELSE --------------------------
      (1)     customer Fem1 is no [certainty 1.00]

RULE #865 priority 90 - AC5
   IF --------------------------
      (1)      the customer gender is male [threshold 0.20]
      (2) and the customer age > 40 [threshold 0.20]
      (3) and the customer difficulty in urination is yes [threshold 0.20]
   THEN --------------------------
      (1)     customer AC5 is yes [certainty 1.00]
   ELSE --------------------------
      (1)     customer AC5 is no [certainty 1.00]

RULE #900 priority 50 - general no select
   IF --------------------------
      (1)      the customer Fem1 is yes [threshold 0.20]
      (2) or  the customer gender is female [threshold 0.20]
      (3) and the customer age >= 13 [threshold 0.20]
      (4) and the customer age < 55 [threshold 0.20]
      (5) and the customer prescription not birth control is yes [threshold 0.20]
      (6) or  the customer gender is male [threshold 0.20]
      (7) and the customer use of prescription medication is yes [threshold 0.20]
      (8) or  the customer age < 13 [threshold 0.20]
      (9) and the customer use of prescription medication is yes [threshold 0.20]
      (10) or  the customer age >= 55 [threshold 0.20]
      (11) and the customer use of prescription medication is yes [threshold 0.20]

THEN --------------------------
      (1)     recommended drug class is "no select" [certainty 1.00]

* * *   R U L E S   * * *   of   E:\MEDSCR\KB\MOD10A.KB      * * *
```

APPENDIX 3

```
   * * *   R U L E S   * * *   of   E:\MEDSCR\MAHOGANY\MOD11B.KB   * * *

RULE #50 priority 90 - external analgesic possible
   IF --------------------------
      (1)      the main symptom is any(Backache,"Muscle Pain","Joint Pain","Arthritis Pain") [threshold 0.20]
   THEN --------------------------
      (1)     recommended choice is yes [certainty 1.00]
   ELSE --------------------------
      (1)     recommended choice is no [certainty 1.00]

RULE #51 priority 50 - cream/ointment suggestion
   IF --------------------------
      (1)      the main symptom is "Arthritis Pain" [threshold 0.20]
      (2) and the doctor's suggestion is "Cream/Ointment" [threshold 0.20]
   THEN --------------------------
      (1)     customer preference is "Cream/Ointment" [certainty 1.00]

RULE #52 priority 50 - tablet/capsule suggestion
   IF --------------------------
      (1)      the main symptom is "Arthritis Pain" [threshold 0.20]
      (2) and the doctor's suggestion is "Tablet/Capsule" [threshold 0.20]
   THEN --------------------------
      (1)     customer preference is "Tablet/Capsule" [certainty 1.00]

RULE #53 priority 50 - cream/ointment preference
   IF --------------------------
      (1)      the recommended choice is yes [threshold 0.20]
      (2) and the customer preference is "Cream/Ointment" [threshold 0.20]
   THEN --------------------------
      (1)     recommended drug class is "external analgesic" [certainty 1.00]

RULE #54 priority 50 - tablet/capsule preference
   IF --------------------------
      (1)      the recommended choice is yes [threshold 0.20]
      (2) and the customer preference is "Tablet/Capsule" [threshold 0.20]
   THEN --------------------------
      (1)     recommended drug class is Analgesic [certainty 1.00]

RULE #60 priority 90 - plain analgesic
   IF --------------------------
      (1)      the main symptom is any(Headache,Toothache) [threshold 0.20]
      (2) or  the main symptom is "Menstrual Pain" [threshold 0.20]
      (3) and the customer gender is female [threshold 0.20]
```

```
THEN --------------------------------
    (1)     recommended drug class is Analgesic [certainty 1.00]

RULE #127 priority 60 - Fem1
IF --------------------------------
    (1)     the customer gender is female [threshold 0.20]
    (2) and the customer age > 12 [threshold 0.20]
    (3) and the customer pregnant or nursing is yes [threshold 0.20]
THEN --------------------------------
    (1)     customer Fem1 is yes [certainty 1.00]
ELSE --------------------------------
    (1)     customer Fem1 is no [certainty 1.00]

RULE #200 priority 90 - Headache no select
IF --------------------------------
    (1)     the main symptom is Headache [threshold 0.20]
    (2) and the Headache type is migraine [threshold 0.20]
    (3) or  the main symptom is Headache [threshold 0.20]
    (4) and the Headache pain is "sharp or severe" [threshold 0.20]
    (5) or  the main symptom is Headache [threshold 0.20]
    (6) and the Headache frequency is often [threshold 0.20]
    (7) or  the main symptom is Headache [threshold 0.20]
    (8) and the Headache duration >= 2 [threshold 0.20]
THEN --------------------------------
    (1)     recommended drug class is "no select" [certainty 1.00]

RULE #201 priority 90 - Toothache no select
IF --------------------------------
    (1)     the main symptom is Toothache [threshold 0.20]
    (2) and the Toothache pain is "sharp or severe" [threshold 0.20]
    (3) or  the main symptom is Toothache [threshold 0.20]
    (4) and the Toothache frequency is often [threshold 0.20]
    (5) or  the main symptom is Toothache [threshold 0.20]
    (6) and the Dentist recommendation is no [threshold 0.20]
    (7) or  the main symptom is Toothache [threshold 0.20]
    (8) and the Toothache duration >= 2 [threshold 0.20]
THEN --------------------------------
    (1)     recommended drug class is "no select" [certainty 1.00]

RULE #202 priority 90 - Menstrual pain no select
IF --------------------------------
    (1)     the main symptom is "Menstrual Pain" [threshold 0.20]
    (2) and the customer gender is male [threshold 0.20]
    (3) or  the main symptom is "Menstrual Pain" [threshold 0.20]
    (4) and the customer gender is female [threshold 0.20]
    (5) and the Menstrual Pain duration >= 2 [threshold 0.20]
    (6) or  the main symptom is "Menstrual Pain" [threshold 0.20]
    (7) and the customer gender is female [threshold 0.20]
    (8) and the Menstrual Pain frequency is "almost every month" [threshold 0.20]
    (9) or  the main symptom is "Menstrual Pain" [threshold 0.20]
    (10) and the customer gender is female [threshold 0.20]
    (11) and the Menstrual Pain occurrence is "During my period" [threshold 0.20]
    (12) or  the main symptom is "Menstrual Pain" [threshold 0.20]
    (13) and the customer gender is female [threshold 0.20]
    (14) and the Menstrual Pain pain is "sharp or severe" [threshold 0.20]
THEN --------------------------------
    (1)     recommended drug class is "no select" [certainty 1.00]

RULE #203 priority 90 - Backache no select
IF --------------------------------
    (1)     the main symptom is Backache [threshold 0.20]
    (2) and the Backache pain is "sharp or severe" [threshold 0.20]
    (3) or  the main symptom is Backache [threshold 0.20]
    (4) and the Backache frequency is often [threshold 0.20]
    (5) or  the main symptom is Backache [threshold 0.20]
    (6) and the redness or swelling symptom is yes [threshold 0.20]
    (7) or  the main symptom is Backache [threshold 0.20]
    (8) and the Backache duration >= 2 [threshold 0.20]
THEN --------------------------------
    (1)     recommended drug class is "no select" [certainty 1.00]

RULE #204 priority 90 - Muscle pain no select
IF --------------------------------
    (1)     the main symptom is "Muscle Pain" [threshold 0.20]
    (2) and the Muscle Pain pain is "sharp or severe" [threshold 0.20]
    (3) or  the main symptom is "Muscle Pain" [threshold 0.20]
    (4) and the Muscle Pain frequency is often [threshold 0.20]
    (5) or  the main symptom is "Muscle Pain" [threshold 0.20]
    (6) and the redness or swelling symptom is yes [threshold 0.20]
    (7) or  the main symptom is "Muscle Pain" [threshold 0.20]
    (8) and the Muscle Pain duration >= 2 [threshold 0.20]
THEN --------------------------------
    (1)     recommended drug class is "no select" [certainty 1.00]

RULE #205 priority 90 - Joint pain no select
IF --------------------------------
```

```
    (1)     the main symptom is "Joint Pain" [threshold 0.20]
    (2) and the Joint Pain pain is "sharp or severe" [threshold 0.20]
    (3) or  the main symptom is "Joint Pain" [threshold 0.20]
    (4) and the Joint Pain frequency is often [threshold 0.20]
    (5) or  the main symptom is "Joint Pain" [threshold 0.20]
    (6) and the redness or swelling symptom is yes [threshold 0.20]
    (7) or  the main symptom is "Joint Pain" [threshold 0.20]
    (8) and the Joint Pain duration >= 2 [threshold 0.20]
THEN -----------------------------
    (1)     recommended drug class is "no select" [certainty 1.00]
```

RULE #206 priority 90 - Arthritis pain no select
```
IF -----------------------------
    (1)     the main symptom is "Arthritis Pain" [threshold 0.20]
    (2) and the Arthritis Pain pain is "sharp or severe" [threshold 0.20]
    (3) or  the main symptom is "Arthritis Pain" [threshold 0.20]
    (4) and the Arthritis Pain frequency is often [threshold 0.20]
    (5) or  the main symptom is "Arthritis Pain" [threshold 0.20]
    (6) and the redness or swelling symptom is yes [threshold 0.20]
    (7) or  the main symptom is "Arthritis Pain" [threshold 0.20]
    (8) and the Arthritis diagnosis is yes [threshold 0.20]
    (9) and the doctor's recommendation is no [threshold 0.20]
    (10) or  the main symptom is "Arthritis Pain" [threshold 0.20]
    (11) and the Arthritis Pain duration >= 2 [threshold 0.20]
    (12) or  the main symptom is "Arthritis Pain" [threshold 0.20]
    (13) and the Arthritis diagnosis is no [threshold 0.20]
THEN -----------------------------
    (1)     recommended drug class is "no select" [certainty 1.00]
```

RULE #207 priority 90 - eye/ear/leg cramps no select
```
IF -----------------------------
    (1)     the main symptom is any("Eye pain","Ear pain","Leg cramps") [threshold 0.20]
THEN -----------------------------
    (1)     recommended drug class is "no select" [certainty 1.00]
```

RULE #210 priority 90 - general no select
```
IF -----------------------------
    (1)     the recommended drug class is Analgesic [threshold 0.20]
    (2) and the customer Fem1 is yes [threshold 0.20]
    (3) or  the recommended drug class is Analgesic [threshold 0.20]
    (4) and the customer gender is female [threshold 0.20]
    (5) and the customer age >= 13 [threshold 0.20]
    (6) and the customer age < 55 [threshold 0.20]
    (7) and the customer prescription not birth control is yes [threshold 0.20]
    (8) or  the recommended drug class is Analgesic [threshold 0.20]
    (9) and the customer gender is male [threshold 0.20]
    (10) and the customer use of prescription medication is yes [threshold 0.20]

(11) or  the recommended drug class is Analgesic [threshold 0.20]
    (12) and the customer gender is female [threshold 0.20]
    (13) and the customer age < 13 [threshold 0.20]
    (14) and the customer use of prescription medication is yes [threshold 0.20]

(15) or  the recommended drug class is Analgesic [threshold 0.20]
    (16) and the customer gender is female [threshold 0.20]
    (17) and the customer age >= 55 [threshold 0.20]
    (18) and the customer use of prescription medication is yes [threshold 0.20]

THEN -----------------------------
    (1)     recommended drug class is "no select" [certainty 1.00]

* * *   R U L E S   * * *   of   E:\MEDSCR\MAHOGANY\MOD11B.KB   * * *
```

APPENDIX 4

```
    * * *   R U L E S   * * *   of   E:\MEDSCR\KB\MOD12D.KB   * * *
```

RULE #50 priority 90 - indigestion specific no select
```
IF -----------------------------
    (1)     the main symptom is "indigestion (upset or sour stomach)" [threshold 0.20]
    (2) and the indigestion duration > 6 [threshold 0.20]
    (3) or  the main symptom is "indigestion (upset or sour stomach)" [threshold 0.20]
    (4) and the customer RC1 is no [threshold 0.20]
    (5) or  the main symptom is "indigestion (upset or sour stomach)" [threshold 0.20]
    (6) and the customer RC8 is yes [threshold 0.20]
THEN -----------------------------
    (1)     recommended drug class is "no select" [certainty 1.00]
```

RULE #51 priority 89 - antacid path no select
```
IF -----------------------------
    (1)     the main path is antacid [threshold 0.20]
    (2) and the customer RC2 is yes [threshold 0.20]
    (3) or  the main path is antacid [threshold 0.20]
    (4) and the customer arthritis is yes [threshold 0.20]
```

```
THEN -----------------------------
    (1)     recommended drug class is "no select" [certainty 1.00]

RULE #52 priority 89 - Gaviscon path no select
IF -----------------------------
    (1)     the main path is gaviscon [threshold 0.20]
    (2) and the customer RC2 is yes [threshold 0.20]
    (3) or  the main path is gaviscon [threshold 0.20]
    (4) and the customer arthritis is yes [threshold 0.20]
THEN -----------------------------
    (1)     recommended drug class is "no select" [certainty 1.00]

RULE #53 priority 88 - heartburn no select
IF -----------------------------
    (1)     the main symptom is heartburn [threshold 0.20]
    (2) and the heartburn duration > 6 [threshold 0.20]
    (3) or  the main symptom is heartburn [threshold 0.20]
    (4) and the customer RC3 is yes [threshold 0.20]
THEN -----------------------------
    (1)     recommended drug class is "no select" [certainty 1.00]

RULE #54 priority 86 - gas no select
IF -----------------------------
    (1)     the main symptom is gas [threshold 0.20]
    (2) and the customer RC4 is yes [threshold 0.20]
THEN -----------------------------
    (1)     recommended drug class is "no select" [certainty 1.00]

RULE #55 priority 84 - diarrhea no select
IF -----------------------------
    (1)     the main symptom is diarrhea [threshold 0.20]
    (2) and the diarrhea duration > 3 [threshold 0.20]
    (3) or  the main symptom is diarrhea [threshold 0.20]
    (4) and the customer RC5 is yes [threshold 0.20]
THEN -----------------------------
    (1)     recommended drug class is "no select" [certainty 1.00]

RULE #56 priority 82 - constipation no select
IF -----------------------------
    (1)     the main symptom is constipation [threshold 0.20]
    (2) and the customer RC6 is yes [threshold 0.20]
    (3) or  the main symptom is constipation [threshold 0.20]
    (4) and the customer age <= 2 [threshold 0.20]
THEN -----------------------------
    (1)     recommended drug class is "no select" [certainty 1.00]

RULE #57 priority 80 - nausea no select
IF -----------------------------
    (1)     the main symptom is "nausea or vomiting" [threshold 0.20]
    (2) and the nausea duration > 2 [threshold 0.20]
    (3) or  the main symptom is "nausea or vomiting" [threshold 0.20]
    (4) and the customer RC7 is yes [threshold 0.20]
THEN -----------------------------
    (1)     recommended drug class is "no select" [certainty 1.00]

RULE #101 priority 89 - antacid1 main choice direct
IF -----------------------------
    (1)     the main path is antacid [threshold 0.20]
    (2) and the customer kidney problems is no [threshold 0.20]
THEN -----------------------------
    (1)     main choice is antacid1 [certainty 1.00]

RULE #102 priority 89 - antacid2 main choice direct
IF -----------------------------
    (1)     the main path is antacid [threshold 0.20]
    (2) and the customer kidney problems is yes [threshold 0.20]
THEN -----------------------------
    (1)     main choice is antacid2 [certainty 1.00]

RULE #103 priority 87 - antacid1 main choice from gaviscon
IF -----------------------------
    (1)     the main path is gaviscon [threshold 0.20]
    (2) and the customer kidney problems is no [threshold 0.20]
    (3) and the heartburn heart/blood pressure/edema is yes [threshold 0.20]
THEN -----------------------------
    (1)     main choice is antacid1 [certainty 1.00]

RULE #104 priority 87 - antacid2 main choice from gaviscon
IF -----------------------------
    (1)     the main path is gaviscon [threshold 0.20]
    (2) and the customer kidney problems is yes [threshold 0.20]
THEN -----------------------------
    (1)     main choice is antacid2 [certainty 1.00]

RULE #105 priority 87 - gaviscon main choice direct
IF -----------------------------
    (1)     the main path is gaviscon [threshold 0.20]
    (2) and the customer kidney problems is no [threshold 0.20]
    (3) and the heartburn heart/blood pressure/edema is no [threshold 0.20]
```

```
THEN ------------------------------
     (1)     main choice is gaviscon [certainty 1.00]

RULE #106 priority 85 - simethicone main choice
IF ------------------------------
     (1)     the main symptom is gas [threshold 0.20]
THEN ------------------------------
     (1)     main choice is simethicone [certainty 1.00]

RULE #107 priority 81 - constipation main choice
IF ------------------------------
     (1)     the main symptom is constipation [threshold 0.20]
THEN ------------------------------
     (1)     main choice is constipation [certainty 1.00]

RULE #108 priority 83 - diarrhea main choice
IF ------------------------------
     (1)     the main symptom is diarrhea [threshold 0.20]
THEN ------------------------------
     (1)     main choice is diarrhea [certainty 1.00]

RULE #109 priority 79 - nausea main choice
IF ------------------------------
     (1)     the main symptom is "nausea or vomiting" [threshold 0.20]
THEN ------------------------------
     (1)     main choice is nausea [certainty 1.00]

RULE #200 priority 89 - antacid1 constipation recommendation
IF ------------------------------
     (1)     the main choice is antacid1 [threshold 0.20]
     (2) and the customer SC1 is yes [threshold 0.20]
THEN ------------------------------
     (1)     recommended drug class is "Antacid II" [certainty 1.00]

RULE #201 priority 89 - antacid1 diarrhea recommendation
IF ------------------------------
     (1)     the main choice is antacid1 [threshold 0.20]
     (2) and the customer SC1 is no [threshold 0.20]
     (3) and the customer SC2 is yes [threshold 0.20]
THEN ------------------------------
     (1)     recommended drug class is "Antacid I" [certainty 1.00]

RULE #202 priority 89 - antacid1 default recommendation
IF ------------------------------
     (1)     the main choice is antacid1 [threshold 0.20]
     (2) and the customer SC1 is no [threshold 0.20]
     (3) and the customer SC2 is no [threshold 0.20]
THEN ------------------------------
     (1)     recommended drug class is "Antacid I" [certainty 1.00]
     (2) and recommended drug class is "Antacid III" [certainty 1.00]

RULE #203 priority 89 - antacid2 constipation recommendation
IF ------------------------------
     (1)     the main choice is antacid2 [threshold 0.20]
     (2) and the customer SC1 is yes [threshold 0.20]
THEN ------------------------------
     (1)     recommended drug class is "Antacid II" [certainty 1.00]

RULE #204 priority 89 - antacid2 default recommendation
IF ------------------------------
     (1)     the main choice is antacid2 [threshold 0.20]
     (2) and the customer SC1 is no [threshold 0.20]
THEN ------------------------------
     (1)     recommended drug class is "Antacid I" [certainty 1.00]

RULE #210 priority 87 - gaviscon recommendation
IF ------------------------------
     (1)     the main choice is gaviscon [threshold 0.20]
THEN ------------------------------
     (1)     recommended drug class is "Alginic Compounds" [certainty 1.00]

RULE #220 priority 85 - simethicone recommendation
IF ------------------------------
     (1)     the main choice is simethicone [threshold 0.20]
THEN ------------------------------
     (1)     recommended drug class is Antiflatulent [certainty 1.00]

RULE #230 priority 81 - constipation bowel disease recommendation
IF ------------------------------
     (1)     the main choice is constipation [threshold 0.20]
     (2) and the customer bowel disease is yes [threshold 0.20]
THEN ------------------------------
     (1)     recommended drug class is "Laxative IV" [certainty 1.00]

RULE #231 priority 81 - constipation young immediate recommendation
IF ------------------------------
     (1)     the main choice is constipation [threshold 0.20]
```

```
        (2) and the customer bowel disease is no [threshold 0.20]
        (3) and the constipation immediate relief is yes [threshold 0.20]
        (4) and the customer age < 6 [threshold 0.20]
THEN ------------------------------
        (1)     recommended drug class is "Laxative III" [certainty 1.00]

RULE #232 priority 81 - constipation old immediate recommendation
IF ------------------------------
        (1)     the main choice is constipation [threshold 0.20]
        (2) and the customer bowel disease is no [threshold 0.20]
        (3) and the constipation immediate relief is yes [threshold 0.20]
        (4) and the customer age >= 6 [threshold 0.20]
THEN ------------------------------
        (1)     recommended drug class is "Laxative V" [certainty 1.00]

RULE #233 priority 81 - constipation mild recommendation
IF ------------------------------
        (1)     the main choice is constipation [threshold 0.20]
        (2) and the customer bowel disease is no [threshold 0.20]
        (3) and the constipation immediate relief is no [threshold 0.20]
        (4) and the constipation severity is mild [threshold 0.20]
THEN ------------------------------
        (1)     recommended drug class is "Laxative IV" [certainty 1.00]

RULE #234 priority 81 - constipation moderate/severe recommendation
IF ------------------------------
        (1)     the main choice is constipation [threshold 0.20]
        (2) and the customer bowel disease is no [threshold 0.20]
        (3) and the constipation immediate relief is no [threshold 0.20]
        (4) and the constipation severity is any(moderate,severe) [threshold 0.20]
THEN ------------------------------
        (1)     recommended drug class is "Laxative I" [certainty 1.00]

RULE #240 priority 83 - diarrhea traveled recommendation
IF ------------------------------
        (1)     the main choice is diarrhea [threshold 0.20]
        (2) and the diarrhea traveled is yes [threshold 0.20]
THEN ------------------------------
        (1)     recommended drug class is "Antidiarrheal I" [certainty 1.00]

RULE #241 priority 83 - diarrhea dairy recommendation
IF ------------------------------
        (1)     the main choice is diarrhea [threshold 0.20]
        (2) and the diarrhea traveled is no [threshold 0.20]
        (3) and the diarrhea dairy products is yes [threshold 0.20]
THEN ------------------------------
        (1)     recommended drug class is "Antidiarrheal II" [certainty 1.00]

RULE #242 priority 83 - diarrhea food poisoning recommendation
IF ------------------------------
        (1)     the main choice is diarrhea [threshold 0.20]
        (2) and the diarrhea traveled is no [threshold 0.20]
        (3) and the diarrhea dairy products is no [threshold 0.20]
        (4) and the diarrhea food poisoning is yes [threshold 0.20]
THEN ------------------------------
        (1)     recommended drug class is "Fluid Replacement" [certainty 1.00]

RULE #243 priority 83 - diarrhea bowel disease recommendation
IF ------------------------------
        (1)     the main choice is diarrhea [threshold 0.20]
        (2) and the diarrhea traveled is no [threshold 0.20]
        (3) and the diarrhea dairy products is no [threshold 0.20]
        (4) and the diarrhea food poisoning is no [threshold 0.20]
        (5) and the customer bowel disease is yes [threshold 0.20]
THEN ------------------------------
        (1)     recommended drug class is "Laxative IV" [certainty 1.00]

RULE #244 priority 83 - diarrhea mild recommendation
IF ------------------------------
        (1)     the main choice is diarrhea [threshold 0.20]
        (2) and the diarrhea traveled is no [threshold 0.20]
        (3) and the diarrhea dairy products is no [threshold 0.20]
        (4) and the diarrhea food poisoning is no [threshold 0.20]
        (5) and the customer bowel disease is no [threshold 0.20]
        (6) and the diarrhea severity is mild [threshold 0.20]
THEN ------------------------------
        (1)     recommended drug class is "Antidiarrheal IV" [certainty 1.00]

RULE #245 priority 83 - diarrhea moderate/severe recommendation
IF ------------------------------
        (1)     the main choice is diarrhea [threshold 0.20]
        (2) and the diarrhea traveled is no [threshold 0.20]
        (3) and the diarrhea dairy products is no [threshold 0.20]
        (4) and the diarrhea food poisoning is no [threshold 0.20]
        (5) and the customer bowel disease is no [threshold 0.20]
        (6) and the diarrhea severity is any(moderate,severe) [threshold 0.20]
THEN ------------------------------
        (1)     recommended drug class is "Antidiarrheal III" [certainty 1.00]
```

RULE #250 priority 79 - nausea heart disease/blood pressure/glaucoma recommendation
IF ------------------------------
    (1)     the main choice is nausea [threshold 0.20]
    (2) and the nausea heart disease/blood pressure/glaucoma is yes [threshold 0.20]
THEN ------------------------------
    (1)     recommended drug class is "Antidiarrheal I" [certainty 1.00]

RULE #251 priority 79 - nausea default recommendation
IF ------------------------------
    (1)     the main choice is nausea [threshold 0.20]
    (2) and the nausea heart disease/blood pressure/glaucoma is no [threshold 0.20]
THEN ------------------------------
    (1)     recommended drug class is Antinauseant [certainty 1.00]

RULE #300 priority 89 - antacid path (indigestion)
IF ------------------------------
    (1)     the main symptom is "indigestion (upset or sour stomach)" [threshold 0.20]
THEN ------------------------------
    (1)     main path is antacid [certainty 1.00]

RULE #301 priority 87 - antacid path (heartburn)
IF ------------------------------
    (1)     the main symptom is heartburn [threshold 0.20]
    (2) and the heartburn first time symptoms is yes [threshold 0.20]
    (3) or  the main symptom is heartburn [threshold 0.20]
    (4) and the heartburn first time symptoms is no [threshold 0.20]
    (5) and the heartburn prior antacid use is yes [threshold 0.20]
    (6) and the heartburn antacids relieved symptoms is yes [threshold 0.20]
    (7) or  the main symptom is heartburn [threshold 0.20]
    (8) and the heartburn first time symptoms is no [threshold 0.20]
    (9) and the heartburn prior antacid use is no [threshold 0.20]
    (10) and the heartburn prior Gaviscon use is no [threshold 0.20]
    (11) or  the main symptom is heartburn [threshold 0.20]
    (12) and the heartburn first time symptoms is no [threshold 0.20]
    (13) and the heartburn prior antacid use is no [threshold 0.20]
    (14) and the heartburn prior Gaviscon use is yes [threshold 0.20]
    (15) and the heartburn Gaviscon relieved symptoms is no [threshold 0.20]
    (16) or  the main symptom is heartburn [threshold 0.20]
    (17) and the heartburn first time symptoms is no [threshold 0.20]
    (18) and the heartburn prior antacid use is yes [threshold 0.20]
    (19) and the heartburn antacids relieved symptoms is no [threshold 0.20]
    (20) and the heartburn prior Gaviscon use is yes [threshold 0.20]
    (21) and the heartburn Gaviscon relieved symptoms is no [threshold 0.20]
THEN ------------------------------
    (1)     main path is antacid [certainty 1.00]

RULE #302 priority 87 - gaviscon path
IF ------------------------------
    (1)     the main symptom is heartburn [threshold 0.20]
    (2) and the heartburn first time symptoms is no [threshold 0.20]
    (3) and the heartburn prior antacid use is yes [threshold 0.20]
    (4) and the heartburn antacids relieved symptoms is no [threshold 0.20]
    (5) and the heartburn prior Gaviscon use is yes [threshold 0.20]
    (6) and the heartburn Gaviscon relieved symptoms is yes [threshold 0.20]
    (7) or  the main symptom is heartburn [threshold 0.20]
    (8) and the heartburn first time symptoms is no [threshold 0.20]
    (9) and the heartburn prior antacid use is no [threshold 0.20]
    (10) and the heartburn prior Gaviscon use is yes [threshold 0.20]
    (11) and the heartburn Gaviscon relieved symptoms is yes [threshold 0.20]
    (12) or  the main symptom is heartburn [threshold 0.20]
    (13) and the heartburn first time symptoms is no [threshold 0.20]
    (14) and the heartburn prior antacid use is yes [threshold 0.20]
    (15) and the heartburn antacids relieved symptoms is no [threshold 0.20]
    (16) and the heartburn prior Gaviscon use is no [threshold 0.20]
THEN ------------------------------
    (1)     main path is gaviscon [certainty 1.00]

RULE #303 priority 87 - other path
IF ------------------------------
    (1)     the main symptom is any(gas,diarrhea,constipation,"nausea or vomiting") [threshold 0.20]
THEN ------------------------------
    (1)     main path is other [certainty 1.00]

RULE #400 priority 95 - RC1
IF ------------------------------
    (1)     the indigestion sudden start is no [threshold 0.20]
    (2) and the indigestion over eating/foods/drinking/aspirin is no [threshold 0.20]
    (3) or  the customer chest pain is yes [threshold 0.20]
THEN ------------------------------
    (1)     customer RC1 is yes [certainty 1.00]
ELSE ------------------------------
    (1)     customer RC1 is no [certainty 1.00]

```
RULE #401 priority 95 - RC2
    IF ------------------------------
        (1)      the indigestion spitting blood/black stools is yes [threshold 0.20]
        (2) or  the indigestion or heartburn more than once a week is yes [threshold
0.20]
    THEN ------------------------------
        (1)      customer RC2 is yes [certainty 1.00]
    ELSE ------------------------------
        (1)      customer RC2 is no [certainty 1.00]

RULE #402 priority 95 - RC3
    IF ------------------------------
        (1)      the heartburn sudden start is no [threshold 0.20]
        (2) and the heartburn bedtime symptoms is no [threshold 0.20]
        (3) and the heartburn over eating/drinking/high fat/smoking/clothes is no [t
hreshold 0.20]
        (4) or  the customer chest pain is yes [threshold 0.20]
    THEN ------------------------------
        (1)      customer RC3 is yes [certainty 1.00]
    ELSE ------------------------------
        (1)      customer RC3 is no [certainty 1.00]

RULE #403 priority 95 - RC4
    IF ------------------------------
        (1)      the gas lactose/carbohydrates is yes [threshold 0.20]
        (2) and the gas change diet is yes [threshold 0.20]
        (3) or  the customer chest pain is yes [threshold 0.20]
    THEN ------------------------------
        (1)      customer RC4 is yes [certainty 1.00]
    ELSE ------------------------------
        (1)      customer RC4 is no [certainty 1.00]

RULE #404 priority 95 - RC5
    IF ------------------------------
        (1)      the diarrhea antibiotics/antacids/laxatives is yes [threshold 0.20]
        (2) or  the diarrhea bloody stools/abdominal pain/high fever is yes [thresho
ld 0.20]
        (3) or  the diarrhea ulcer/diabetes/heart disease/kidney disease is yes [thr
eshold 0.20]
        (4) or  the diarrhea new medication is yes [threshold 0.20]
    THEN ------------------------------
        (1)      customer RC5 is yes [certainty 1.00]
    ELSE ------------------------------
        (1)      customer RC5 is no [certainty 1.00]

RULE #405 priority 95 - RC6
    IF ------------------------------
        (1)      the constipation anorexia/headache/back pain/abdominal swelling is
no [threshold 0.20]
        (2) or  the constipation fiber/defecate/physical/fluids/stresses is no [thre
shold 0.20]
        (3) or  the constipation laxatives is yes [threshold 0.20]
        (4) or  the constipation within 14 days is yes [threshold 0.20]
        (5) or  the constipation prescription medications is yes [threshold 0.20]
        (6) or  the constipation daily laxative use is yes [threshold 0.20]
    THEN ------------------------------
        (1)      customer RC6 is yes [certainty 1.00]
    ELSE ------------------------------
        (1)      customer RC6 is no [certainty 1.00]

RULE #406 priority 95 - RC7
    IF ------------------------------
        (1)      the customer age <= 5 [threshold 0.20]
        (2) or  the customer gender is female [threshold 0.20]
        (3) and the customer age >= 13 [threshold 0.20]
        (4) and the customer age < 55 [threshold 0.20]
        (5) and the customer prescription not birth control is yes [threshold 0.20]
        (6) or  the customer gender is female [threshold 0.20]
        (7) and the customer age < 13 [threshold 0.20]
        (8) and the customer prescription medications is yes [threshold 0.20]
        (9) or  the customer gender is female [threshold 0.20]
        (10) and the customer age >= 55 [threshold 0.20]
        (11) and the customer prescription medications is yes [threshold 0.20]
        (12) or  the customer gender is male [threshold 0.20]
        (13) and the customer prescription medications is yes [threshold 0.20]
        (14) or  the customer gender is male [threshold 0.20]
        (15) and the customer age > 40 [threshold 0.20]
        (16) and the customer difficulty in urination is yes [threshold 0.20]
        (17) or  the nausea chest pain/abdominal pain/bloody vomiting/high fever is
yes [threshold 0.20]
    THEN ------------------------------
        (1)      customer RC7 is yes [certainty 1.00]
    ELSE ------------------------------
        (1)      customer RC7 is no [certainty 1.00]
```

```
RULE #407 priority 95 - RC8
   IF ---------------------------
      (1)      the indigestion stomach pain is yes [threshold 0.20]
      (2) or  the indigestion cramps is yes [threshold 0.20]
   THEN -------------------------
      (1)      customer RC8 is yes [certainty 1.00]
   ELSE -------------------------
      (1)      customer RC8 is no [certainty 1.00]

RULE #500 priority 95 - SC1
   IF ---------------------------
      (1)      the main symptom is constipation [threshold 0.20]
      (2) or  the customer constipation is yes [threshold 0.20]
   THEN -------------------------
      (1)      customer SC1 is yes [certainty 1.00]
   ELSE -------------------------
      (1)      customer SC1 is no [certainty 1.00]

RULE #501 priority 95 - SC2
   IF ---------------------------
      (1)      the main symptom is diarrhea [threshold 0.20]
      (2) or  the customer diarrhea is yes [threshold 0.20]
   THEN -------------------------
      (1)      customer SC2 is yes [certainty 1.00]
   ELSE -------------------------
      (1)      customer SC2 is no [certainty 1.00]

* * *  R U L E S  * * *   of   E:\MEDSCR\KB\MOD12D.KB     * * *
```

APPENDIX 5

```
      * * *  R U L E S  * * *   of   E:\MEDSCR\MAHOGANY\MOD14C.KB     * * *

RULE #1 priority 95 - Possible main symptoms
   IF ---------------------------
      (1)      the main symptom is objectname(<symptom>) [threshold 0.20]
   THEN -------------------------
      (1)      level 1 drug class is <symptom | drug class> [certainty 1.00]

RULE #10 priority 90 - level 1 antihistamine to rec
   IF ---------------------------
      (1)      the level 1 drug class is antihistamine [threshold 0.20]
   THEN -------------------------
      (1)      recommended drug class is antihistamine [certainty 1.00]

RULE #11 priority 90 - level 1 ophthalmic vasoconstrictor to rec
   IF ---------------------------
      (1)      the level 1 drug class is "ophthalmic vasoconstrictor" [threshold 0.20]
   THEN -------------------------
      (1)      recommended drug class is "ophthalmic vasoconstrictor" [certainty 1.00]

RULE #100 priority 90 - respiratory problem no select
   IF ---------------------------
      (1)      the main symptom is any("runny nose","stuffy nose",sneezing) [threshold 0.20]
      (2) and the customer AC1401 is yes [threshold 0.20]
      (3) and the customer AC1402 is yes [threshold 0.20]
      (4) or  the main symptom is any("runny nose","stuffy nose",sneezing) [threshold 0.20]
      (5) and the customer AC1403 is yes [threshold 0.20]
      (6) or  the main symptom is any("runny nose","stuffy nose",sneezing) [threshold 0.20]
      (7) and the customer AC1404 is yes [threshold 0.20]
      (8) or  the main symptom is any("runny nose","stuffy nose",sneezing) [threshold 0.20]
      (9) and the customer AC1405 is yes [threshold 0.20]
   THEN -------------------------
      (1)      recommended drug class is "no select" [certainty 1.00]

RULE #101 priority 90 - runny nose to no select
   IF ---------------------------
      (1)      the main symptom is "runny nose" [threshold 0.20]
      (2) and the runny nose duration > 6 [threshold 0.20]
      (3) or  the main symptom is "runny nose" [threshold 0.20]
      (4) and the runny nose discharge is "thick or green" [threshold 0.20]
      (5) or  the main symptom is "runny nose" [threshold 0.20]
      (6) and the runny nose medication use is yes [threshold 0.20]
   THEN -------------------------
      (1)      recommended drug class is "no select" [certainty 1.00]

RULE #102 priority 90 - sneezing to no select
   IF ---------------------------
      (1)      the main symptom is sneezing [threshold 0.20]
      (2) and the sneezing duration > 6 [threshold 0.20]
      (3) or  the main symptom is sneezing [threshold 0.20]
      (4) and the sneezing medication use is yes [threshold 0.20]
```

```
       THEN -----------------------------
           (1)       recommended drug class is "no select" [certainty 1.00]

RULE #103 priority 90 - watering or red eyes to no select
     IF -----------------------------
           (1)       the main symptom is "watering or red eyes" [threshold 0.20]
           (2) and   the watering or red eyes duration > 6 [threshold 0.20]
           (3) or    the main symptom is "watering or red eyes" [threshold 0.20]
           (4) and   the eye itch or sting is yes [threshold 0.20]
           (5) or    the main symptom is "watering or red eyes" [threshold 0.20]
           (6) and   the eye pain is yes [threshold 0.20]
           (7) or    the main symptom is "watering or red eyes" [threshold 0.20]
           (8) and   the eye blurred or double vision is yes [threshold 0.20]
           (9) or    the main symptom is "watering or red eyes" [threshold 0.20]
           (10) and  the eye discharge or twitch is yes [threshold 0.20]
           (11) or   the main symptom is "watering or red eyes" [threshold 0.20]
           (12) and  the contact lens use is yes [threshold 0.20]
           (13) or   the main symptom is "watering or red eyes" [threshold 0.20]
           (14) and  the watering or red eyes medication use is yes [threshold 0.20]
       THEN -----------------------------
           (1)       recommended drug class is "no select" [certainty 1.00]

RULE #104 priority 90 - stuffy nose no select
     IF -----------------------------
           (1)       the main symptom is "stuffy nose" [threshold 0.20]
           (2) and   the stuffy nose duration > 6 [threshold 0.20]
           (3) and   the main symptom is "stuffy nose" [threshold 0.20]
           (4) and   the stuffy nose medication use is yes [threshold 0.20]
       THEN -----------------------------
           (1)       recommended drug class is "no select" [certainty 1.00]

RULE #105 priority 90 - itching skin no select
     IF -----------------------------
           (1)       the main symptom is "itching skin or rash" [threshold 0.20]
           (2) and   the itching skin or rash duration > 6 [threshold 0.20]
           (3) or    the main symptom is "itching skin or rash" [threshold 0.20]
           (4) and   the itching skin or rash skin condition is moist [threshold 0.20]
           (5) and   the moist areas or blisters duration > 3 [threshold 0.20]
           (6) or    the main symptom is "itching skin or rash" [threshold 0.20]
           (7) and   the itching skin or rash skin condition is dry [threshold 0.20]
           (8) and   the dry or cracking skin duration > 6 [threshold 0.20]
           (9) or    the main symptom is "itching skin or rash" [threshold 0.20]
           (10) and  the customer AC1416 is yes [threshold 0.20]
           (11) or   the main symptom is "itching skin or rash" [threshold 0.20]
           (12) and  the customer infection/psoriasis is yes [threshold 0.20]
       THEN -----------------------------
           (1)       recommended drug class is "no select" [certainty 1.00]

RULE #106 priority 90 - antihistamine no select
     IF -----------------------------
           (1)       the level 1 drug class is antihistamine [threshold 0.20]
           (2) and   the customer CC1 is yes [threshold 0.20]
           (3) or    the level 1 drug class is antihistamine [threshold 0.20]
           (4) and   the customer CC2 is yes [threshold 0.20]
       THEN -----------------------------
           (1)       recommended drug class is "no select" [certainty 1.00]

RULE #200 priority 90 - Level 1 decon w no spray to recommend
     IF -----------------------------
           (1)       the level 1 drug class is decongestant [threshold 0.20]
           (2) and   the customer decon medication use is yes [threshold 0.20]
           (3) and   the customer nasal spray use is no [threshold 0.20]
       THEN -----------------------------
           (1)       recommended drug class is "decongestant topical" [certainty 1.00]

RULE #201 priority 90 - Level 1 decon w spray to recommend
     IF -----------------------------
           (1)       the level 1 drug class is decongestant [threshold 0.20]
           (2) and   the customer decon medication use is yes [threshold 0.20]
           (3) and   the customer nasal spray use is yes [threshold 0.20]
       THEN -----------------------------
           (1)       recommended drug class is "Nasal Spray NaCl" [certainty 1.00]

RULE #202 priority 90 - Level 1 decon no other drug to recommend
     IF -----------------------------
           (1)       the level 1 drug class is decongestant [threshold 0.20]
           (2) and   the customer CC1 is no [threshold 0.20]
           (3) and   the customer CC2 is no [threshold 0.20]
           (4) and   the customer AC5 is no [threshold 0.20]
           (5) and   the customer decon medication use is no [threshold 0.20]
       THEN -----------------------------
           (1)       recommended drug class is decongestant [certainty 1.00]

RULE #203 priority 90 - CC1/CC2/AC5 yes level 1 decon w no other to rec spray
     IF -----------------------------
           (1)       the level 1 drug class is decongestant [threshold 0.20]
           (2) and   the customer CC1 is yes [threshold 0.20]
           (3) and   the customer decon medication use is no [threshold 0.20]
```

(4) or   the level 1 drug class is decongestant [threshold 0.20]
        (5) and the customer CC2 is yes [threshold 0.20]
        (6) and the customer decon medication use is no [threshold 0.20]
        (7) or   the level 1 drug class is decongestant [threshold 0.20]
        (8) and the customer AC5 is yes [threshold 0.20]
        (9) and the customer decon medication use is no [threshold 0.20]
THEN ------------------------------
        (1)     recommended drug class is "decongestant topical" [certainty 1.00]

RULE #300 priority 90 - skin prep small moist area to recommend
IF ------------------------------
        (1)     the level 1 drug class is "skin prep" [threshold 0.20]
        (2) and the itching skin or rash skin condition is moist [threshold 0.20]
        (3) and the itching skin or rash area affected is small [threshold 0.20]
THEN ------------------------------
        (1)     recommended drug class is astringent [certainty 1.00]
        (2) and recommended drug class is antipruritic [certainty 1.00]

RULE #301 priority 90 - skin prep large moist area to recommend
IF ------------------------------
        (1)     the level 1 drug class is "skin prep" [threshold 0.20]
        (2) and the itching skin or rash skin condition is moist [threshold 0.20]
        (3) and the itching skin or rash area affected is large [threshold 0.20]
THEN ------------------------------
        (1)     recommended drug class is adjunct [certainty 1.00]
        (2) and recommended drug class is protectant [certainty 1.00]

RULE #302 priority 90 - skin prep hairy area to recommend
IF ------------------------------
        (1)     the level 1 drug class is "skin prep" [threshold 0.20]
        (2) and the itching skin or rash skin condition is dry [threshold 0.20]
        (3) and the itching skin or rash hairy area is yes [threshold 0.20]
THEN ------------------------------
        (1)     recommended drug class is "hydrocortisone-3" [certainty 1.00]

RULE #303 priority 90 - skin prep somewhat dry to recommend
IF ------------------------------
        (1)     the level 1 drug class is "skin prep" [threshold 0.20]
        (2) and the itching skin or rash skin condition is dry [threshold 0.20]
        (3) and the itching skin or rash hairy area is no [threshold 0.20]
        (4) and the itching skin or rash dryness level is "somewhat dry" [threshold 0.20]
THEN ------------------------------
        (1)     recommended drug class is "hydrocortisone-1" [certainty 1.00]

RULE #304 priority 90 - skin prep very dry/cracking to recommend
IF ------------------------------
        (1)     the level 1 drug class is "skin prep" [threshold 0.20]
        (2) and the itching skin or rash skin condition is dry [threshold 0.20]
        (3) and the itching skin or rash hairy area is no [threshold 0.20]
        (4) and the itching skin or rash dryness level is any("very dry",cracking) [threshold 0.20]
THEN ------------------------------
        (1)     recommended drug class is "hydrocortisone-2" [certainty 1.00]

RULE #500 priority 80 - AC1401
IF ------------------------------
        (1)     the customer breathing normal is yes [threshold 0.20]
        (2) and the customer chest congestion is yes [threshold 0.20]
        (3) and the customer cough is yes [threshold 0.20]
THEN ------------------------------
        (1)     customer AC1401 is yes [certainty 1.00]
ELSE ------------------------------
        (1)     customer AC1401 is no [certainty 1.00]

RULE #502 priority 80 - AC1402
IF ------------------------------
        (1)     the customer chest pain is yes [threshold 0.20]
        (2) or   the customer sob is yes [threshold 0.20]
        (3) or   the customer wheeze is yes [threshold 0.20]
THEN ------------------------------
        (1)     customer AC1402 is yes [certainty 1.00]
ELSE ------------------------------
        (1)     customer AC1402 is no [certainty 1.00]

RULE #504 priority 80 - AC1403
IF ------------------------------
        (1)     the customer Asthma, Bronchitis, or Emphysema is yes [threshold 0.20]
THEN ------------------------------
        (1)     customer AC1403 is yes [certainty 1.00]
ELSE ------------------------------
        (1)     customer AC1403 is no [certainty 1.00]

RULE #506 priority 80 - AC1404
IF ------------------------------
        (1)     the customer Pneumonia or Pulmonary Disease is yes [threshold 0.20]

```
THEN ----------------------------
     (1)       customer AC1404 is yes [certainty 1.00]
ELSE ----------------------------
     (1)       customer AC1404 is no [certainty 1.00]

RULE #508 priority 80 - AC1405
  IF ----------------------------
     (1)       the customer smoking is yes [threshold 0.20]
  THEN ----------------------------
     (1)       customer AC1405 is yes [certainty 1.00]
  ELSE ----------------------------
     (1)       customer AC1405 is no [certainty 1.00]

RULE #509 priority 80 - AC1416
  IF ----------------------------
     (1)       the itching area warmer than rest is yes [threshold 0.20]
     (2) or   the itching area pus is yes [threshold 0.20]
     (3) or   the itching area crusty or scaly is yes [threshold 0.20]
  THEN ----------------------------
     (1)       customer AC1416 is yes [certainty 1.00]
  ELSE ----------------------------
     (1)       customer AC1416 is no [certainty 1.00]

RULE #510 priority 80 - CC1
  IF ----------------------------
     (1)       the customer Heart/Thyroid/Blood Pressure/Diabetes is yes [threshol
d 0.20]
  THEN ----------------------------
     (1)       customer CC1 is yes [certainty 1.00]
  ELSE ----------------------------
     (1)       customer CC1 is no [certainty 1.00]

RULE #512 priority 80 - CC2
  IF ----------------------------
     (1)       the customer Depression/Anxiety/Seizures/Respiratory Problems is ye
s [threshold 0.20]
  THEN ----------------------------
     (1)       customer CC2 is yes [certainty 1.00]
  ELSE ----------------------------
     (1)       customer CC2 is no [certainty 1.00]

RULE #514 priority 80 - AC5
  IF ----------------------------
     (1)       the customer gender is male [threshold 0.20]
     (2) and  the customer age > 40 [threshold 0.20]
     (3) and  the customer difficulty in urination is yes [threshold 0.20]
  THEN ----------------------------
     (1)       customer AC5 is yes [certainty 1.00]
  ELSE ----------------------------
     (1)       customer AC5 is no [certainty 1.00]

RULE #515 priority 80 - Fem1
  IF ----------------------------
     (1)       the customer gender is female [threshold 0.20]
     (2) and  the customer age > 12 [threshold 0.20]
     (3) and  the customer pregnancy and nursing mother is yes [threshold 0.20]
  THEN ----------------------------
     (1)       customer Fem1 is yes [certainty 1.00]
  ELSE ----------------------------
     (1)       customer Fem1 is no [certainty 1.00]

RULE #900 priority 90 - general no select
  IF ----------------------------
     (1)       the customer Fem1 is yes [threshold 0.20]
     (2) or   the customer use of medication is yes [threshold 0.20]
  THEN ----------------------------
     (1)       recommended drug class is "no select" [certainty 1.00]

* * *   R U L E S   * * *   of   E:\MEDSCR\MAHOGANY\MOD14C.KB      * * *
```

APPENDIX 6

```
     * * *   R U L E S   * * *   of   E:\MEDSCR\KB\MOD99A.KB      * * *

RULE #100 priority 50 - AC1
  IF ----------------------------
     (1)       the customer oral surgery within the past 7 days is no [threshold 0
.20]
     (2) and  the customer bleeding, clotting problems is no [threshold 0.20]
     (3) and  the customer ulcers, stomach pain, upset stomach, or asthma is no [t
hreshold 0.20]
  THEN ----------------------------
     (1)       customer AC1 is no [certainty 1.00]
  ELSE ----------------------------
     (1)       customer AC1 is yes [certainty 1.00]
```

```
RULE #104 priority 50 - AC2
  IF ------------------------------
      (1)     the customer taking medication to thin blood, for arthritis, or for
  inflammation is no [threshold 0.20]
      (2) and the customer taking any form of aspirin or salicylates is no [thresh
  old 0.20]
  THEN ------------------------------
      (1)     customer AC2 is no [certainty 1.00]
  ELSE ------------------------------
      (1)     customer AC2 is yes [certainty 1.00]

RULE #110 priority 50 - AC3
  IF ------------------------------
      (1)     the customer flu symptoms is no [threshold 0.20]
      (2) and the customer med for gout/diab is no [threshold 0.20]
  THEN ------------------------------
      (1)     customer AC3 is no [certainty 1.00]
  ELSE ------------------------------
      (1)     customer AC3 is yes [certainty 1.00]

RULE #112 priority 50 - AC4
  IF ------------------------------
      (1)     the customer allergy to ibuprofen is no [threshold 0.20]
      (2) and the customer Kidney Problems or Heart Problems is no [threshold 0.20
  ]
  THEN ------------------------------
      (1)     customer AC4 is no [certainty 1.00]
  ELSE ------------------------------
      (1)     customer AC4 is yes [certainty 1.00]

RULE #114 priority 50 - AC5
  IF ------------------------------
      (1)     the customer allergy to acetaminophen is no [threshold 0.20]
  THEN ------------------------------
      (1)     customer AC5 is no [certainty 1.00]
  ELSE ------------------------------
      (1)     customer AC5 is yes [certainty 1.00]

RULE #200 priority 40 - Acetaminophen Yes
  IF ------------------------------
      (1)     the current choice is APAP [threshold 0.20]
      (2) and the customer AC5 is no [threshold 0.20]
  THEN ------------------------------
      (1)     recommended choice is APAP [certainty 1.00]

RULE #204 priority 40 - NSAID's Yes
  IF ------------------------------
      (1)     the current choice is NSAID [threshold 0.20]
      (2) and the customer age >= 18 [threshold 0.20]
      (3) and the customer AC4 is no [threshold 0.20]
      (4) and the customer AC1 is no [threshold 0.20]
      (5) and the customer AC2 is no [threshold 0.20]
  THEN ------------------------------
      (1)     recommended choice is NSAID [certainty 1.00]

RULE #212 priority 40 - Aspirin Yes
  IF ------------------------------
      (1)     the current choice is ASA [threshold 0.20]
      (2) and the customer age >= 18 [threshold 0.20]
      (3) and the customer AC1 is no [threshold 0.20]
      (4) and the customer AC2 is no [threshold 0.20]
      (5) and the customer AC3 is no [threshold 0.20]
  THEN ------------------------------
      (1)     recommended choice is ASA [certainty 1.00]

* * *   R U L E S   * * *   of   E:\MEDSCR\KB\MOD99A.KB      * * *
```

APPENDIX 7

```c
#include <graph.h>
#include <stdio.h>
#include <stdlib.h>
#include <malloc.h>
#include <string.h>
#include <ctype.h>
#include "d4base.h"
#include "oem.h"

#include "data.h"
include "screen.h"
#include "defs.h"
#include "vars.h"

/*
    Definitions for the "UTIL" database.
*/
```

```c
static int     UtilDatabase;      /* utilization database reference */
static int     UtilUserIndex;     /* utilization user index reference */
static int     UtilIndex;         /* utilization index reference */ static long Util_UserID;          /* field definitions */
static long Util_Serial;
static long Util_RecCode;
static long Util_RecProd;
static long Util_Version;
static long Util_BackedUp;
static long Util_BloodP1;
static long Util_BloodP2;
static long Util_BPDate;

/*
    Definitions for the "UTILDET" database.
*/ static int     UtilDetDatabase;   /* utilization detail reference */
static int     UtilDetIndex;      /* utilization index reference */ static long UtilDet_Serial;       /* field definitions */
static long UtilDet_Question;
static long UtilDet_Answer;

/*
    Screen data references.
*/ extern GroupRec RecommendScreen;       /* group for recommendations screen */
extern TextRec  RecommendLeadText;     /* static lead text string */
extern TextRec  RecommendCompsText;    /* static components text string */
extern TextRec  RecommendDrugsText;    /* static drug text string */ extern GroupRec OralTopicalGroup;      /* group for decongestant type screen */ extern GroupRec UserQueryGroup;        /* user query screen */
extern TextRec  UserQueryText;           /* text of query to user */
extern GroupRec UserResponseGroup;       /* group of possible responses */ extern GroupRec PrintingInfoScreen;    /* printing report screen */ extern GroupRec AbortSessionScreen;    /* terminating session screen */

/*
    Drug choice question texts
*/ static char *DrugQueries [DRUG_CHOICES] =
{ if PROF_VERSION
    "Does the patient prefer an alcohol free medicine?",
    "Does the patient prefer a sugar free medicine?",
    "Does the patient prefer an extra strength medicine?",
    "Does the patient prefer a long acting medicine?",
    "Does the patient prefer a night time medicine?",
    "Which form of medicine does the patient prefer?"
#else
    "Do you prefer an alcohol free medicine?",
    "Do you prefer a sugar free medicine?",
    "Do you prefer an extra strength medicine?",
    "Do you prefer a long acting medicine?",
    "Do you prefer a night time medicine?",
    "Which form of medicine do you prefer?"
#endif

};

static char *YesNoChoices [2] =
{
    "No",
    "Yes"
};

/************************************************************************
    qualifier_number Finds the index number of a qualifier specification in the ordered list
    of qualifier values for the current module. Returns -1 if the qualifier
    is blank or not found, the index number otherwise.
************************************************************************/
```

```c
static short qualifier_number (char qual [MAX_QUALIFIER])
{
    int         index;

/* check for a blank qualifier */
    for (index = 0; index < MAX_QUALIFIER; index++)
        if (qual [index] != ' ')
            break;
    if (index >= MAX_QUALIFIER)
        return -1;

/* find the index number in set */
    for (index = 0; index < QUALIFIER_COUNT; index++)
        if (memcmp (qual, ModuleTable [ModuleNumber].Qualify [index],
          MAX_QUALIFIER) == 0)
            return index;
    return -1;
}

/****************************************************************
  find_module

Looks up a knowledgebase by name, returning the index number of the
    knowledgebase.
****************************************************************/ static short find_module (char *name)
{
    int         index;

/* match knowledgebase name */
    for (index = 0; index < KB_COUNT; index++)
        if (stricmp (name, KBTable [index].File) == 0)
            return index;

/* return failure code */
    return -1;
}

/****************************************************************
  open_util

Opens the "UTIL" and "UTILDET" database files.
****************************************************************/ static bool open_util (void)
{
    /* set up for using the utilization file */
    UtilDatabase = use_data ("UTIL");
    UtilUserIndex = index_data ("UTILUSER");
    UtilIndex = index_data ("UTIL");
    Util_UserID = f4ref ("USERID");
    Util_Serial = f4ref ("SERIAL");
    Util_RecCode = f4ref ("RECCODE");
    Util_RecProd = f4ref ("RECPROD");
    Util_Version = f4ref ("VERSION");
    Util_BackedUp = f4ref ("BACKEDUP");
    Util_BloodP1 = f4ref ("BLOOD_P1");
    Util_BloodP2 = f4ref ("BLOOD_P2");
    Util_BPDate = f4ref ("BP_DATE");

/* set up for using the utilization detail file */
    UtilDetDatabase = use_data ("UTILDET");
    UtilDetIndex = index_data ("UTILDET");
    UtilDet_Serial = f4ref ("SERIAL");
    UtilDet_Question = f4ref ("QUESTION");
    UtilDet_Answer = f4ref ("ANSWER");

/* take successful completion return */
    return TRUE;
}

/****************************************************************
  close_util

Closes the "UTIL" and "UTILDET" database files.
****************************************************************/ static void close_util (void)
{
    /* close the utilization database file */
    d4select (UtilDatabase);
    d4close ();
```

```
    /* close the utilization detail database file */
    d4select (UtilDetDatabase),
    d4close ();
}

/****************************************************************
    match_class Finds the best therapeutic class to match a component drug list. If
    the module specifies single ingredient products only, each component
    drug is matched separately with a therapeutic class.
****************************************************************/ static short match_class (char comps [CLASS_COMPONENTS],
                          char qual [QUALIFIER_COUNT], int number)
{
    char        choice [MAX_QUALIFIER + 1];
    char        result [MAX_QUALIFIER + 1];
    double      cert;
    int         match;
    int         best;
    int         count;
    int         least;
    int         length;
    int         num;
    int         index;
    int         check;
    int         sub;
    int         code;
    int         oper;
    int         hold;

/* set match length to check */
    if (ModuleTable [number].Multiple)
    {

/* match all component drug types */
        for (match = 0; match < CLASS_COMPONENTS; match++)
            if (comps [match] < 0)
                break;

}
    else if (comps [0] < 0)
        match = 0;
    else
        match = 1;

/* check for "decongestant" as only component medicine */
    num = register_component (FALSE, "decongestant");
    if (match == 1 && comps [0] == (char) num)
    {

/* find the type of decongestant preferred */
        code = run_template (300, (ItemPtr) &OralTopicalGroup);
        if (code > 0)
            comps [0] = (char) register_component (FALSE, code == 1 ?
                "decongestant oral" : "decongestant topical");
    }

/* loop until valid match found */
    best = -1;
    while (best < 0 && ! SessionAborted)
    {

/* scan all classes for best match */
        count = 0;
        least = QUALIFIER_COUNT;
        for (index = 0; index < TCNCount; index++)
        {

/* find the number of components in the class */
    for (length = 0; length < CLASS_COMPONENTS; length++)
        if (TCNTable [index].Components [length] < 0)
            break;

/* validate qualifier and components */
    num = qualifier_number (TCNTable [index].Qualifier);
    if ((num < 0 || qual [num] >= 0) &&
      (length > count || num < least) && length <= match &&
      ! TCNTable [index].Tried &&
      TCNTable [index].Code [1] == (char) ('0' + number))
    {

/* check for components a subset of those needed */
        sub = 0;
        for (check = 0; check < length && sub < match; check++)
            while (comps [sub] != TCNTable [index].Components [check])
                if (++sub >= match)
                    break;
```

```c
            /* set new best match if so */
            if (sub < match)
            {
                count = length;
                best = index;
                least = num;
            }
        }
    }

/* check for valid qualifier */
    if (least >= QUALIFIER_COUNT)
        break;
    else if (qual [least] == 0)
    {
        char        path [180];

/* load the appropriate knowledgebase */
        hold = ModuleNumber;
        ModuleNumber = find_module (KBTable [hold].Qualifier);
        knowledgebase_path (KBTable [ModuleNumber].File, path);
        code = m_take_control (READ_KBASE, path);
        if (code)
        {
            /* set the qualifier we want to check */
            copy_trunc
                (choice, TCNTable [best].Qualifier, MAX_QUALIFIER);
            QualifyText = choice;

/* attempt all goals in the knowledgebase */
            m_take_control (ATTEMPT_GOALS, NULL);

/* check the result value */
            m_get_value ("recommended | choice", 1, result,
                MAX_QUALIFIER, &cert, &oper);
            if (strcmp (choice, result) == 0)
                qual [least] = 1;
            else
                qual [least] = -1;

/* close the knowledgebase */
            m_take_control (CLOSE_KBASE, path);
        }
        else
                qual [least] = -1;

/* check for qualifier accepted */
            if (qual [least] < 0)
                best = -1;

/* restore the proper module number */
            ModuleNumber = hold;
        }
    }

/* return the best match index */
    if (best >= 0)
        TCNTable [best].Tried = TRUE;
    return best;
}

/****************************************************************
  ask_preference Asks the user for a yes or no choice on a drug characteristic, returning
    the choice result.
****************************************************************/ static short ask_preference (int num, int count, bool set [])
{
    return ask_noyes (10, DrugQueries [num]);
}

/****************************************************************
  ask_doseform Asks the user for the choice of a particular dose form for a drug,
    returning the choice result.
****************************************************************/ static short ask_doseform (int num, int count, bool set [])
{
    char        *choices [FORM_CODES];
    char        map [FORM_CODES];
    char        *mem;
```

```
    int        found;
    int        length;
    int        code;
    int        index;

/* scan the possible choices */
    found = 0;
    for (index = 0; index < FORM_CODES; index++)
        if (set [index])
        {

/* construct a text string for choice */
            length = strlen (FormNames [index]) + 8 + 1;
            choices [found] = mem = alloca (length);
            strcpy (mem, "\037\0010\037\005 - ");
            mem [2] = (char) ('1' + found);
            strcpy (mem + 8, FormNames [index]);

/* set the choice mapping */
            map [found] = (char) index;
            found++;
        }

/* get the user choice */
    code = pick_list (DrugQueries [num], 10, count, choices);
    if (code >= 0)
        return map [code];
    return code;
}

/**************************************************************
   check_choices Checks the choices available in a candidate drug list for a particular
   option, asking the user to pick if there are alternatives.  Those drugs
   with an option not picked by the user are eliminated from the returned
   list.
***************************************************************/ static DrugPtr check_choices (int num, short (*ask) (int, int, bool []),
                              DrugPtr list)
{
    bool       picks [FORM_CODES];
    DrugPtr    cur;
    DrugPtr    last;
    DrugPtr    next;
    int        count;
    int        code;

/* initialize the set of valid choices */
    memset (picks, FALSE, FORM_CODES);
    count = 0;

/* find all choices in drug list */
    for (cur = list; cur; cur = cur->Next)
        if (! picks [cur->Choices [num]])
        {
            /* flag another possible choice */
            picks [cur->Choices [num]] = TRUE;
            count++;
        }

/* check for choice available on this option */
    if (count > 1)
    {

/* check for choice previously made */
        code = QualifiersPicked [num];
        if (code < 0 || ! picks [code])
        {

/* find the user choice */
            code = ask (num, count, picks);
            QualifiersPicked [num] = (char) code;
        }

/* process the choice made by user */
        if (code >= 0)
        {

/* discard all other choices from list */
            last = NULL;
            cur = list;
            while (cur)
                if (cur->Choices [num] != (char) code)
                {
```

```c
                    /* delete this drug from the list */
                    next = cur->Next;
                    if (last)
                        last->Next = next;
                    else
                        list = next;
                    free (cur);

/* advance to next in list */
                    cur = next;
                }
                else
                {
                    /* set new last valid drug pointer */
                    last = cur;
                    cur = cur->Next;
                }
        }
        else
        {
            /* discard the entire list */
            next = list;
            while (cur = next)
            {
                next = cur->Next;
                free (cur);
            }

/* terminate the session at user request */
            SessionAborted = 1;
            list = NULL;
        }
    }

/* return the valid drug list */
    return list;
}

/***************************************************************
  select_drug

Handles the actual drug selection based on the drug class
    recommendations generated by the knowledgebase, possibly executing
    other knowledgebases in the process.
****************************************************************/ short select_drug (bool hold, char comps [CLASS_COMPONENTS])
{
    char        need [CLASS_COMPONENTS];
    char        miss [CLASS_COMPONENTS];
    char        tcn [CLASS_NUMBER + 1];
    char        qual [QUALIFIER_COUNT];
    char        buf [11];
    int         class [5];
    DrugPtr     first;
    DrugPtr     last;
    DrugPtr     cur;
    char        *text;
    int         ind;
    int         num;
    int         sub;
    int         infant;
    int         child;
    int         adult;
    int         age;
    int         check;
    int         tot;
    char        match;

/* check for a valid completed session */
    RecommendCount = 0;
    if (! SessionAborted)
    {
        /* convert "antipyretic" to "analgesic" */
        num = register_component (FALSE, "antipyretic");
        sub = register_component (FALSE, "analgesic");
        for (ind = 0; ind < CLASS_COMPONENTS && comps [ind] >= 0; ind++)
            if (comps [ind] == (char) num)
                comps [ind] = (char) sub;

/* eliminate duplicates of "analgesic" */
        num = sub;
        for (ind = 0; ind < CLASS_COMPONENTS && comps [ind] >= 0; ind++)
```

```c
        if (comps [ind] == (char) num)
        {
            comps [ind] = (char) sub;
            sub = -1;
        }
}

/* make sure the indices are ordered */
order_components (comps);
memcpy (need, comps, CLASS_COMPONENTS);

/* initialize flags for TCNs tried */
for (ind = 0; ind < TCNCount; ind++)
    TCNTable [ind].Tried = FALSE;

/* find the individual drug possibilities */
memset (qual, 0, QUALIFIER_COUNT);
memset (miss, -1, CLASS_COMPONENTS);
tot = 0;
ReportFail = FALSE;
while (need [0] >= 0 && ! SessionAborted)
{
    /* find match in the class table */
    num = match_class (need, qual, ModuleNumber);
    if (num >= 0)
    {
        /* set up to access the drug database */
        d4select (DrugDatabase);
        i4select (DrugUseIndex);

/* look up the corresponding drugs */
        memcpy (tcn, TCNTable [num].Code, CLASS_NUMBER);
        tcn [CLASS_NUMBER] = 0;
        if (! d4seek_str (TCNTable [num].Code))
        {
            /* initialize the candidate drug list */
            first = last = NULL;

/* check all drugs in the class */
            while
              (memcmp (tcn, f4str (Drug_TcnCode), CLASS_NUMBER) == 0)
            {
                /* set default age cutoff values */
                infant = 3;
                child = 6;
                adult = 12;

/* check for non-standard ranges */
                if (text = skip_blanks (f4str (Drug_Age)))
                {
                    /* convert to a numeric value */
                    age = atoi (text);
                    if (age != 99)
                    {
                        /* substitute for the appropriate default */
                        if (f4char (Drug_InfantOK) == 'Y')
                        {
                            if (infant > age)
                                infant = age;
                        }
                        else if (f4char (Drug_ChildOK) == 'Y')
                        {
                            if (child > age)
                                child = age;
                        }
                        else
                            if (adult > age)
                                adult = age;
                    }
                }

/* screen out drugs inappropriate to age group */
                if ((UserAge >= infant && UserAge < child &&
                  f4char (Drug_InfantRec) == 'Y') ||
                  (UserAge >= child && UserAge < adult &&
                  f4char (Drug_ChildRec) == 'Y') ||
                  (UserAge >= adult && f4char (Drug_AdultRec) == 'Y'))
                {
                    /* record basic drug information in structure */
                    cur = (DrugPtr) malloc (sizeof (DrugRec));
                    cur->Next = NULL;
                    memcpy (cur->DrugID, f4str (Drug_DrugID),
                      DRUG_IDENT);
```

```c
        memset (cur->Choices, 0, DRUG_CHOICES);

/* fill in the yes/no values */
        if (f4char (Drug_AlcohFree) == 'Y')
            cur->Choices [DRUG_ALCFREE] = TRUE;
        if (f4char (Drug_SugarFree) == 'Y')
            cur->Choices [DRUG_SUGFREE] = TRUE;
        if (f4char (Drug_ExtraStren) == 'Y')
            cur->Choices [DRUG_EXTRASTREN] = TRUE;
        if (f4char (Drug_TimeDelay) == 'Y')
            cur->Choices [DRUG_TIMEDELAY] = TRUE;
        if (f4char (Drug_NightTime) == 'Y')
            cur->Choices [DRUG_NIGHTTIME] = TRUE;

/* convert the dose form code */
        text = f4str (Drug_DoseForm);
        for (ind = 0; ind < FormCount; ind++)
            if (memcmp (text, FormCodes [ind], 2) == 0)
                break;
        cur->Choices [DRUG_DOSEFORM] = (char) ind;
        /* print debug information */
        if (DebugFlag)
        {
            char    text [80];

copy_trunc (text, f4str (Drug_DrugName), 79);
            printf ("Found \"%s\": ", text);
            for (ind = 0; ind < DRUG_CHOICES; ind++)
                printf ("%1d", cur->Choices [ind]);
            printf ("\n");
        }

/* link the information into list */
        if (last)
            last->Next = cur;
        else
            first = cur;
        last = cur;
    }

/* advance to the next drug */
    if (d4skip (1L))
        break;
}

/* check for at least one choice found */
if (first)
{

/* eliminate choices among the candidate drugs */
    for (ind = 0; ind < DRUG_CHOICES; ind++)
        first = check_choices (ind, ind == DRUG_DOSEFORM ?
            ask_doseform : ask_preference, first);

/* make sure one was usable */
    if (first)
    {

/* save the drug and class identifier */
        class [RecommendCount] = num;
        memcpy (RecommendList [RecommendCount++],
            first->DrugID, DRUG_IDENT);

/* delete matched components from list */
        check = 0;
        while ((match = TCNTable [num].Components
            [check++]) >= 0)
                for (ind = 0; ind < CLASS_COMPONENTS; ind++)
                    if (need [ind] == match)
                        need [ind] = -1;

/* reorder the remaining components */
        order_components (need);
            }
        }
    }
}
else
{

/* flag match failure */
    ReportFail = TRUE;

/* eliminate a component drug and retry */
    miss [tot++] = need [0];
    need [0] = -1;
    order_components (need);
}
```

```c
        }
    } if ! DEMO_VERSION

/* force hold for high blood pressure */
    if (UserHighPressure)
        hold = TRUE;

/* check for printing a report */
    if (SessionAborted > 0)
    {
        /* tell the user the session has been terminated */
        link_item ((ItemPtr) &AbortSessionScreen);
        draw_item ((ItemPtr) &AbortSessionScreen);
    }
    else
    {
        /* tell the user the pharmacist will be with her */
        link_item ((ItemPtr) &PrintingInfoScreen);
        draw_item ((ItemPtr) &PrintingInfoScreen);

/* generate the user report */
        print_report (hold, ReportFail, comps, RecommendCount, RecommendList);
        HavePrinted = TRUE;
    }

/* access the utilization file */
    open_util ();
    d4select (UtilDatabase);
    i4select (UtilIndex);

/* convert user identifier number to text */
    sprintf (buf, "%010ld", CurrentUserID);

/* check for aborted session */
    if (SessionAborted)
    {
        /* set the data for an aborted session */
        f4r_str (Util_UserID, buf);
        f4r_str (Util_Serial, SessionSerial);
        f4r_str (Util_RecCode, "999800");
        f4r_str (Util_RecProd,
            SessionAborted > 0 ? "USER ABORT" : "SYS ABORT");
        f4r_str (Util_Version, KBTable [ModuleNumber].Version);
        f4r_str (Util_BackedUp, " ");

/* append the new record to the database */
        d4append ();
    }
    else
    {
        /* check for pharmacist attention required */
        if (hold)
        {
            /* record "no select" in database */
            f4r_str (Util_UserID, buf);
            f4r_str (Util_Serial, SessionSerial);
            f4r_str (Util_RecCode, "999801");
            f4r_str (Util_RecProd, "NO SELECT");
            f4r_str (Util_Version, KBTable [ModuleNumber].Version);
            f4r_str (Util_BloodP1, UserTopPressure);
            f4r_str (Util_BloodP2, UserBottomPressure);
            f4r_str (Util_BPDate, UserAccess);
            f4r_str (Util_BackedUp, " ");

/* append the new record to the database */
            d4append ();
        }

/* check for failure on selecting drugs */
        if (ReportFail)
            while (--tot >= 0)
            {
                /* record missed component in database */
                f4r_str (Util_UserID, buf);
                f4r_str (Util_Serial, SessionSerial);
                strcpy (buf, "9999");
                sprintf (buf + 4, "%02d", miss [tot]);
```

```
            f4r_str (Util_RecCode, buf);
            f4r_str (Util_RecProd, ComponentNames [miss [tot]]);
            f4r_str (Util_Version, KBTable [ModuleNumber].Version);
            f4r_str (Util_BloodP1, UserTopPressure);
            f4r_str (Util_BloodP2, UserBottomPressure);
            f4r_str (Util_BPDate, UserAccess);
            f4r_str (Util_BackedUp, " ");

/* append the new record to the database */
            d4append ();
        }

/* record all recommendations in database */
        for (ind = 0; ind < RecommendCount; ind++)
        {

/* set the data for a result recommendation */
            f4r_str (Util_UserID, buf);
            f4r_str (Util_Serial, SessionSerial);
            f4r_str (Util_RecCode, TCNTable [class [ind]].Code);
            f4r_str (Util_RecProd, RecommendList [ind]);
            f4r_str (Util_Version, KBTable [ModuleNumber].Version);
            f4r_str (Util_BloodP1, UserTopPressure);
            f4r_str (Util_BloodP2, UserBottomPressure);
            f4r_str (Util_BPDate, UserAccess);
            f4r_str (Util_BackedUp, " ");

/* append the new record to the database */
            d4append ();
        }
    }

/* access the utilization detail file */
    d4select (UtilDetDatabase);
    i4select (UtilDetIndex);

/* record all user responses in database */
    for (ind = 0; ind < QueryCount; ind++)
    {

* set the data for a query */
        f4r_str (UtilDet_Serial, SessionSerial);
        f4r_str (UtilDet_Question, SessionRecord [ind] [0]);
        f4r_str (UtilDet_Answer, SessionRecord [ind] [1]);

/* append the new record to the database */
        d4append ();
    }

/* close the files to save information */
    close_util ();

#endif

/* check for debug display enabled */
    if ((ScreenFlag || DEMO_VERSION) && ! SessionAborted)
    {
        char        drugs [161];
        char        types [81];
        int         height;
        int         length;
        int         add;
        int         bias;

/* set the lead text string */
        if (hold)
            RecommendLeadText.Text = "Based on your responses, we "
                "recommend\n\037\001further consultation\037\005 before "
                "taking any medications.";
        else
            RecommendLeadText.Text = "Based on your responses, we "
                "recommend\nthe medications described below.";
        height = NORMTEXT_VERT * 6 + 56;

/* form component name string */
        strcpy (types, "\037\002");
        length = 2;
        for
        (ind = 0; ind < CLASS_COMPONENTS && (num = comps [ind]) >= 0; ind++)
        {
            add = strlen (ComponentNames [num]);
            if (length + add > 79)
                add = 79 - length;
            if (add > 0)
            {
                if (length <= 40 && length + add >= 40)
                {
                    types [length - 1] = '\n';
```

```c
            height += NORMTEXT_VERT;
        }
        memcpy (types + length, ComponentNames [num], add);
        length += add;
        types [length++] = '/';
    }
}
if (length > 0)
    length--;
types [length] = 0;

/* set up to access the drug database */
d4select (DrugDatabase);
i4select (DrugIndex);

/* form drug name string */
strcpy (drugs, "\037\002");
length = 2;
for (ind = 0; ind < RecommendCount; ind++)
{
    d4seek_str (RecommendList [ind]);
    text = f4str (Drug_DrugName);
    add = strlen (text);
    while (add > 0 && text [add - 1] == ' ')
        add--;
    if (length + add > 159)
        add = 159 - length;
    if (add > 0)
    {
        memcpy (drugs + length, text, add);
        length += add;
        drugs [length++] = '\n';
        height += NORMTEXT_VERT;
    }
}
if (length > 0)
    length--;
drugs [length] = 0;

/* set the text string linkages */
RecommendCompsText.Text = types;
RecommendDrugsText.Text = drugs;

/* set the vertical positioning */
bias = (RecommendScreen.Item.Bounds.Bottom -
    RecommendScreen.Item.Bounds.Top - height) >> 1;
RecommendLeadText.Item.Bounds.Top =
    RecommendLeadText.Item.Bounds.Bottom = bias;

/* tell the user the session has been terminated */
link_item ((ItemPtr) &RecommendScreen);
draw_item ((ItemPtr) &RecommendScreen);
wait_key (300);
}

/* set up the template screen */
init_template ();

/* take successful return */
return 0;
}
```

APPENDIX 8

```c
#include <graph.h>
#include <stdio.h>
#include <stdlib.h>
#include <string.h>
#include <ctype.h>
#include <time.h>
#include <sys\types.h>
#include <fcntl.h>
#include <io.h>
#include "d4base.h"
#include "oem.h"

#include "data.h"
include "screen.h"
#include "defs.h"
#include "vars.h"

/*****************************************************************
  new_line

Advances the print output to the next line.
*****************************************************************/ static void new_line (void)
{
```

```c
    /* check for border characters needed */
    if (MarginChar != ' ')
    {

/* print left border character if appropriate */
        if (CurrentPosition == 0)
        {
            putc (MarginChar, stdprn);
            CurrentPosition++;
        }

/* fill to the right border with blanks */
        while (CurrentPosition < 79)
        {
            putc (' ', stdprn);
            CurrentPosition++;
        }

/* print the border character */
        putc (MarginChar, stdprn);
    }

/* advance to a new line of print output */
    putc ('\n', stdprn);
    CurrentPosition = 0;
    LineNumber++;
}

/************************************************************
  print_margin

Prints the spaces required for the left margin at the start of an output
    line, including the specified indentation.
************************************************************/ static void print_margin (short indent)
{
    int         index;
    /* check for end of page reached */
    if (LineNumber >= PageLines)
    {

/* force top of page before printing */
        putc (FORMFEED, stdprn);
        LineNumber = 0;
    }

/* print left border character if needed */
    if (MarginChar != ' ')
    {
        putc (MarginChar, stdprn);
        CurrentPosition++;
    }

/* fill with blanks to the left margin */
    for (index = CurrentPosition; index < LeftMargin; index++)
        putc (' ', stdprn);

/* fill extra indentation level of blanks */
    for (index = 0; index < indent; index++)
        putc (' ', stdprn);

/* set actual output position */
    CurrentPosition = LeftMargin + indent;
}

/************************************************************
  print_blanks

Prints a specified number of blanks to the output line, stopping when
    the end of the line is reached.
************************************************************/ static void print_blanks (short count)
{
    /* handle indentation at start of line */
    if (count > 0 && CurrentPosition == 0)
        print_margin (0);

/* print the actual blanks */
    while (count-- > 0 && CurrentPosition < RightMargin)
    {
        putc (' ', stdprn);
        CurrentPosition++;
    }
}
```

```c
/****************************************************************
  print_character Prints a character a specified number of times to the output line,
    stopping when the end of the line is reached.
****************************************************************/
static void print_character (short count, char chr)
{
    /* handle indentation at start of line */
    if (count > 0 && CurrentPosition == 0)
        print_margin (0);
    /* print the actual blanks */
    while (count-- > 0 && CurrentPosition < RightMargin)
    {
        putc (chr, stdprn);
        CurrentPosition++;
    }
}

/****************************************************************
  print_word

Prints a word to the current output line if space remains, otherwise
    advances to the next output line and then prints it.
****************************************************************/
static void print_word (short length, short indent, char *word)
{
    /* handle left margin */
    if (CurrentPosition == 0)
        print_margin (0);

/* check space available on line */
    if (CurrentPosition + length > RightMargin)
    {
        /* advance to the next line */
        new_line ();
        print_margin (indent);
    }

/* print the actual word */
    fwrite (word, length, 1, stdprn);
    CurrentPosition += length;
}

/****************************************************************
  print_text

Prints a text string for the user report, breaking it at the right
    margin if necessary.
****************************************************************/
static void print_text (short indent, char *text)
{
    short    length;
    char     chr;

/* scan a word from the text string */
    while (*text && (length = strcspn (text, " -\n")) >= 0)
    {
        /* check for break character included in word */
        chr = text [length];
        if (chr == '-')
            length++;

/* print the word */
        print_word (length, indent, text);

/* handle newline character as terminator */
        if (chr == '\n')
        {
            new_line ();
            length++;
        }

/* print out any trailing blanks individually */
        text += length;
        for (length = 0; text [length] == ' '; length++);
        print_blanks (length);
        text += length;
    }
}
```

```
/****************************************************************
  print_control Prints a control string, without counting the characters in the current
    line.
****************************************************************/ static void print_control (char *text)
{
    int        length;

/* check for controls enabled */
    if (PrinterControl)
    {

/* print the control string */
        length = strlen (text);
        if (length)
            fwrite (text, length, 1, stdprn);
    }
}

/****************************************************************
  print_header Prints the header for a page of the user report.
****************************************************************/ static void print_header (int page, int total, char *serial)
{
    char       text [14];

/* format page number */
    strcpy (text, "Page ");
    itoa (page, text + 5, 10);
    strcat (text, " of ");
    itoa (total, text + strlen (text), 10);

/* print serial number and copyright */
    print_text (0, serial);
    print_blanks (10);
    print_text (0, "(C) MedScreen, Inc. 1991");
    print_blanks
      (RightMargin - LeftMargin - 17 - 24 - 10 - 2 - strlen (text));

/* finish with the right-justified page number */
    print_text (0, text);
    new_line ();
    new_line ();
}

/****************************************************************
  print_name

Prints the user name in standard form, with only the initial letter of
    each name capitalized.
****************************************************************/ static void print_name ()
{
    char       text [16];

/* convert and print first name */
    strcpy (text, UserFirstName);
    strlwr (text + 1);
    print_text (0, text);
    print_blanks (1);

/* convert and print last name */
    strcpy (text, UserLastName);
    strlwr (text + 1);
    print_text (0, text);
}

/****************************************************************
  blank_string Tests a string to determine if it is composed entirely of blanks.
****************************************************************/ static bool blank_string (char *text)
{
    char       chr;

while (chr = *text++)
```

```c
            if (chr != ' ')
                return FALSE;
    return TRUE;
}

/****************************************************************
    print_query Prints a query and response from the user.
****************************************************************/
static void print_query (bool show, bool fail, QueryPtr query, char resp [4])
{
    char        text [200];
    ReplyPtr    reply;
    char        *question;
    char        *mark;
    char        *answer;
    int         hold;
    bool        reject;

/* set the question text pointer */
    question = query->Text;
    question += strlen (question) + 1;

/* discard text to embedded color change */
    if (mark = strchr (question, '\037'))
        question = mark + 3;

/* copy the actual text to the buffer */
    strcpy (text, question);
    question = mark = text;
    while (mark = strchr (mark, '\013'))
        *mark++ = '/';

/* check type of question */
    reject = FALSE;
    if (query->Type == QUERY_NOYES || query->Type == QUERY_YESNO ||
     query->Type == QUERY_PRESSURE)
    {
        /* find answer chosen for no/yes question */
        if (memcmp (resp, "0000", 4) == 0)
        {
            /* flag possible reject response if "yes" expected */
            answer = "no";
            if (query->Type == QUERY_YESNO)
                reject = query->Reject;
        }
        else
        {
            /* flag possible reject response if "no" expected */
            answer = "yes";
            if (query->Type == QUERY_NOYES || query->Type == QUERY_PRESSURE)
                reject = query->Reject;
        }
    }
    else
    {
        /* find the reply actually chosen */
        answer = "unknown";
        for (reply = query->Replys; reply; reply = reply->Next)
            if (memcmp (resp, reply->Code, 4) == 0)
            {
                /* scan past leading value */
                answer = reply->Text;
                if (query->Type == QUERY_VALUE)
                    answer += strlen (answer) + 1;

/* scan past selection header */
                if (*answer == '\037')
                    answer += 6;

/* flag possible reject response */
                reject = reply->Reject;
                break;
            }
    }

/* set bold text if failure response */
    if (fail && reject)
        print_control (PrintBoldOn);
```

```c
    /* print the actual question */
    if (show)
    {
        RightMargin -= 20;
        print_text (2, question);
        RightMargin += 20;
    }

/* append the answer chosen */
    hold = LeftMargin;
    LeftMargin = RightMargin - 18;
    if (CurrentPosition)
        print_blanks (LeftMargin - CurrentPosition);
    print_text (2, answer);
    LeftMargin = hold;

/* clear bold text if failure response */
    if (fail && reject)
        print_control (PrintBoldOff);
    new_line ();
}

/****************************************************************
  print_components Prints the list of recommended component medicine names, with the
    appropriate punctuation and articles.
****************************************************************/ static void print_components (char term, char comps [CLASS_COMPONENTS])
{
    char    name [64];
    int     off;
    int     length;
    char    lead;
    char    trail;

/* process all component medicines */
    for (off = 0; off < CLASS_COMPONENTS && comps [off] >= 0; off++)
    {
        /* copy the name string */
        strcpy (name, ComponentNames [comps [off]]);

/* print the leading article */
        lead = name [0];
        if (lead >= 'a' && lead <= 'z')
            lead += (char) ('A' - 'a');
        if (lead == 'A' || lead == 'E' || lead == 'I' ||
            lead == 'O' || lead == 'U')
            print_text (0, "an ");
        else
            print_text (0, "a ");

/* tack on the trailing punctuation */
        trail = ',';
        if (off >= CLASS_COMPONENTS - 1 || comps [off + 1] < 0)
            trail = term;
        length = strlen (name);
        name [length++] = trail;

/* also append conjunction if appropriate */
        if ((off < CLASS_COMPONENTS - 2 &&
             comps [off + 1] >= 0 && comps [off + 2] < 0) ||
            (off == CLASS_COMPONENTS - 2 && comps [off + 1] >= 0))
        {
            strcpy (name + length, " and");
            length += 4;
        }

/* print out the component name */
        name [length++] = ' ';
        name [length] = 0;
        print_text (0, name);
    }
}

/****************************************************************
  print_monograph Prints the monograph for the current drug database record.
****************************************************************/ static void print_monograph (void)
{
    char    buffer [2048];
```

```c
    char        mono [6];
    char        *scan;
    char        *mark;
    int         code;

/* retrieve the monograph database record */
    memcpy (mono, f4str (Drug_MonoID), 6);
    code = d4select (MonoDatabase);
    code = i4select (MonoIndex);
    if (d4seek_str (mono) == 0)
    {
        /* convert the monograph text */
        strcpy (buffer, f4str (Mono_MonoID));
        strcpy (buffer, f4str (Mono_Abstract));
        code = m3read (Mono_MonoText, d4recno (), buffer, 2047);
        scan = buffer;
        while (mark = strchr (scan, '\015'))
        {
            *mark = ' ';
            scan = mark;
        }

/* print the text to the listing */
        print_text (0, buffer);
    }
}

/***************************************************************
  print_drug

Prints the drug name line, including price and location information.
***************************************************************/ static void print_drug (void)
{
    char        name [41];
    char        add [41];
    char        *text;
    int         len;

/* retrieve the actual name */
    strncpy (name, f4str (Drug_DrugName), 40);
    name [40] = 0;

/* check for price information to be printed */
    add [0] = 0;
    if (ModuleTable [ModuleNumber].Price)
    {
        /* check for price actually provided */
        text = f4str (Drug_Price);
        if (text = skip_blanks (text))
        {
            /* generate leading format characters */
            strcpy (add, "  $");
            if (*text == '.')
                strcat (add, "0");

/* append the actual price */
            strcat (add, text);

/* check for size provided */
            text = f4str (Drug_PkgSize);
            if (text = skip_blanks (text))
            {
                /* generate size qualification */
                strcat (add, " per ");
                strcat (add, text);
            }
        }
    }

/* check for location to be printed */
    if (ModuleTable [ModuleNumber].Location)
    {
        /* check for location actually provided */
        text = f4str (Drug_Location);
        if (! blank_string (text))
        {
            /* check for price information present */
            if (add [0])
                strcat (add, "  ");
```

```c
        /* append the location information */
        strcat (add, text);
    }
}

/* truncate drug name text if necessary */
len = RightMargin - CurrentPosition - strlen (add) - 1;
if (len < 0)
    len = 0;
if (len < 40)
    name [len] = 0;

/* print out the information */
print_text (0, name);
print_text (0, add);

/* advance to the next output line */
new_line ();
}

/***************************************************************
    print_comment Prints a comment line, if defined.
***************************************************************/ static void print_comment (char *text)
{
    CommentPtr   cur;

/* scan list to find this comment */
    for (cur = CommentList; cur; cur = cur->Next)
        if (cur->Code [0] == text [0] && cur->Code [1] == text [1])
        {
            /* print the comment text */
            print_text (0, cur->Text);
            new_line ();
            break;;
        }
}

/***************************************************************
    print_date

Prints the current date in text form, optionally capitalizing the month.
***************************************************************/ static void print_date (bool caps)
{
    char    buffer [10];
    int     num;
    int     off;

/* decode the current month number */
    num = 0;
    if (SessionSerial [4] == '1')
        num = 10;
    num += SessionSerial [5] - '0';

/* convert month number to text */
    strcpy (buffer, MonthText [num - 1]);
    if (caps)
        strupr (buffer);
    print_text (0, buffer);

/* print the day number */
    print_blanks (1);
    off = 0;
    if (SessionSerial [6] != '0')
        buffer [off++] = SessionSerial [6];
    buffer [off++] = SessionSerial [7];
    buffer [off++] = ',';
    buffer [off++] = ' ';
    buffer [off] = 0;
    print_text (0, buffer);

/* print the complete year number */
    memcpy (buffer, SessionSerial, 4);
    buffer [4] = 0;
    print_text (0, buffer);
}
```

```
/*************************************************************
   print_pharmacy Prints the pharmacy header information.
*************************************************************/ static void print_pharmacy (void)
{
    /* generate pharmacy name line */
    print_text (0, StoreName);
    new_line ();

/* include address lines if present */
    if (! blank_string (StoreAddress1))
    {
        print_text (0, StoreAddress1);
        new_line ();
    }
    if (! blank_string (StoreAddress2))
    {
        print_text (0, StoreAddress2);
        new_line ();
    }

/* include city, state, and zip if present */
    if (! blank_string (StoreCity))
    {
        print_text (0, StoreCity);
        print_text (0, ", ");
        print_text (0, StoreState);
        print_blanks (1);
        print_text (0, StoreZip);
        new_line ();
    }
}

/*************************************************************
   position_coupon Positions to the bottom of the current page and prints a separator line,
       or to the top of the next page with no separator, in preparation for
       printing a coupon or message.
*************************************************************/ static void position_coupon (void)
{
    /* check space on page */
    if (LineNumber + 17 > PageLines)
    {
        /* skip to top of next page */
        putc (FORMFEED, stdprn);
        LineNumber = 0;
    }
    else
    {
        /* skip to bottom of page */
        while (LineNumber < PageLines - 17)
            new_line ();

/* print separator line */
        print_character (80, '-');
        new_line ();
    }
}

/*************************************************************
   print_report

Prints the report for the user, with a leading page of general
       information followed by an additional page of information specific to
       each recommended drug.
*************************************************************/ void print_report (bool warn, bool fail, char comps [], int count,
                   char drugs [] [6])
{
    char       serial [18];
    char       buffer [80];
    char       *text;
    FILE       *file;
    QueryPtr   query;
    QueryPtr   link;
```

```
int     child;
int     adult;
int     age;
int     index;
int     num;
bool    show;
bool    flag;

/* check for prior sessions in this batch */
if (HavePrinted)
{
    /* separate reports with a page eject */
    putc (FORMFEED, stdprn);
}
else
{
    /* initialize the printer */
    if (PrinterControl)
        print_control (PrintInit);
}

/* print warning text file */
if (warn || fail || SessionAborted)
{
    strcpy (buffer, DataPath);
    strcat (buffer, "\\ATTENT");
    if (file = fopen (buffer, "r"))
    {
        while (fgets (buffer, 80, file))
            fwrite (buffer, strlen (buffer), 1, stdprn);
        fclose (file);
        putc (FORMFEED, stdprn);
    }
}

/* initialize the listing controls */
CurrentPosition = 0;
LeftMargin = 4;
MarginChar = ' ';
LineNumber = 0;

/* generate serial number in output format */
serial [0] = '#';
memcpy (serial + 1, SessionSerial, 13);
serial [9] = serial [14] = '-';
serial [15] = SessionSerial [13];
serial [16] = SessionSerial [14];
serial [17] = 0;

/* print the initial page header */
print_header (1, count + 1, serial);

/* print pharmacy header information */
print_pharmacy ();

/* print leading text message */
new_line ();
print_text (0, "This computerized recommendation for a non-prescription "
    "medication was prepared on ");

/* print current date in text form */
print_date (FALSE);
print_text (0, " especially for:\n\n");

/* print the user name line */
LeftMargin = 8;
print_name ();
new_line ();

/* print remaining standard text */
print_text (0, "\nThis recommendation is based on the following"
    " information that has been provided for or by ");
print_name ();
print_text (0, " on this day.  Please review the following information.  "
    "If any of it is not accurate DO NOT TAKE THE SUGGESTED MEDICATION.\n");
LeftMargin = 12;

/* check for warning on young patient */
if ((warn || fail) && UserAge < 6)
    print_control (PrintBoldOn);

/* print birth and gender */
print_text (0, UserGender == 1 ? "\nFemale" : "\nMale");
print_text (0, ", born ");
print_text (0, MonthText [atoi (UserMonthText) - 1]);
print_text (0, ", ");
```

```
print_text (0, UserYearText);

/* clear warning on young patient */
if ((warn || fail) && UserAge < 6)
    print_control (PrintBoldOff);

/* check for blood pressure known */
if (UserTopPressure [0] && UserBottomPressure [0])
{

/* print leading blanks */
    print_text (0, "    ");

/* check for warning on blood pressure */
    if ((warn || fail) && UserHighPressure)
        print_control (PrintBoldOn);

/* print recent blood pressure reading */
    print_text (0, "Blood pressure ");
    print_text (0, UserTopPressure);
    print_text (0, " / ");
    print_text (0, UserBottomPressure);

/* clear warning on blood pressure */
    if ((warn || fail) && UserHighPressure)
        print_control (PrintBoldOff);

}

/* finish the general information line */
new_line ();
new_line ();

/* print the questions and responses */
for (index = 0; index < QueryCount; index++)
{

/* check for question to be displayed on line */
    show = (bool) (index <= 0 || memcmp
        (SessionRecord [index] [0], SessionRecord [index - 1] [0], 4) != 0);

/* find this query in current module */
    for (query = KBTable [KBRecord [index]].Queries; query;
        query = query->Next)
            if (memcmp (SessionRecord [index] [0], query->Code, 4) == 0)
            {

/* check for linked queries */
                flag = warn;
                for (link = query->Link; flag && link && link != query;
                    link = link->Link)
                {

/* find linked query in list */
                    for (num = 0; num < QueryCount; num++)
                        if (memcmp
                            (SessionRecord [num] [0], link->Code, 4) == 0)
                        {

/* allow warning flag only if same response */
                            if (memcmp (SessionRecord [num] [1],
                                SessionRecord [index] [1], 4) != 0)
                            {
                                flag = FALSE;
                                break;
                            }
                        }
                }

/* print the query line */
                print_query (show, flag, query, SessionRecord [index] [1]);
            }
}

/* check for an aborted session */
LeftMargin = 4;
if (SessionAborted)
{

/* print aborted session message */
    print_control (PrintBoldOn);
    print_text (0, "\nThis session was aborted due to a problem in the "
        "MedScreen data files.  Please report this result to MedScreen "
        "personnel.");
    print_control (PrintBoldOff);

}
else
{
```

```c
/* print the recommendation */
print_text (0, "\nBased on this information we are recommending ");
if (warn || fail)
    if (comps [0] < 0)
        print_text (0, "further consultation.");
    else
        print_text (0, "further consultation before using ");
print_components ('.', comps);
if (fail)
{
    print_control (PrintBoldOn);
    print_text
        (0, " Medications could not be found for all of these.\n");
    print_control (PrintBoldOff);
}

/* print pharmacist signature line */
print_text (0, "\n\nThis evaluation completed by "
"_____ Pharmacist");

/* handle printing of recommended drugs */
for (index = 0; index < count; index++)
{

/* advance to the next page */
    putc (FORMFEED, stdprn);
    LineNumber = 1;
    CurrentPosition = 0;
    print_header (index + 2, count + 1, serial);

/* print the drug header */
    new_line ();
    LeftMargin = 4;
    print_text (0, "Suggested Medication(s)\n\n");

/* retrieve the drug information */
    d4select (DrugDatabase);
    i4select (DrugIndex);
    d4seek_str (drugs [index]);

/* print the actual drug name */
    print_drug ();

/* check generic drug linkage */
    text = f4str (Drug_GenLink);
    if (! blank_string (text))
    {

/* print the generic drug information */
        copy_trunc (buffer, text, 6);
        if (! d4seek_str (buffer))
            print_drug ();

/* restore actual drug information */
        d4seek_str (drugs [index]);
    }

/* set default age cutoff values */
    child = 6;
    adult = 12;

/* check for non-standard ranges */
    if (text = skip_blanks (f4str (Drug_Age)))
    {

/* convert to a numeric value */
        age = atoi (text);
        if (age != 99)
        {

/* substitute for the appropriate default */
            if (f4char (Drug_InfantOK) != 'Y')
                if (f4char (Drug_ChildOK) == 'Y')
                {
                    if (child > age)
                        child = age;
                }
                else
                    if (adult > age)
                        adult = age;
        }
    }

/* print the dosage information */
    new_line ();
    text = f4str (UserAge < child ? Drug_InfantDose :
        (UserAge < adult ? Drug_ChildDose : Drug_AdultDose));
    print_text (0, text);
    new_line ();
```

```c
new_line ();

/* print the warning message if given */
text = f4str (Drug_Warning);
if (! blank_string (text))
{
    print_text (0, text);
    new_line ();
    new_line ();
}

/* print the monograph information */
print_text (0, "Please be aware of and observe the following "
    "precautions:\n");
print_monograph ();
new_line ();

/* print the comment lines if given */
print_comment (f4str (Drug_Msg1));
print_comment (f4str (Drug_Msg2));

/* check if printing coupons */
LeftMargin = 0;
if (ModuleTable [ModuleNumber].Coupon)
{
    /* check if discount specified */
    text = f4str (Drug_Coupon);
    if (text = skip_blanks (text))
    {
        /* position for printing coupon */
        position_coupon ();

/* print the coupon upper bar */
        new_line ();
        print_character (80, '*');
        new_line ();

/* set up for actual coupon text */
        LeftMargin = 8;
        RightMargin = 71;
        MarginChar = '*';
        new_line ();
        new_line ();
        new_line ();

/* check for pharmacy name given */
        if (! blank_string (StoreName))
        {
            /* print coupon store leader */
            print_text (0, "THANK YOU FOR SHOPPING AT ");
            strcpy (buffer, StoreName);
            strupr (buffer);
            print_text (0, buffer);
            new_line ();
            new_line ();
        }

/* print the discount text */
        print_text (0, "THIS COUPON IS GOOD FOR A ");
        copy_trunc (buffer, text, 6);
        print_text (0, buffer);
        print_text (0, " DISCOUNT ON YOUR PURCHASE OF ");

/* copy the medicine name */
        copy_trunc (buffer, f4str (Drug_DrugName), 40);

/* check for size provided */
        text = f4str (Drug_PkgSize);
        if (text = skip_blanks (text))
        {
            /* generate size qualification */
            strcat (buffer, " (");
            strcat (buffer, text);
            text = buffer + strlen (buffer) - 1;
            while (*text == ' ')
                --text;
            strcpy (text + 1, " SIZE)");
        }

/* print the medicine name */
        strupr (buffer);
        text = buffer + strlen (buffer);
        *text++ = '.';
        *text = 0;
        print_text (0, buffer);
```

```c
            /* print the dating text */
            print_text (0, "\n\nTHIS COUPON IS VALID TODAY ONLY\n"
            "DATE ISSUED:  ");
            print_date (TRUE);
            print_text (0, ".\n\n\n\n");

/* restore standard settings */
            LeftMargin = 0;
            RightMargin = 80;
            MarginChar = ' ';

/* print the lower coupon bar */
            print_character (80, '*');
            new_line ();
        }
    }
    else if (ModuleTable [ModuleNumber].Message)
    {
        /* check for module text actually present */
        text = ModuleTable [ModuleNumber].Text;
        if (skip_blanks (text))
        {
            /* position for printing coupon */
            position_coupon ();

/* print the box upper bar */
            new_line ();
            print_character (80, '*');
            new_line ();

/* set up for actual message text */
            LeftMargin = 8;
            RightMargin = 71;
            MarginChar = '*';
            new_line ();

/* print the message text */
            print_text (0, text);
            new_line ();
            new_line ();

/* restore standard settings */
            LeftMargin = 0;
            RightMargin = 80;
            MarginChar = ' ';

/* print the lower coupon bar */
            print_character (80, '*');
            new_line ();
        }
    }
   }
  }
 }
} if INFO_VERSION

/****************************************************************
   print_information Prints the information about a particular drug for the user, adjusting
   the formatting to fit the page width.
****************************************************************/
void print_information (char *desc, long off)
{
    char       data [2048];
    FILE       *file;
    char       *text;
    char       *mark;
    ushort     num;

/* check for prior sessions in this batch */
    if (HavePrinted)
    {
        /* separate reports with a page eject */
        putc (FORMFEED, stdprn);

}
    else
    {
        /* initialize the printer */
        if (PrinterControl)
            print_control (PrintInit);
    }
```

```c
        /* initialize the listing controls */
        CurrentPosition = 0;
        LeftMargin = 6;
        MarginChar = ' ';
        LineNumber = 0;

/* open the narrative file and position */
        strcpy (data, DataPath);
        strcat (data, "\\MONO.DAT");
        file = fopen (data, "rb");
        if (file && fseek (file, off, SEEK_SET) == 0)
        {
            /* print pharmacy header information */
            new_line ();
            print_pharmacy ();

/* print name and leading text message */
            new_line ();
            print_text (0, desc);

/* print current date in text form */
            new_line ();
            new_line ();
            print_text (0, "This information printed ");
            print_text (0, _strdate (data));
            new_line ();
            new_line ();

/* loop for all records in this text */
            LeftMargin = 10;
            num = 0;
            while (fgets (data, 2048, file) && strncmp (data, "!!!!", 4) != 0)
            {
                /* check for embedded format changes */
                text = data;
                while (text && (mark = strchr (text, '~')))
                {
                    /* print to the format change */
                    *mark = 0;
                    print_text (0, text);

#if 0
                    /* set bold print on */
                    print_control (PrintBoldOn);
endif /* print to the next blank */
                    text = strchr (mark, ' ');
                    *mark = ' ';
                    if (text)
                        *text = 0;
                    print_text (0, mark);

#if 0
                    /* set bold print off */
                    print_control (PrintBoldOff);
endif /* continue checking for changes */
                    if (text)
                        *text = ' ';
                }

/* output remaining text */
                if (text)
                    print_text (0, text);
            }

/* close the file for return */
            fclose (file);

/* print template warning text */
            LeftMargin = 6;
            new_line ();
            print_text (0, "** DO NOT Keep Or Use Outdated Medication **\n");
            print_text (0, "Keep All Medication Out Of The Reach Of Children\n");

/* print template copyright text */
            new_line ();
            print_text (0, "Copyright (c) 1991 Facts and Comparisons");

/* flag printing done */
            HavePrinted = TRUE;
        }
    } endif
```

APPENDIX 9

```c
#define DEMO_VERSION    0
#define PROF_VERSION    0
#define INFO_VERSION    0
#include "version.h"

/*
    Data structure definitions used throughout the program.
*/ typedef unsigned char   bool;
typedef unsigned short  ushort;

#define TRUE            1
define FALSE           0 define STRING_MAX      256 define MODULE_COUNT    6
define KB_COUNT        7 define MAX_AUTOS       16 define MAX_QUERIES     50 define CLASS_NUMBER    6
define MAX_QUALIFIER   6
#define MAX_CLASSES     128
#define MAX_COMPONENTS  48
#define CLASS_COMPONENTS 8
#define MAX_DESCRIPTION 60
#define QUALIFIER_COUNT 4
define DRUG_IDENT      6 define STORE_NAME      61      /* field lengths for "STORE" database */
define STORE_ADDRESS   56
#define STORE_CITY      18
#define STORE_STATE     3
define STORE_ZIP       11 define QUERY_CHOICE    0       /* one of several choices */
define QUERY_SET       1       /* zero or more of several choices */
#define QUERY_AGE       2       /* age */
#define QUERY_GENDER    3       /* gender */
#define QUERY_VALUE     4       /* numeric value range */
#define QUERY_YESNO     5       /* yes or no */
#define QUERY_NOYES     6       /* no or yes */
#define QUERY_QUALIFY   7       /* current qualifier choice */
define QUERY_PRESSURE  8       /* blood pressure no or yes */ define RESPONSE_NO     1       /* no choice */
define RESPONSE_YES    2       /* yes choice */ define DRUG_ALCFREE    0       /* alcohol free flag */
define DRUG_SUGFREE    1       /* sugar free flag */
#define DRUG_EXTRASTREN 2       /* extra strength flag */
#define DRUG_TIMEDELAY  3       /* time delay flag */
#define DRUG_NIGHTTIME  4       /* night time flag */
#define DRUG_DOSEFORM   5       /* dose form code */
define DRUG_CHOICES    6       /* number of drug choice variables */ define FORM_CODES      40      /* maximum dose form codes recognized */ define ESC             0x1B    /* ESC key code */
define TAB             0x09    /* TAB key code */
define ENTER           0x00    /* ENTER key code */ define CURSOR          0x00    /* cursor key leading code */
define BACKSPACE       0x08    /* BACKSPACE key code */
#define BELL            0x07    /* BELL key code */
define FORMFEED        0x0C    /* FORMFEED key code */ define CURSOR_LEFT     0x14B   /* left arrow */
define CURSOR_RIGHT    0x14D   /* right arrow */
define DEL             0x153   /* DEL key code */ define SEPARATE_SKIP   10      /* pixel columns to skip around separator */ typedef struct {                /* therapeutic class information */
    char    Code [CLASS_NUMBER];     /* therapeutic class number */
    char    Qualifier [MAX_QUALIFIER];  /* qualifier code */
    char    Components [CLASS_COMPONENTS];  /* component medicines */
    short   Drugs;              /* number of drugs available in class */
```

```
    bool     Tried;      /* used in this recommendation flag */
    bool     Infant;     /* infant recommendation flag */
    bool     Child;      /* child recommendation flag */
    bool     Adult;      /* adult recommendation flag */
} TCNRec, *TCNPtr;

typedef struct {                    /* module information */
    bool     Single;     /* single ingredient flay */
    bool     Multiple;   /* multiple ingredient flag */
    bool     Coupon;     /* print coupons flag */
    bool     Price;      /* print price flag */
    bool     Location;   /* print location flag */
    bool     Message;    /* use message flag */
    char     Qualify [QUALIFIER_COUNT] [MAX_QUALIFIER];  /* qualifiers */
    char     *Text;      /* message text string */
} ModuleRec, *ModulePtr;

typedef struct _DR {                /* drug information */
    struct _DR  *Next;   /* next drug linkage */
    char     DrugID [DRUG_IDENT];    /* unique identifier */
    char     Choices [DRUG_CHOICES]; /* specific choice values */
} DrugRec, *DrugPtr;

typedef struct _RR {                /* reply information */
    struct _RR  *Next;   /* next reply linkage */
    char     Operator;   /* operator type */
    bool     Reject;     /* response disables selection flag */
    char     Code [4];   /* reply code */
    char     Text [2];   /* text of the reply */
} ReplyRec, *ReplyPtr;

typedef struct _QR {                /* query information */
    struct _QR  *Next;   /* next query linkage */
    char     Type;       /* query type code */
    char     Count;      /* number of replys specified */
    bool     Reject;     /* response may disable selection flag */
    short    Help;       /* help message index number */
    struct _QR  *Link;   /* linked query pointer */
    ReplyPtr Replys;     /* head of reply information list */
    char     Code [4];   /* query code */
    char     Text [2];   /* receiver and question text */
} QueryRec, *QueryPtr;

typedef struct {                    /* knowledgebase information */
    QueryPtr Queries;    /* query information list head */
    char     Version [4];    /* expected version number */
    char     File [20];      /* file name text string */
    char     Qualifier [20]; /* qualifier knowledgebase name */
} KBRec, *KBPtr;

typedef struct _CR {                /* comment code information */
    struct _CR  *Next;   /* next comment code linkage */
    char     Code [2];   /* actual code value */
    char     Text [2];   /* associated comment text */
} CommentRec, *CommentPtr;

typedef struct {
    short    Level;      /* priority level in print queue */
    char     *Name;      /* print file name string */
} PrintPacket;

/*
    Functions defined in ADVISOR.C
*/ extern short wait_key (short ticks);
extern void order_components (char *comps);
extern short register_component (short add, char *name);
extern TCNPtr find_class (char *code);
extern void copy_fill (char *dest, char *src, short size);
extern void copy_trunc (char *dest, char *src, short size);
extern char *skip_blanks (char *text);
extern bool get_line (bool skip, int size, FILE *file, char *text);
extern int format_text (char *str, int limit, TextPtr text);
extern void knowledgebase_path (char *name, char *path);
extern short invoke_inference (int num);
extern short ask_noyes (int help, char *query);
extern bool wait_printer (void);
extern void free_tree (ItemPtr tree);
extern ItemPtr build_choice (char format, char horz, char vert, char font,
                             int width, int code, char *text);
extern short pick_list (char *query, int help, short count, char *choices []);
extern int use_data (char *name);
extern int index_data (char *name);
extern int use_advert (char *name);

/*
```

```
    Functions defined in DINIT.C
*/ extern bool open_user (void);
extern bool open_advert (void);
extern bool open_printers (void);
extern bool configure_store (void);
extern bool open_mono (void);
extern bool configure_modules (void);
extern bool generate_classes (void);
extern bool index_drugs (void);
extern bool configure_doses (void);
extern bool configure_comments (void);
extern bool configure_miscellaneous (void);

/*
    Functions defined in DISPLAY.C
*/ extern bool push_clip (RectPtr rect);
extern bool pop_clip (void);
extern void set_font (short height, short width, char *font);
extern void text_font (short number);
extern void inset_rectangle (short vdif, short hdif, RectPtr rect);
extern struct xycoord color_extent (short extra, char *text);
extern void item_rectangle (ItemPtr item, RectPtr rect);
extern void solid_rectangle (short color, RectPtr rect);
extern void invert_cursor (InputPtr input);
extern void draw_item (ItemPtr item);
extern void print_centered (short ypos, char *string);
extern void display_logos (short top, short bottom, char *primary, char *secondary);
extern void init_screen (void);

/*
    Functions defined in INTER.C
*/ extern int set_query (int width, char *text);

/*
    Functions defined in ITEM.C
*/ extern void link_item (ItemPtr item);
extern short run_error (bool error, short time, ItemPtr item, char *text);
extern short run_items (short time, ItemPtr root, ItemPtr tree);
extern short run_template (short time, ItemPtr root);
extern short run_screen (short time, ItemPtr root);
extern void init_template (void);

/*
    Functions defined in PICTURE.C
*/ if 0 extern int retrieve_image (int first, int last, int file, long colors [16],
                char *image []);
extern int draw_image (short wipe, short time, long colors [16], char *image []);

else extern int draw_image (int first, int last, int file, int time);

endif

/*
    Functions defined in PRINT.C
*/ extern void print_report (bool warn, bool fail, char comps [], int count,
    char drugs [][6]);

if INFO_VERSION extern void print_information (char *desc, long off);

endif

/*
```

```c
    Functions defined in QINIT.C
*/ extern short input_queries (void);
extern short input_helps (void);

/*
    Functions defined in SELECT.C
*/ extern short select_drug (bool hold, char comps [CLASS_COMPONENTS]);

/*
    Functions defined in USER.C
*/ extern bool information_screen (short time, ItemPtr item);
extern short query_user (void);

/*
    Functions defined in GRAPHICS.ASM
*/ extern void unpack_plane (int bits, int level, int bytes, char *pack, char *line);
extern void draw_line (int, char *);

/*
    External definitions for variables defined in the ADVISOR.C file and used
    throughout the program.
*/

/*
    Basic user information storage
*/ extern char UserFirstName [11]; /* first name of current user */
extern char UserLastName [16];  /* last name of current user */
extern char UserFullName [27];  /* complete name of current user */
extern char UserPassword [9];   /* password for current user */
extern char UserYearText [5];   /* year of birth */
extern char UserMonthText [3];  /* month of birth */
extern char UserAccess [9];     /* access date for today */ extern short   UserGender;      /* 1 == female, 2 == male */ extern int     UserYear;        /* birth year for user */
extern int     UserAge;         /* user age in years */ extern char UserTopPressure [4];    /* top blood pressure value */
extern char UserBottomPressure [4]; /* bottom blood pressure value */
extern bool    UserHighPressure;    /* high blood pressure flag */ extern long    CurrentUserID;   /* current user ID number */
extern long    LastUserID;      /* last user ID number assigned */ extern bool    ExitFlag;        /* exit requested flag */ extern short   ModuleNumber;    /* index number for module used */

/*
    Path information
*/ extern char *DataPath;      /* path for DATA directory */
extern char *AdvertPath;    /* path for ADVERT directory */
extern char *AdvisorPath;   /* path for ADVISOR directory */

/*
    Consultation information
*/ extern short   ModuleNumber;    /* index number for module used */ extern char SessionSerial [16]; /* serial number assigned to session */ extern int  QueryCount;         /* number of queries in session */
extern char SessionRecord [MAX_QUERIES] [2] [4];    /* record of responses */
extern int  KBRecord [MAX_QUERIES]; /* knowledgebase of queries */ extern bool ReportHold;     /* "no select" recommendation flag */
extern bool ReportFail;     /* failed drug selection flag */
```

```c
extern char ComponentsUsed [CLASS_COMPONENTS];  /* component medicine indices */
extern int  RecommendCount;      /* number of drugs recommended */
extern char RecommendList [5] [DRUG_IDENT];  /* actual recommended drugs */ extern char PrintNum,            /* current print file number */
extern char PrintName [4] [33],  /* names of users for reports printed */ extern char QualifiersPicked [DRUG_CHOICES];   /* qualifier choices made */ extern char SessionAborted;      /* code for session aborted */

/*
    Drug printing information
*/ if INFO_VERSION extern char     DrugFirst [9];   /* first characters of drug name */ endif

/*
    Printer output information
*/ extern int      PageNumber;      /* current page number */
extern int      PageCount;       /* total page count */
extern int      PageLines;       /* number of lines per page */ extern int      CurrentPosition; /* current character position in line */
extern int      LeftMargin;      /* left margin for text */
extern int      RightMargin;     /* right margin for text */
extern int      LineNumber;      /* line number on page */
extern bool     PrinterControl;  /* use printer control codes flag */
extern bool     DumpPrinter;     /* dump file to printer flag */
extern bool     HavePrinted;     /* report has been generated flag */
extern char     MarginChar;      /* character code to print at margins */

/*
    Printer format information
*/ extern char PrintBoldOff [11];   /* escape sequences for printer control */
extern char PrintBoldOn [11];
extern char PrintNormOff [11];
extern char PrintNormOn [11];
extern char PrintInit [11];

/*
    Advertising loop information
*/ extern bool     OnSales;         /* flag for displaying sales screens */
extern int      SalesRecord;     /* current record in sales file */
extern int      AdvertRecord;    /* current record in advertizing file */
extern int      NextWipe;        /* next wipe code to be used */ extern int      IntroSeconds;    /* seconds to display introduction screen */
extern int      AdvertSeconds;   /* seconds to display advertising screen */
extern int      SalesSeconds;    /* seconds to display sales screen */
extern int      SalesPause;      /* seconds between sales text lines */
extern int      ShowIntro;       /* number of screens between intros */

/*
    Help file information
*/ extern int      HelpCount;       /* number of help messages defined */
extern ushort   *HelpOffsets;    /* offsets of help texts in file */

/*
    Definitions for the "USER" database.
*/ extern int      UserDatabase;    /* user database reference */
extern int      UserIndex;       /* user index reference */
extern int      UserNameIndex;   /* user name index reference */ extern long     User_UserID;     /* field definitions */
extern long     User_Lname;
extern long     User_Fname;
extern long     User_Gender;
```

```
extern long     User_BirthDate;
extern long     User_Password;
extern long     User_LastAccess;
extern long     User_BloodP1;
extern long     User_BloodP2;
extern long     User_BPDate;

/*
    Definitions for the "DRUG" database.
*/ extern int      DrugDatabase;    /* drug database reference */
extern int      DrugIndex;       /* ID number index reference */
extern int      DrugUseIndex;    /* drug usage index reference */ extern long     Drug_DrugID;     /* field definitions */
extern long     Drug_ItemNumber;
extern long     Drug_DrugName;
extern long     Drug_GenerCode;
extern long     Drug_GenerName;
extern long     Drug_TcnCode;
extern long     Drug_Strength;
extern long     Drug_Unit;
extern long     Drug_Per;
extern long     Drug_DoseForm;
extern long     Drug_MonoID;
extern long     Drug_TimeDelay;
extern long     Drug_NightTime;
extern long     Drug_SugarFree;
extern long     Drug_AlcohFree;
extern long     Drug_ExtraStren;
extern long     Drug_AdultOK;
extern long     Drug_ChildOK;
extern long     Drug_InfantOK;
extern long     Drug_AdultDose;
extern long     Drug_ChildDose;
extern long     Drug_InfantDose;
extern long     Drug_Age;
extern long     Drug_SigCode;
extern long     Drug_Warning;
extern long     Drug_Ingred;
extern long     Drug_Price;
extern long     Drug_Location;
extern long     Drug_Coupon;
extern long     Drug_PkgSize;
extern long     Drug_Msg1;
extern long     Drug_Msg2;
extern long     Drug_GenLink;
extern long     Drug_AdultRec;
extern long     Drug_ChildRec;
extern long     Drug_InfantRec;

extern short    DrugCount;
extern short    UseCount;

/*
    Definitions for the "MONOGRAF" database.
*/ extern int      MonoDatabase;    /* monograph database reference */
extern int      MonoIndex;       /* ID number index reference */ extern long     Mono_MonoID;     /* field definitions */
extern long     Mono_Abstract;
extern long     Mono_MonoText;

/*
    Store information
*/ extern char StoreName [STORE_NAME];         /* name of the store */
extern char StoreAddress1 [STORE_ADDRESS];  /* address lines */
extern char StoreAddress2 [STORE_ADDRESS];
extern char StoreCity [STORE_CITY];         /* city */
extern char StoreState [STORE_STATE];       /* state */
extern char StoreZip [STORE_ZIP];           /* zip code */

/*
    Module information
*/ extern ModuleRec   ModuleTable [MODULE_COUNT]; /* table of module information */

/*
```

```
    Therapeutic class number information
*/ extern int     ComponentCount;  /* number of component names found */
extern int     TCNCount;        /* number of therapeutic classes defined */
extern char    *ComponentNames [MAX_COMPONENTS];   /* individual component names */
extern bool    ComponentQualifiers [MAX_COMPONENTS];  /* qualified flags */
extern TCNRec  TCNTable [MAX_CLASSES]; /* table of class number definitions */

/*
    Drug form code information
*/ extern int     FormCount;       /* number of dose forms defined */
extern char    FormCodes [FORM_CODES] [2]; /* code letters for dose forms */
extern char    *FormNames [FORM_CODES];    /* dose form names */

/*
    Comments code information
*/

CommentPtr CommentList;        /* list of comment codes and text strings */

/*
    Table of month names
*/ extern char *MonthText [12];   /* text strings for month names */

/*
    Knowledgebase information
*/ extern int KBCount;                    /* number of knowledgebases known */
extern char *KBSelects [KB_COUNT];    /* selection strings for user choice */
extern char KBMapping [KB_COUNT];     /* mapping choices to knowledgebases */
extern KBRec KBTable [KB_COUNT];      /* knowledgebase file information */
extern char *QualifyText;             /* qualifier text string */

/*
    Debug information
*/ extern bool DebugFlag;         /* display debug information flag */
extern bool ScreenFlag;        /* selection displayed on screen flag */

/*
    Text information
*/ extern short TextHeights [4];  /* item text fonts heights */
extern short TextWidths [4];   /* item text fonts widths */
extern short TextColors [4];   /* item text fonts colors */

/*
    Graphics information
*/ extern struct videoconfig VideoConfig;  /* video configuration information */
```

We claim:

1. A system including a personal computer having an input device, a display, a storage device and a processor adapted to execute a computer program loaded from said storage device into a random access memory, said system for assisting a user to select appropriate non-prescription medications, said system comprising:

a) means for prompting the user to input identifying information to uniquely identify the user from the other uses of the system and to input predetermined information for subsequent use by execution by said processor of said computer program causing first prompting information to be displayed on said display;

b) said input device for allowing the user to input said identifying information to uniquely identify the user from other uses of the system, to answer predetermined questions and to input said predetermined information, c) means for prompting the user to select a main symptom of an illness or injury by execution of said computer program causing second prompting information to be displayed on said display, said input device for allowing the user to select said main symptom;

d) means to generate a list of ingredients of non-prescription medications, wherein said list generation means is a knowledgebase loaded from said storage device in to said random access memory which when executed by said processor, generates predetermined questions which are displayed on said display based upon the inputted identifying information, the inputted predetermined information and the selected main symptom, and uses the user's answers to the predetermined questions to generate said list of ingredients, and wherein said knowledge base determines the existence of potential problems with the customer using non-prescription medications which contain at least one ingredient on said list of ingredients;

e) means using the generated list of ingredients and any determined potential problems to generate a report of recommended non-prescription medications which may be purchased to relieve the symptoms of the selected illness or injury, said generated respect being generated by execution by said processor of said computer program which causes said generated report to appear on said display.

2. The system defined by claim 1 wherein said report generating means uses said generated list of ingredients to search a database containing products with their component medications, and after selecting a first product containing as a component medication at least one ingredient from said generated list of ingredients, removes the component medication present in the selected product from the generated list of ingredients, and if any items remain in the resulting list, selects a second product containing as a component medication at least one ingredient from said resulting list, and then continues said selection and removal from said resulting list until each component medication in the generated list of ingredients is present in one and only one selected product.

3. A method for assisting a user to select appropriate non-prescription medications using a personal computer having an input device, a display, a storage device and a processor adapted to execute a computer program loaded from said storage device into a random access memory, said method comprising the steps of:

a) prompting the user on said display to input the identifying information to uniquely identify the user from other users of the system and to input predetermined information for subsequent use;

b) inputting with said input device said identifying information and said predetermined information supplied by the user;

c) prompting the user on said display to select a main symptom of an illness or injury;

d) inputting with said input device said main symptom selected by the user;

e) generating list a list of ingredients of non-prescription medications, wherein said list of ingredients is generated by the execution of a knowledgebase loaded from said storage device into said random access memory which generates predetermined questions based upon the inputted identifying information, the inputted predetermined information and the selected main symptom, and uses the user's answers to the predetermined questions input with said input device to generate said list of ingredients, and wherein said knowledge base determines the existence of potential problems with the customer using non-prescription medications which contain at least one ingredient on said list of ingredients;

f) using the generated list of ingredients and any determined potential problems to generate a report of recommended non-prescription medications which may be purchased to relieve the symptoms of the selected illness of injury.

4. The method defined by claim 3 wherein said report generation step uses said generated list of ingredients to search a database containing products with their component medications, and after selecting a first product containing as a component medication at least one ingredient from said generated list of ingredients, removes the component medication present in the selected product from the generated list of ingredients, and if any items remain in the resulting list, selects a second product containing as a component medication at least one ingredient from said resulting list, and then continues said selection and removal from said resulting list until each component medication in the generated list of ingredients is present in one and only one selected product.

* * * * *